(12) United States Patent
Steinmeyer et al.

(10) Patent No.: US 6,642,218 B2
(45) Date of Patent: Nov. 4, 2003

(54) VITAMIN D DERIVATIVES WITH CARBO- OR HETEROCYCLIC SUBSTITUENTS AT C-25, A PROCESS FOR THEIR PRODUCTION, INTERMEDIATE PRODUCTS AND THEIR USE FOR PRODUCING MEDICAMENTS

(75) Inventors: Andreas Steinmeyer, Berlin (DE); Gerald Kirsch, Berlin (DE); Günter Neef, Berlin (DE); Katica Schwarz, Berlin (DE); Ruth Thieroff-Ekerdt, Berlin (DE); Herbert Wiesinger, Berlin (DE); Martin Haberey, Berlin (DE); Marianne Fahnrich, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/180,018
(22) PCT Filed: Apr. 21, 1997
(86) PCT No.: PCT/EP97/02013
§ 371 (c)(1),
(2), (4) Date: Dec. 11, 1998
(87) PCT Pub. No.: WO97/41096
PCT Pub. Date: Nov. 6, 1997

(65) Prior Publication Data
US 2002/0049344 A1 Apr. 25, 2002

(30) Foreign Application Priority Data
Apr. 30, 1996 (DE) .......................... 196 19 036

(51) Int. Cl.$^7$ .................. A61K 31/59; A61K 31/42; A61K 31/58; C07D 413/00; C07C 401/00
(52) U.S. Cl. .................. 514/172; 514/167; 514/172; 514/374; 514/378; 514/375; 514/379; 548/237; 548/239; 552/653
(58) Field of Search .......................... 552/653; 514/167, 514/172, 374, 375, 378, 379; 548/237, 239

(56) References Cited

U.S. PATENT DOCUMENTS

| | | | | |
|---|---|---|---|---|
| 4,851,401 A | * | 7/1989 | DeLuca et al. | 514/167 |
| 5,397,775 A | * | 3/1995 | De Luca et al. | 514/167 |
| 5,446,035 A | | 8/1995 | Neef et al. | |
| 5,478,955 A | * | 12/1995 | DeLuca et al. | 552/505 |
| 5,532,228 A | | 7/1996 | Neef et al. | 514/167 |
| 5,585,368 A | | 12/1996 | Steinmeyer et al. | |
| 5,665,716 A | | 9/1997 | Kirsch et al. | |
| 5,700,791 A | | 12/1997 | Steinmeyer et al. | |
| 6,372,731 B1 | | 4/2002 | Kirsch et al. | |
| 6,376,480 B1 | | 4/2002 | Kirsch et al. | |

FOREIGN PATENT DOCUMENTS

| | | |
|---|---|---|
| DE | 4003854 | 8/1991 |
| DE | 42 00 783 | 7/1993 |
| DE | 42 20 757 A1 | 1/1994 |
| EP | 0 421 561 A2 | 10/1990 |
| EP | 0 549 318 | 6/1993 |
| EP | 0 619 305 | 10/1994 |
| WO | WO 93/12081 A1 | 6/1993 |
| WO | 9400428 | 1/1994 |
| WO | 9426707 | 11/1994 |
| WO | 952577 | 1/1995 |
| WO | 9501960 | 1/1995 |
| WO | 9503273 | 2/1995 |
| WO | 9516672 | 6/1995 |
| WO | 9525718 | 9/1995 |
| WO | 95 337 16 A | 12/1995 |
| WO | 9700242 | 1/1997 |

OTHER PUBLICATIONS

Godtfredsen, Wagn Ole (CA 119125211 abstract of GB 2260904), 1993.*
Sicinski et al. (CA 103:596311 abstract of Bioorg. Chem. (1985), 13(2), 158–69.*

* cited by examiner

*Primary Examiner*—Sabiha Qazi
(74) *Attorney, Agent, or Firm*—Millen, White, Zelano, Branigan, P.C.

(57) ABSTRACT

The invention relates to vitamin D derivatives of formula (I), processes for the production thereof and uses thereof:

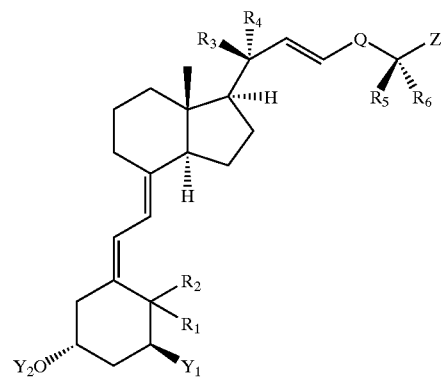

wherein $Y_1$, $Y_2$, $R_1$–$R_6$, Q and Z are as defined herein.

28 Claims, No Drawings

VITAMIN D DERIVATIVES WITH CARBO- OR HETEROCYCLIC SUBSTITUENTS AT C-25, A PROCESS FOR THEIR PRODUCTION, INTERMEDIATE PRODUCTS AND THEIR USE FOR PRODUCING MEDICAMENTS

Pursuant to 35 U.S.C. §371, this is a national stage application of PCT/EP97/02013, filed Apr. 21, 1997.

This invention relates to vitamin D derivatives with substituents at C-25 of general formula I

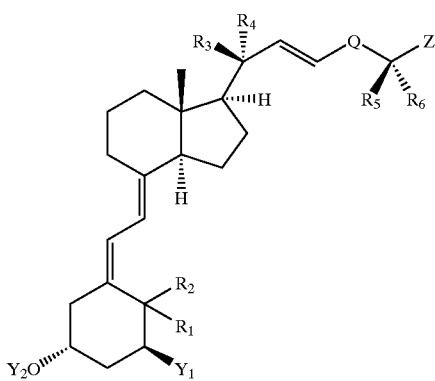

in which
- $Y_1$ means a hydrogen atom, a hydroxyl group, an alkanoyloxy group with 1 to 12 C atoms or an aroyloxy group,
- $Y_2$ means a hydrogen atom or an alkanoyl group with 1 to 12 C atoms or an aroyl group,
- $R_1$ and $R_2$ each mean a hydrogen atom or together an exocyclic methylene group,
- $R_3$ and $R_4$, independently of one another, mean a hydrogen atom, a chlorine or fluorine atom, an alkyl group with 1 to 4 carbon atoms, together a methylene group or together with quaternary carbon atom 20 a 3- to 7-membered, saturated or unsaturated carbocyclic ring,
- Q means a straight-chain or branched carbon unit with up to 10 carbon atoms, which at any positions can have hydroxyl groups (in α- or β-position), which in turn can be etherified or esterified, keto groups, amino groups or halogen atoms,
- $R_5$ and $R_6$ at the same time each mean a hydrogen atom, a chlorine or fluorine atom, a trifluoromethyl group, a straight-chain or branched-chain, saturated or unsaturated hydrocarbon radical with up to 4 carbon atoms or $R_5$ and $R_6$ together with carbon atom 25 mean a 3- to 7-membered, saturated or unsaturated carbocyclic ring and
- Z means a five- or six-membered carbo- or heterocyclic ring, which can be saturated, unsaturated or aromatic, and at any positions one or more alkyl chains, which can be straight-chain or branched, saturated or unsaturated, and at any points can be interrupted by oxa, thia or aza groups (substituted or unsubstituted) or sulfoxide or sulfo groups or can carry substituents (hydroxy groups, halogen atoms), process for their production, intermediate products in the production process as well as their use for the production of pharmaceutical agents.

The alkanoyl or alkanoyloxy groups with 1 to 12 C atoms that are possible for radicals $Y_1$ and $Y_2$ are derived especially from saturated carboxylic acids. These radicals can be cyclic, acyclic, carbocyclic or heterocyclic. The preferred radicals are derived from $C_1$ to $C_9$, especially $C_2$ to $C_5$ alkanecarboxylic acids, such as, for example, acetyl(oxy), propionyl(oxy), and butyryl(oxy).

As aroyl(oxy) groups, the benzoyl(oxy) groups and substituted benzoyl(oxy) groups are preferred.

For $R_3$ and $R_4$, the following preferred combinations apply: $R_3$=H, $R_4$=methyl or $R_3$=methyl, $R_4$=H; $R_3$=F, $R_4$=methyl or $R_3$=methyl, $R_4$=F; $R_3$, $R_4$=methyl; $R_3$ and $R_4$ together form a methylene group or together with tertiary carbon atom 20 form a cyclopropyl ring.

For Q, the following preferences apply:
- Q is an unsubstituted, unbranched alkyl unit with 1, 2 or 3 carbon atoms or
- Q is a hydroxymethylene group (hydroxyl group in α- or β-position) or
- Q=—CH(OH)—CH$_2$— or —CH(OH)—CH$_2$—CH$_2$— (hydroxyl groups in α- or β-position),
- substituents, preferably alkyl groups, for all described variants at C-24a are possible.

For $R_5$ and $R_6$, the following preferences apply:
$R_5$=$R_6$=methyl or ethyl; $R_5$ and $R_6$ together with carbon atom C-25 form a cyclopropyl, cyclobutyl, cyclopentyl or cyclohexyl ring.

Especially preferred are the cases: $R_5$=$R_6$=methyl, and $R_5$ and $R_6$ together with carbon atom C-25 form a cyclopropyl ring.

For Z, the following preferences apply:
For the five-membered case, furan, tetrahydrofuran, thiophene, pyrrole, pyrrolidine, imidazole, pyrazole, oxazole, thiazole, isoxazole, triazole, oxadiazole or thiadiazole rings, which at any positions can carry one or more alkyl chains with 1 to 12 carbon atoms, are preferred. These alkyl chains can be straight-chain or branched, saturated or unsaturated and can be interrupted by heteroatoms (O, S, N also substituted). They can also carry other substituents (hydroxyl groups, halogen atoms).

For the six-membered case, the phenyl, pyridine, pyrazine, pyrimidine, pyridazine, piperidine or tetrahydropyran rings are preferred, which, like the five-membered rings, can be substituted in one or more places with the above-mentioned alkyl chains.

Especially preferred are: imidazole, oxazole, thiazole, furan, thiophene, pyrrole, isoxazole, pyrazole, triazole, pyridine, pyrimidine and phenyl rings, which each carry a straight-chain, saturated C1 to C12 alkyl chain.

Especially preferred according to this invention are the following compounds:

(5Z,7E,22E)-(1S,3R,24R)-25-(5-Propyloxazol-2-yl)-26,27-cyclo-9,10-secocholesta-5,7,10(19),22-tetraene-1,3,24-triol (5Z,7E,22E)-(1S,3R,24S)-25-(5-propyloxazol-2-yl)-26,27-cyclo-9,10-secocholesta-5,7,10(19),22-tetraene-1,3,24-triol (5Z,7E,22E)-(1S,3R,24R)-25-(5-methyloxazol-2-yl)-26,27-cyclo-9,10-secocholesta-5,7,10(19),22-tetraene-1,3,24-triol (5Z,7E,22E)-(1S,3R,24S)-25-(5-methyloxazol-2-yl)-26,27-cyclo-9,10-secocholesta-5,7,10(19),22-tetraene-1,3,24-triol (5Z,7E,22E)-(1S,3R,24R)-25-(5-ethyloxazol-2-yl)-26,27-cyclo-9,10-secocholesta-5,7,10(19),22-tetraene-1,3,24-triol (5Z,7E,22E)-(1S,3R,24S)-25-(5-ethyloxazol-2-yl)-26,27-cyclo-9,10-secocholesta-5,7,10(19),22-tetraene-1,3,24-triol (5Z,7E,22E)-(1S,3R,24R)-25-(5-butyloxazol-2-yl)-26,27-cyclo-9,10-secocholesta-5,7,10(19),22-tetraene-1,3,24-triol (5Z,7E,22E)-(1S,3R,24S)-25-(5-butyloxazol-2-yl)-26,27-cyclo-9,10-secocholesta-5,7,10(19),22-tetraene-1,3,24-triol (5Z,7E,22E)-(1S,3R,24R)-25-(5-pentyloxazol-2-yl)-26,27-cyclo-9,10-secocholesta-5,7,10(19),22-tetraene-1,3,24-triol (5Z,7E,22E)-(1S,3R,24S)-25-(5-pentyloxazol-2-yl)-26,27-cyclo-9,10-secocholesta-5,7,10(19),22-tetraene-1,3,24-triol (5Z,7E,22E)-(1S,3R,24R)-25-(5-propylthiazol-2-yl)-26,27-cyclo-9,10-secocholesta-5,7,10(19),22-tetraene-1,3,24-triol (5Z,7E,22E)-(1S,3R,24S)-25-(5-propylthiazol-2-yl)-26,27-cyclo-9,10-secocholesta-5,7,10(19),22-tetraene-1,3,24-triol (5Z,7E,22E)-(1S,3R,24R)-25-(5-methylthiazol-2-yl)-26,27-cyclo-9,10-secocholesta-5,7,10(19),22-tetraene-1,3,24-triol (5Z,7E,22E)-(1S,3R,24S)-25-(5-methylthiazol-2-yl)-26,27-cyclo-9,10-secocholesta-5,7,10(19),22-tetraene-1,3,24-triol (5Z,7E,22E)-(1S,3R,24R)-25-(5-ethylthiazol-2-yl)-26,27-cyclo-9,10-secocholesta-5,7,10(19),22-tetraene-1,3,24-triol (5Z,7E,22E)-(1S,3R,24S)-25-(5-ethylthiazol-2-yl)-26,27-cyclo-9,10-secocholesta-5,7,10(19),22-tetraene-1,3,24-triol (5Z,7E,22E)-(1S,3R,24R)-25-(5-butylthiazol-2-yl)-26,27-cyclo-9,10-secocholesta-5,7,10(19),22-tetraene-1,3,24-triol (5Z,7E,22E)-(1S,3R,24S)-25-(5-butylthiazol-2-yl)-26,27-cyclo-9,10-secocholesta-5,7,10(19),22-tetraene-1,3,24-triol (5Z,7E,22E)-(1S,3R,24R)-25-(5-pentylthiazol-2-yl)-26,27-cyclo-9,10-secocholesta-5,7,10(19),22-tetraene-1,3,24-triol (5Z,7E,22E)-(1S,3R,24S)-25-(5-pentylthiazol-2-yl)-26,27-cyclo-9,10-secocholesta-5,7,10(19),22-tetraene-1,3,24-triol (5Z,7E,22E)-(1S,3R,24R)-25-(5-propylthiazol-2-yl)-26,27-cyclo-9,10-secocholesta-5,7,10(19),22-tetraene-1,3,24-triol (5Z,7E,22E)-(1S,3R,24S)-25-(5-propylthiazol-2-yl)-26,27-cyclo-9,10-secocholesta-5,7,10(19),22-tetraene-1,3,24-triol (5Z,7E,22E)-(1S,3R,24R)-25-(5-methylimidazol-2-yl)-26,27-cyclo-9,10-secocholesta-5,7,10(19),22-tetraene-1,3,24-triol (5Z,7E,22E)-(1S,3R,24S)-25-(5-methylimidazol-2-yl)-26,27-cyclo-9,10-secocholesta-5,7,10(19),22-tetraene-1,3,24-triol (5Z,7E,22E)-(1S,3R,24R)-25-(5-ethylthiazol-2-yl)-26,27-cyclo-9,10-secocholesta-5,7,10(19),22-tetraene-1,3,24-triol (5Z,7E,22E)-(1S,3R,24S)-25-(5-ethylthiazol-2-yl)-26,27-cyclo-9,10-secocholesta-5,7,10(19),22-tetraene-1,3,24-triol (5Z,7E,22E)-(1S,3R,24R)-25-(5-butylimidazol-2-yl)-26,27-cyclo-9,10-secocholesta-5,7,10(19),22-tetraene-1,3,24-triol (5Z,7E,22E)-(1S,3R,24S)-25-(5-butylimidazol-2-yl)-26,27-cyclo-9,10-secocholesta-5,7,10(19),22-tetraene-1,3,24-triol (5Z,7E,22E)-(1S,3R,24R)-25-(5-pentylimidazol-2-yl)-26,27-cyclo-9,10-secocholesta-5,7,10(19),22-tetraene-1,3,24-triol (5Z,7E,22E)-(1S,3R,24S)-25-(5-pentylimidazol-2-yl)-26,27-cyclo-9,10-secocholesta-5,7,10(19),22-tetraene-1,3,24-triol (5Z,7E,22E)-(1S,3R,24R)-25-(5-propylfuran-2-yl)-26,27-cyclo-9,10-secocholesta-5,7,10(19),22-tetraene-1,3,24-triol (5Z,7E,22E)-(1S,3R,24S)-25-(5-propylfuran-2-yl)-26,27-cyclo-9,10-secocholesta-5,7,10(19),22-tetraene-1,3,24-triol (5Z,7E,22E)-(1S,3R,24R)-25-(5-methylfuran-2-yl)-26,27-cyclo-9,10-secocholesta-5,7,10(19),22-tetraene-1,3,24-triol (5Z,7E,22E)-(1S,3R,24S)-25-(5-methylfuran-2-yl)-26,27-cyclo-9,10-secocholesta-5,7,10(19),22-tetraene-1,3,24-triol (5Z,7E,22E)-(1S,3R,24R)-25-(5-ethylfuran-2-yl)-26,27-cyclo-9,10-secocholesta-5,7,10(19),22-tetraene-1,3,24-triol (5Z,7E,22E)-(1S,3R,24S)-25-(5-ethylfuran-2-yl)-26,27-cyclo-9,10-secocholesta-5,7,10(19),22-tetraene-1,3,24-triol (5Z,7E,22E)-(1S,3R,24R)-25-(5-butylfuran-2-yl)-26,27-cyclo-9,10-secocholesta-5,7,10(19),22-tetraene-1,3,24-triol (5Z,7E,22E)-(1S,3R,24S)-25-(5-butylfuran-2-yl)-26,27-cyclo-9,10-secocholesta-5,7,10(19),22-tetraene-1,3,24-triol (5Z,7E,22E)-(1S,3R,24R)-25-(5-pentylfuran-2-yl)-26,27-cyclo-9,10-secocholesta-5,7,10(19),22-tetraene-1,3,24-triol (5Z,7E,22E)-(1S,3R,24S)-25-(5-pentylfuran-2-yl)-26,27-cyclo-9,10-secocholesta-5,7,10(19),22-tetraene-1,3,24-triol (5Z,7E,22E)-(1S,3R,24R)-25-(5-propylthiophen-2-yl)-26,27-cyclo-9,10-secocholesta-5,7,10(19),22-tetraene-1,3,24-triol (5Z,7E,22E)-(1S,3R,24S)-25-(5-propylthiophen-2-yl)-26,27-cyclo-9,10-secocholesta-5,7,10(19),22-tetraene-1,3,24-triol (5Z,7E,22E)-(1S,3R,24R)-25-(5-methylthiophen-2-yl)-26,27-cyclo-9,10-secocholesta-5,7,10(19),22-tetraene-1,3,24-triol (5Z,7E,22E)-(1S,3R,24S)-25-(5-methylthiophen-2-yl)-26,27-cyclo-9,10-secocholesta-5,7,10(19),22-tetraene-1,3,24-triol (5Z,7E,22E)-(1S,3R,24R)-25-(5-ethylthiophen-2-yl)-26,27-cyclo-9,10-secocholesta-5,7,10(19),22-tetraene-1,3,24-triol (5Z,7E,22E)-(1S,3R,24S)-25-(5-ethylthiophen-2-yl)-26,27-cyclo-9,10-secocholesta-5,7,10(19),22-tetraene-1,3,24-triol (5Z,7E,22E)-(1S,3R,24R)-25-(5-butylthiophen-2-yl)-26,27-cyclo-9,10-secocholesta-5,7,10(19),22-tetraene-1,3,24-triol (5Z,7E,22E)-(1S,3R,24S)-25-(5-butylthiophen-2-yl)-26,27-cyclo-9,10-secocholesta-5,7,10(19),22-tetraene-1,3,24-triol (5Z,7E,22E)-(1S,3R,24R)-25-(5-pentylthiophen-2-yl)-26,27-cyclo-9,10-secocholesta-5,7,10(19),22-tetraene-1,3,24-triol (5Z,7E,22E)-(1S,3R,24S)-25-(5-pentylthiophen-2-yl)-26,27-cyclo-9,10-secocholesta-5,7,10(19),22-tetraene-1,3,24-triol (5Z,7E,22E)-(1S,3R,24R)-25-(5-propylpyrrol-2-yl)-26,27-cyclo-9,10-secocholesta-5,7,10(19),22-tetraene-1,3,24-triol (5Z,7E,22E)-(1S,3R,24S)-25-(5-propylpyrrol-2-yl)-26,27-cyclo-9,10-secocholesta-5,7,10(19),22-tetraene-1,3,24-triol (5Z,7E,22E)-(1S,3R,24R)-25-(5-methylpyrrol-2-yl)-26,27-cyclo-9,10-secocholesta-5,7,10(19),22-tetraene-1,3,24-triol (5Z,7E,22E)-(1S,3R,24S)-25-(5-methylpyrrol-2-yl)-26,27-cyclo-9,10-secocholesta-5,7,10(19),22-tetraene-1,3,24-triol (5Z,7E,22E)-(1S,3R,24R)-25-(5-ethylpyrrol-2-yl)-26,27-cyclo-9,10-secocholesta-5,7,10(19),22-tetraene-1,3,24-triol (5Z,7E,22E)-(1S,3R,24S)-25-(5-ethylpyrrol-2-yl)-26,27-cyclo-9,10-secocholesta-5,7,10(19),22-tetraene-1,3,24-triol (5Z,7E,22E)-(1S,3R,24R)-25-(5-butylpyrrol-2-yl)-26,27-cyclo-9,10-secocholesta-5,7,10(19),22-tetraene-1,3,24-triol (5Z,7E,22E)-(1S,3R,24S)-25-(5-butylpyrrol-2-yl)-26,27-cyclo-9,10-secocholesta-5,7,10(19),22-tetraene-1,3,24-triol (5Z,7E,22E)-(1S,3R,24R)-25-(5-pentylpyrrol-2-yl)-26,27-cyclo-9,10-secocholesta-5,7,10(19),22-tetraene-1,3,24-triol (5Z,7E,22E)-(1S,3R,24S)-25-(5-pentylpyrrol-2-yl)-26,27-cyclo-9,10-secocholesta-5,7,10(19),22-tetraene-1,3,24-triol (5Z,7E,22E)-(1S,3R,24R)-25-(4-propyloxazol-2-yl)-26,27-cyclo-9,10-secocholesta-5,7,10(19),22-tetraene-1,3,24-triol (5Z,7E,22E)-(1S,3R,24S)-25-(4-propyloxazol-2-yl)-26,27-cyclo-9,10-secocholesta-5,7,10(19),22-tetraene-1,3,24-triol (5Z,7E,22E)-(1S,3R,24R)-25-(4-methyloxazol-2-yl)-26,27-cyclo-9,10-secocholesta-5,7,10(19),22-tetraene-1,3,24-triol (5Z,7E,22E)-(1S,3R,24S)-25-(4-methyloxazol-2-yl)-26,27-cyclo-9,10-secocholesta-5,7,10(19),22-tetraene-1,3,24-triol (5Z,7E,22E)-(1S,3R,24R)-25-(4-ethyloxazol-2-yl)-26,27-cyclo-9,10-secocholesta-5,7,10(19),22-tetraene-1,3,24-triol (5Z,7E,22E)-(1S,3R,24S)-25-(4-ethyloxazol-2-yl)-26,27-cyclo-9,10-secocholesta-5,7,10(19),22-tetraene-1,3,24-triol (5Z,7E,22E)-(1S,3R,24R)-25-(4-butyloxazol-2-yl)-26,27-cyclo-9,10-secocholesta-5,7,10(19),22-tetraene-1,3,24-triol (5Z,7E,22E)-(1S,3R,24S)-25-(4-butyloxazol-2-yl)-26,27-cyclo-9,10-secocholesta-5,7,10(19),22-tetraene-1,3,24-triol (5Z,7E,22E)-(1S,3R,24R)-25-(4-pentyloxazol-2-yl)-26,27-cyclo-9,10-secocholesta-5,7,10(19),22-tetraene-1,3,24-triol (5Z,7E,22E)-(1S,3R,24S)-25-(4-pentyloxazol-2-yl)-26,27-cyclo-9,10-secocholesta-5,7,10(19),22-tetraene-1,3,24-triol (5Z,7E,22E)-(1S,3R,24R)-25-(4-propylthiazol-2-yl)-26,27-cyclo-9,10-secocholesta-5,7,10(19),22-tetraene-1,3,24-triol (5Z,7E,22E)-(1S,3R,24S)-25-(4-propylthiazol-2-yl)-26,27-cyclo-9,10-secocholesta-5,7,10(19),22-tetraene-1,3,24-triol (5Z,7E,22E)-(1S,3R,24R)-25-(4-methylthiazol-2-yl)-26,27-cyclo-9,10-secocholesta-5,7,10(19),22-tetraene-1,3,24-triol (5Z,7E,22E)-(1S,3R,24S)-25-(4-methylthiazol-2-yl)-26,27-cyclo-9,10-secocholesta-5,7,10(19),22-tetraene-1,3,24-triol (5Z,7E,22E)-(1S,3R,24R)-25-(4-ethylthiazol-2-yl)-26,27-cyclo-9,10-secocholesta-5,7,10(19),22-tetraene-1,3,24-triol (5Z,7E,22E)-(1S,3R,24S)-25-(4-ethylthiazol-2-yl)-26,27-cyclo-9,10-secocholesta-5,7,10(19),22-tetraene-1,3,24-triol (5Z,7E,22E)-(1S,3R,24R)-25-(4-butylthiazol-2-yl)-26,27-cyclo-9,10-secocholesta-5,7,10(19),22-tetraene-1,3,24-triol (5Z,7E,22E)-(1S,3R,24S)-25-(4-butylthiazol-2-yl)-26,27-cyclo-9,10-secocholesta-5,7,10(19),22-tetraene-1,3,24-triol (5Z,7E,22E)-(1S,3R,24S)-25-(4-pentylthiazol-2-yl)-26,27-cyclo-9,10-secocholesta-5,7,10(19),22-tetraene-1,3,24-triol (5Z,7E,22E)-(1S,3R,24S)-25-(4-pentylthiazol-2-yl)-26,27-cyclo-9,10-secocholesta-5,7,10(19),22-tetraene-1,3,24-triol (5Z,7E,22E)-(1S,3R,24R)-25-(4-propylimidazol-2-yl)-26,27-cyclo-9,10-secocholesta-5,7,10(19),22-tetraene-1,3,24-triol (5Z,7E,22E)-(1S,3R,24S)-25-(4-propylimidazol-2-yl)-26,27-cyclo-9,10-secocholesta-5,7,10(19),22-tetraene-1,3,24-triol (5Z,7E,22E)-(1S,3R,24R)-25-(4-methylimidazol-2-yl)-26,27-cyclo-9,10-secocholesta-5,7,10(19),22-tetraene-1,3,24-triol (5Z,7E,22E)-(1S,3R,24S)-25-(4-methylimidazol-2-yl)-26,27-cyclo-9,10-secocholesta-5,7,10(19),22-tetraene-1,3,24-triol (5Z,7E,22E)-(1S,3R,24R)-25-(4-ethylthiazol-2-yl)-26,27-cyclo-9,10-secocholesta-5,7,10(19),22-tetraene-1,3,24-triol (5Z,7E,22E)-(1S,3R,24S)-25-(4-ethylthiazol-2-yl)-26,27-cyclo-9,10-secocholesta-5,7,10(19),22-tetraene-1,3,24-triol (5Z,7E,22E)-(1S,3R,24R)-25-(4-butylthiazol-2-yl)-26,27-cyclo-9,10-secocholesta-5,7,10(19),22-tetraene-1,3,24-triol (5Z,7E,22E)-(1S,3R,24S)-25-(4-butylthiazol-2-yl)-26,27-cyclo-9,10-secocholesta-5,7,10(19),22-tetraene-1,3,24-triol (5Z,7E,22E)-(1S,3R,24R)-25-(4-pentylimidazol-2-yl)-26,27-cyclo-9,10-secocholesta-5,7,10(19),22-tetraene-1,3,24-triol (5Z,7E,22E)-(1S,3R,24S)-25-(4-pentylimidazol-2-yl)-26,27-cyclo-9,10-secocholesta-5,7,10(19),22-tetraene-1,3,24-triol (5Z,7E,22E)-(1S,3R,24R)-25-(4-propylfuran-2-yl)-26,27-cyclo-9,10-secocholesta-5,7,10(19),22-tetraene-1,3,24-triol (5Z,7E,22E)-(1S,3R,24S)-25-(4-propylfuran-2-yl)-26,27-cyclo-9,10-secocholesta-5,7,10(19),22-tetraene-1,3,24-triol (5Z,7E,22E)-(1S,3R,24R)-25-(4-methylfuran-2-yl)-26,27-cyclo-9,10-secocholesta-5,7,10(19),22-tetraene-1,3,24-triol (5Z,7E,22E)-(1S,3R,24S)-25-(4-methylfuran-2-yl)-26,27-cyclo-9,10-secocholesta-5,7,10(19),22-tetraene-1,3,24-triol (5Z,7E,22E)-(1S,3R,24R)-25-(4-ethylfuran-2-yl)-26,27-cyclo-9,10-secocholesta-5,7,10(19),22-tetraene-1,3,24-triol (5Z,7E,22E)-(1S,3R,24S)-25-(4-ethylfuran-2-yl)-26,27-cyclo-9,10-secocholesta-5,7,10(19),22-tetraene-1,3,24-triol (5Z,7E,22E)-(1S,3R,24R)-25-(4-butylfuran-2-yl)-26,27-cyclo-9,10-secocholesta-5,7,10(19),22-tetraene-1,3,24-triol (5Z,7E,22E)-(1S,3R,24S)-25-(4-butylfuran-2-yl)-26,27-cyclo-9,10-secocholesta-5,7,10(19),22-tetraene-1,3,24-triol (5Z,7E,22E)-(1S,3R,24R)-25-(4-pentylfuran-2-yl)-26,27-cyclo-9,10-secocholesta-5,7,10(19),22-tetraene-1,3,24-triol (5Z,7E,22E)-(1S,3R,24S)-25-(4-pentylfuran-2-yl)-26,27-cyclo-9,10-secocholesta-5,7,10(19),22-tetraene-1,3,24-triol (5Z,7E,22E)-(1S,3R,24R)-25-(4-propylthiophen-2-yl)-26,27-cyclo-9,10-secocholesta-5,7,10(19),22-tetraene-1,3,24-triol (5Z,7E,22E)-(1S,3R,24S)-25-(4-propylthiophen-2-yl)-26,27-cyclo-9,10-secocholesta-5,7,10(19),22-tetraene-1,3,24-triol (5Z,7E,22E)-(1S,3R,24R)-25-(4-methylthiophen-2-yl)-26,27-cyclo-9,10-secocholesta-5,7,10(19),22-tetraene-1,3,24-triol (5Z,7E,22E)-(1S,3R,24S)-25-(4-methylthiophen-2-yl)-26,27-cyclo-9,10-secocholesta-5,7,10(19),22-tetraene-1,3,24-triol (5Z,7E,22E)-(1S,3R,24R)-25-(4-ethylthiophen-2-yl)-26,27-cyclo-9,10-secocholesta-5,7,10(19),22-tetraene-1,3,24-triol (5Z,7E,22E)-(1S,3R,24S)-25-(4-ethylthiophen-2-yl)-26,27-cyclo-9,10-secocholesta-5,7,10(19),22-tetraene-1,3,24-triol (5Z,7E,22E)-(1S,3R,24R)-25-(4-butylthiophen-2-yl)-26,27-cyclo-9,10-secocholesta-5,7,10(19),22-tetraene-1,3,24-triol (5Z,7E,22E)-(1S,3R,24S)-25-(4-butylthiophen-2-yl)-26,27-cyclo-9,10-secocholesta-5,7,10(19),22-tetraene-1,3,24-triol (5Z,7E,22E)-(1S,3R,24R)-25-(4-pentylthiophen-2-yl)-26,27-cyclo-9,10-secocholesta-5,7,10(19),22-tetraene-1,3,24-triol (5Z,7E,22E)-(1S,3R,24S)-25-(4-pentylthiophen-2-yl)-26,27-cyclo-9,10-secocholesta-5,7,10(19),22-tetraene-1,3,24-triol (5Z,7E,22E)-(1S,3R,24R)-25-(4-propylpyrrol-2-yl)-26,27-cyclo-9,10-secocholesta-5,7,10(19),22-tetraene-1,3,24-triol (5Z,7E,22E)-(1S,3R,24S)-25-(4-propylpyrrol-2-yl)-26,27-cyclo-9,10-secocholesta-5,7,10(19),22-tetraene-1,3,24-triol (5Z,7E,22E)-(1S,3R,24R)-25-(4-methylpyrrol-2-yl)-26,27-cyclo-9,10-secocholesta-5,7,10(19),22-tetraene-1,3,24-triol (5Z,7E,22E)-(1S,3R,24S)-25-(4-methylpyrrol-2-yl)-26,27-cyclo-9,10-secocholesta-5,7,10(19),22-tetraene-1,3,24-triol (5Z,7E,22E)-(1S,3R,24R)-25-(4-ethylpyrrol-2-yl)-26,27-cyclo-9,10-secocholesta-5,7,10(19),22-tetraene-1,3,24-triol (5Z,7E,22E)-(1S,3R,24S)-25-(4-ethylpyrrol-2-yl)-26,27-cyclo-9,10-secocholesta-5,7,10(19),22-tetraene-1,3,24-triol (5Z,7E,22E)-(1S,3R,24R)-25-(4-butylpyrrol-2-yl)-26,27-cyclo-9,10-secocholesta-5,7,10(19),22-tetraene-1,3,24-triol (5Z,7E,22E)-(1S,3R,24S)-25-(4-butylpyrrol-2-yl)-26,27-cyclo-9,10-secocholesta-5,7,10(19),22-tetraene-1,3,24-triol (5Z,7E,22E)-(1S,3R,24R)-25-(4-pentylpyrrol-2-yl)-26,27-cyclo-9,10-secocholesta-5,7,10(19),22-tetraene-1,3,24-triol (5Z,7E,22E)-(1S,3R,24S)-25-(4-pentylpyrrol-2-yl)-26,27-cyclo-9,10-secocholesta-5,7,10(19),22-tetraene-1,3,24-triol (5Z,7E,22E)-(1S,3R,24R)-25-(3-methyl-1,2,4-oxadiazol-5-yl)-26,27-cyclo-9,10-secocholesta-5,7,10(19),22-tetraene-1,3,24-triol (5Z,7E,22E)-(1S,3R,24S)-25-(3-methyl-1,2,4-oxadiazol-5-yl)-26,27-cyclo-9,10-secocholesta-5,7,10(19),22-tetraene-1,3,24-triol (5Z,7E,22E)-(1S,3R,24R)-25-(3-ethyl-1,2,4-oxadiazol-5-yl)-26,27-cyclo-9,10-secocholesta-5,7,10(19),22-tetraene-1,3,24-triol (5Z,7E,22E)-(1S,3R,24S)-25-(3-ethyl-1,2,4-oxadiazol-5-yl)-26,27-cyclo-9,10-secocholesta-5,7,10(19),22-tetraene-1,3,24-triol (5Z,7E,22E)-(1S,3R,24R)-25-(3-propyl-1,2,4-oxadiazol-5-yl)-26,27-cyclo-9,10-secocholesta-5,7,10(19),22-tetraene-1,3,24-triol (5Z,7E,22E)-(1S,3R,24S)-25-(3-propyl-1,2,4-oxadiazol-5-yl)-26,27-cyclo-9,10-secocholesta-5,7,10(19),22-tetraene-1,3,24-triol (5Z,7E,22E)-(1S,3R,24R)-25-(3-butyl-1,2,4-oxadiazol-5-yl)-26,27-cyclo-9,10-secocholesta-5,7,10(19),22-tetraene-1,3,24-triol (5Z,7E,22E)-(1S,3R,24S)-25-(3-butyl-1,2,4-oxadiazol-5-yl)-26,27-cyclo-9,10-secocholesta-5,7,10(19),22-tetraene-1,3,24-triol (5Z,7E,22E)-(1S,3R,24R)-25-(3-pentyl-1,2,4-oxadiazol-5-yl)-26,27-cyclo-9,10-secocholesta-5,7,10(19),22-tetraene-1,3,24-triol (5Z,7E,22E)-(1S,3R,24S)-25-(3-pentyl-1,2,4-oxadiazol-5-yl)-26,27-cyclo-9,10-secocholesta-5,7,10(19),22-tetraene-1,3,24-triol (5Z,7E,22E)-(1S,3R,24R)-25-(5-methyl-1,3,4-oxadiazol-2-yl)-26,27-cyclo-9,10-secocholesta-5,7,10(19),22-tetraene-1,3,24-triol (5Z,7E,22E)-(1S,3R,24S)-25-(5-methyl-1,3,4-oxadiazol-2-yl)-26,27-cyclo-9,10-secocholesta-5,7,10(19),22-tetraene-1,3,24-triol (5Z,7E,22E)-(1S,3R,24R)-25-(5-ethyl-1,3,4-oxadiazol-2-yl)-26,27-cyclo-9,10-secocholesta-5,7,10(19),22-tetraene-1,3,24-triol (5Z,7E,22E)-(1S,3R,24S)-25-(5-ethyl-1,3,4-oxadiazol-2-yl)-26,27-cyclo-9,10-secocholesta-5,7,10(19),22-tetraene-1,3,24-triol (5Z,7E,22E)-(1S,3R,24R)-25-(5-propyl-1,3,4-oxadiazol-2-yl)-26,27-cyclo-9,10-secocholesta-5,7,10(19),22-tetraene-1,3,24-triol (5Z,7E,22E)-(1S,3R,24S)-25-(5-propyl-1,3,4-oxadiazol-2-yl)-26,27-cyclo-9,10-secocholesta-5,7,10(19),22-tetraene-1,3,24-triol (5Z,7E,22E)-(1S,3R,24R)-25-(5-butyl-1,3,4-oxadiazol-2-yl)-26,27-cyclo-9,10-secocholesta-5,7,10(19),22-tetraene-1,3,24-triol (5Z,7E,22E)-(1S,3R,24S)-25-(5-butyl-1,3,4-oxadiazol-2-yl)-26,27-cyclo-9,10-secocholesta-5,7,10(19),22-tetraene-1,3,24-triol (5Z,7E,22E)-(1S,3R,24R)-25-(5-pentyl-1,3,4-oxadiazol-2-yl)-26,27-cyclo-9,10-secocholesta-5,7,10(19),22-tetraene-1,3,24-triol (5Z,7E,22E)-(1S,3R,24S)-25-(5-pentyl-1,3,4-oxadiazol-2-yl)-26,27-cyclo-9,10-secocholesta-5,7,10(19),22-tetraene-1,3,24-triol (5Z,7E,22E)-(1S,3R,24R)-25-phenyl-26,27-cyclo-9,10-secocholesta-5,7,10(19),22-tetraene-1,3,24-triol (5Z,7E,22E)-(1S,3R,24S)-25-phenyl-26,27-cyclo-9,10-secocholesta-5,7,10(19),22-tetraene-1,3,24-triol (5Z,7E,22E)-(1S,3R,24R)-25-(4-methylphenyl)-26,27-cyclo-9,10-secocholesta-5,7,10(19),22-tetraene-1,3,24-triol (5Z,7E,22E)-(1S,3R,24S)-25-(4-methylphenyl)-26,27-cyclo-9,10-secocholesta-5,7,10(19),22-tetraene-1,3,24-triol (5Z,7E,22E)-(1S,3R,24R)-25-(4-ethylphenyl)-26,27-cyclo-9,10-secocholesta-5,7,10(19),22-tetraene-1,3,24-triol (5Z,7E,22E)-(1S,3R,24S)-25-(4-ethylphenyl)-26,27-cyclo-9,10-secocholesta-5,7,10(19),22-tetraene-1,3,24-triol (5Z,7E,22E)-(1S,3R,24R)-25-(4-propylphenyl)-26,27-cyclo-9,10-secocholesta-5,7,10(19),22-tetraene-1,3,24-triol (5Z,7E,22E)-(1S,3R,24S)-25-(4-propylphenyl)-26,27-cyclo-9,10-secocholesta-5,7,10(19),22-tetraene-1,3,24-triol (5Z,7E,22E)-(1S,3R,24R)-25-(4-butylphenyl)-26,27-cyclo-9,10-secocholesta-5,7,10(19),22-tetraene-1,3,24-triol (5Z,7E,22E)-(1S,3R,24S)-25-(4-butylphenyl)-26,27-cyclo-9,10-secocholesta-5,7,10(19),22-tetraene-1,3,24-triol (5Z,7E,22E)-(1S,3R,24R)-25-(4-pentylphenyl)-26,27-cyclo-9,10-secocholesta-5,7,10(19),22-tetraene-1,3,24-triol (5Z,7E,22E)-(1S,3R,24S)-25-(4-pentylphenyl)-26,27-cyclo-9,10-secocholesta-5,7,10(19),22-tetraene-1,3,24-triol (5Z,7E,22E)-(1S,3R,24R)-25-(3-methylphenyl)-26,27-cyclo-9,10-secocholesta-5,7,10(19),22-tetraene-1,3,24-triol (5Z,7E,22E)-(1S,3R,24S)-25-(3-methylphenyl)-26,27-cyclo-9,10-secocholesta-5,7,10(19),22-tetraene-1,3,24-triol (5Z,7E,22E)-(1S,3R,24R)-25-(3-ethylphenyl)-26,27-cyclo-9,10-secocholesta-5,7,10(19),22-tetraene-1,3,24-triol (5Z,7E,22E)-(1S,3R,24S)-25-(3-ethylphenyl)-26,27-cyclo-9,10-secocholesta-5,7,10(19),22-tetraene-1,3,24-triol (5Z,7E,22E)-(1S,3R,24R)-25-(3-propylphenyl)-26,27-cyclo-9,10-secocholesta-5,7,10(19),22-tetraene-1,3,24-triol (5Z,7E,22E)-(1S,3R,24S)-25-(3-propylphenyl)-26,27-cyclo-9,10-secocholesta-5,7,10(19),22-tetraene-1,3,24-triol (5Z,7E,22E)-(1S,3R,24R)-25-(3-butylphenyl)-26,27-cyclo-9,10-secocholesta-5,7,10(19),22-tetraene-1,3,24-triol (5Z,7E,22E)-(1S,3R,24S)-25-(3-butylphenyl)-26,27-cyclo-9,10-secocholesta-5,7,10(19),22-tetraene-1,3,24-triol (5Z,7E,22E)-(1S,3R,24R)-25-(3-pentylphenyl)-26,27-cyclo-9,10-secocholesta-5,7,10(19),22-tetraene-1,3,24-triol (5Z,7E,22E)-(1S,3R,24S)-25-(3-pentylphenyl)-26,27-cyclo-9,10-secocholesta-5,7,10(19),22-tetraene-1,3,24-triol (5Z,7E,22E)-(1S,3R,24R)-25-[4-(1-methylethyl)phenyl)-26,27-cyclo-9,10-secocholesta-5,7,10(19),22-tetraene-1,3,24-triol (5Z,7E,22E)-(1S,3R,24S)-25-[4-(1-methylethyl)phenyl)-26,27-cyclo-9,10-secocholesta-5,7,10(19),22-tetraene-1,3,24-triol (5Z,7E,22E)-(1S,3R,24R)-25-[3-(1-methylethyl)phenyl)-26,27-cyclo-9,10-secocholesta-5,7,10(19),22-tetraene-1,3,24-triol (5Z,7E,22E)-(1S,3R,24S)-25-[3-(1-methylethyl)phenyl)-26,27-cyclo-9,10-secocholesta-5,7,10(19),22-tetraene-1,3,24-triol (5Z,7E,22E)-(1S,3R,24R)-25-(2-pyridyl)-26,27-cyclo-9,10-secocholesta-5,7,10(19),22-tetraene-1,3,24-triol (5Z,7E,22E)-(1S,3R,24S)-25-(2-pyridyl)-26,27-cyclo-9,10-secocholesta-5,7,10(19),22-tetraene-1,3,24-triol (5Z,7E,22E)-(1S,3R,24R)-25-(6-methyl-2-pyridyl)-26,27-cyclo-9,10-secocholesta-5,7,10(19),22-tetraene-1,3,24-triol (5Z,7E,22E)-(1S,3R,24S)-25-(6-methyl-2-pyridyl)-26,27-cyclo-9,10-secocholesta-5,7,10(19),22-tetraene-1,3,24-triol (5Z,7E,22E)-(1S,3R,24R)-25-(5-methyl-2-pyridyl)-26,27-cyclo-9,10-secocholesta-5,7,10(19),22-tetraene-1,3,24-triol (5Z,7E,22E)-(1S,3R,24S)-25-(5-methyl-2-pyridyl)-26,27-cyclo-9,10-secocholesta-5,7,10(19),22-tetraene-1,3,24-triol (5Z,7E,22E)-(1S,3R,24R)-25-(4-methyl-2-pyridyl)-26,27-cyclo-9,10-secocholesta-5,7,10(19),22-tetraene-1,3,24-triol (5Z,7E,22E)-(1S,3R,24S)-25-(4-methyl-2-pyridyl)-26,27-cyclo-9,10-secocholesta-5,7,10(19),22-tetraene-1,3,24-triol (5Z,7E,22E)-(1S,3R,24R)-25-(6-ethyl-2-pyridyl)-26,27-cyclo-9,10-secocholesta-5,7,10(19),22-tetraene-1,3,24-triol (5Z,7E,22E)-(1S,3R,24S)-25-(6-ethyl-2-pyridyl)-26,27-cyclo-9,10-secocholesta-5,7,10(19),22-tetraene-1,3,24-triol (5Z,7E,22E)-(1S,3R,24R)-25-(5-ethyl-2-pyridyl)-26,27-cyclo-9,10-secocholesta-5,7,10(19),22-tetraene-1,3,24-triol (5Z,7E,22E)-(1S,3R,24S)-25-(5-ethyl-2-pyridyl)-26,27-cyclo-9,10-secocholesta-5,7,10(19),22-tetraene-1,3,24-triol (5Z,7E,22E)-(1S,3R,24R)-25-(4-ethyl-2-pyridyl)-26,27-cyclo-9,10-secocholesta-5,7,10(19),22-tetraene-1,3,24-triol (5Z,7E,22E)-(1S,3R,24S)-25-(4-ethyl-2-pyridyl)-26,27-cyclo-9,10-secocholesta-5,7,10(19),22-tetraene-1,3,24-triol (5Z,7E,22E)-(1S,3R,24R)-25-(6-propyl-2-pyridyl)-26,27-cyclo-9,10-secocholesta-5,7,10(19),22-tetraene-1,3,24-triol (5Z,7E,22E)-(1S,3R,24S)-25-(6-propyl-2-pyridyl)-26,27-cyclo-9,10-secocholesta-5,7,10(19),22-tetraene-1,3,24-triol (5Z,7E,22E)-(1S,3R,24R)-25-(5-propyl-2-pyridyl)-26,27-cyclo-9,10-secocholesta-5,7,10(19),22-tetraene-1,3,24-triol (5Z,7E,22E)-(1S,3R,24S)-25-(5-propyl-2-pyridyl)-26,27-cyclo-9,10-secocholesta-5,7,10(19),22-tetraene-1,3,24-triol (5Z,7E,22E)-(1S,3R,24R)-25-(4-propyl-2-pyridyl)-26,27-cyclo-9,10-secocholesta-5,7,10(19),22-tetraene-1,3,24-triol (5Z,7E,22E)-(1S,3R,24S)-25-(4-propyl-2-pyridyl)-26,27-cyclo-9,10-secocholesta-5,7,10(19),22-tetraene-1,3,24-triol (5Z,7E,22E)-(1S,3R,24R)-25-(6-butyl-2-pyridyl)-26,27-cyclo-9,10-secocholesta-5,7,10(19),22-tetraene-1,3,24-triol (5Z,7E,22E)-(1S,3R,24S)-25-(6-butyl-2-pyridyl)-26,27-cyclo-9,10-secocholesta-5,7,10(19),22-tetraene-1,3,24-triol (5Z,7E,22E)-(1S,3R,24R)-25-(5-butyl-2-pyridyl)-26,27-cyclo-9,10-secocholesta-5,7,10(19),22-tetraene-1,3,24-triol (5Z,7E,22E)-(1S,3R,24S)-25-(5-butyl-2-pyridyl)-26,27-cyclo-9,10-secocholesta-5,7,10(19),22-tetraene-1,3,24-triol (5Z,7E,22E)-(1S,3R,24R)-25-(4-butyl-2-pyridyl)-26,27-cyclo-9,10-secocholesta-5,7,10(19),22-tetraene-1,3,24-triol (5Z,7E,22E)-(1S,3R,24S)-25-(4-butyl-2-pyridyl)-26,27-cyclo-9,10-secocholesta-5,7,10(19),22-tetraene-1,3,24-triol (5Z,7E,22E)-(1S,3R,24R)-25-(5,5-dimethyl-2-oxazolin-2-yl)-26,27-cyclo-9,10-secocholesta-5,7,10(19),22-tetraene-1,3,24-triol (5Z,7E,22E)-(1S,3R,24S)-25-(5,5-dimethyl-2-oxazolin-2-
yl)-26,27-cyclo-9,10-secocholesta-5,7,10(19),22-
tetraene-1,3,24-triol
(5Z,7E,22E)-(1S,3R,24R)-25-(5,5-diethyl-2-oxazolin-2-yl)-
26,27-cyclo-9,10-secocholesta-5,7,10(19),22-tetraene-1,
3,24-triol
(5Z,7E,22E)-(1S,3R,24S)-25-(5,5-diethyl-2-oxazolin-2-yl)-
26,27-cyclo-9,10-secocholesta-5,7,10(19),22-tetraene-1,
3,24-triol
(5Z,7E,22E)-[1S,3R,24R,25(R)]-25-(5-methyl-2-oxazolin-
2-yl)-26,27-cyclo-9,10-secocholesta-5,7,10(19),22-
tetraene-1,3,24-triol
(5Z,7E,22E)-[1S,3R,24S,25(R)]-25-(5-methyl-2-oxazolin-
2-yl)-26,27-cyclo-9,10-secocholesta-5,7,10(19),22-
tetraene-1,3,24-triol
(5Z,7E,22E)-[1S,3R,24R,25(S)]-25-(5-methyl-2-oxazolin-
2-yl)-26,27-cyclo-9,10-secocholesta-5,7,10(19),22-
tetraene-1,3,24-triol
(5Z,7E,22E)-[1S,3R,24S,25(S)]-25-(5-methyl-2-oxazolin-
2-yl)-26,27-cyclo-9,10-secocholesta-5,7,10(19),22-
tetraene-1,3,24-triol
(5Z,7E,22E)-[1S,3R,24R,25(R)]-25-(5-ethyl-2-oxazolin-2-
yl)-26,27-cyclo-9,10-secocholesta-5,7,10(19),22-
tetraene-1,3,24-triol
(5Z,7E,22E)-[1S,3R,24S,25(R)]-25-(5-ethyl-2-oxazolin-2-
yl)-26,27-cyclo-9,10-secocholesta-5,7,10(19),22-
tetraene-1,3,24-triol
(5Z,7E,22E)-[1S,3R,24R,25(S)]-25-(5-ethyl-2-oxazolin-2-
yl)-26,27-cyclo-9,10-secocholesta-5,7,10(19),22-
tetraene-1,3,24-triol
(5Z,7E,22E)-[1S,3R,24S,25(S)]-25-(5-ethyl-2-oxazolin-2-
yl)-26,27-cyclo-9,10-secocholesta-5,7,10(19),22-
tetraene-1,3,24-triol
(5Z,7E,22E)-[1S,3R,24R,25(R)]-25-(5-propyl-2-oxazolin-
2-yl)-26,27-cyclo-9,10-secocholesta-5,7,10(19),22-
tetraene-1,3,24-triol
(5Z,7E,22E)-[1S,3R,24S,25(R)]-25-(5-propyl-2-oxazolin-
2-yl)-26,27-cyclo-9,10-secocholesta-5,7,10(19),22-
tetraene-1,3,24-triol
(5Z,7E,22E)-[1S,3R,24R,25(S)]-25-(5-propyl-2-oxazolin-
2-yl)-26,27-cyclo-9,10-secocholesta-5,7,10(19),22-
tetraene-1,3,24-triol
(5Z,7E,22E)-[1S,3R,24S,25(S)]-25-(5-propyl-2-oxazolin-2-
yl)-26,27-cyclo-9,10-secocholesta-5,7,10(19),22-
tetraene-1,3,24-triol
(5Z,7E,22E)-[1S,3R,24R,25(R)]-25-(5-butyl-2-oxazolin-2-
yl)-26,27-cyclo-9,10-secocholesta-5,7,10(19),22-
tetraene-1,3,24-triol
(5Z,7E,22E)-[1S,3R,24S,25(R)]-25-(5-butyl-2-oxazolin-2-
yl)-26,27-cyclo-9,10-secocholesta-5,7,10(19),22-
tetraene-1,3,24-triol
(5Z,7E,22E)-[1S,3R,24R,25(S)]-25-(5-butyl-2-oxazolin-2-
yl)-26,27-cyclo-9,10-secocholesta-5,7,10(19),22-
tetraene-1,3,24-triol
(5Z,7E,22E)-[1S,3R,24S,25(S)]-25-(5-butyl-2-oxazolin-2-
yl)-26,27-cyclo-9,10-secocholesta-5,7,10(19),22-
tetraene-1,3,24-triol
(5Z,7E,22E)-[1S,3R,24R,25(R)]-25-(5-phenyl-2-oxazolin-
2-yl)-26,27-cyclo-9,10-secocholesta-5,7,10(19),22-
tetraene-1,3,24-triol
(5Z,7E,22E)-[1S,3R,24S,25(R)]-25-(5-phenyl-2-oxazolin-
2-yl)-26,27-cyclo-9,10-secocholesta-5,7,10(19),22-
tetraene-1,3,24-triol
(5Z,7E,22E)-[1S,3R,24R,25(S)]-25-(5-phenyl-2-oxazolin-
2-yl)-26,27-cyclo-9,10-secocholesta-5,7,10(19),22-
tetraene-1,3,24-triol
(5Z,7E,22E)-[1S,3R,24S,25(S)]-25-(5-phenyl-2-oxazolin-
2-yl)-26,27-cyclo-9,10-secocholesta-5,7,10(19),22-
tetraene-1,3,24-triol
(5Z,7E,22E)-(1S,3R,20S,24R)-25-(5-propyloxazol-2-yl)-
26,27-cyclo-9,10-secocholesta-5,7,10(19),22-tetraene-1,
3,24-triol
(5Z,7E,22E)-(1S,3R,20S,24S)-25-(5-propyloxazol-2-yl)-
26,27-cyclo-9,10-secocholesta-5,7,10(19),22-tetraene-1,
3,24-triol
(5Z,7E,22E)-(1S,3R,20S,24R)-25-(5-methyloxazol-2-yl)-
26,27-cyclo-9,10-secocholesta-5,7,10(19),22-tetraene-1,
3,24-triol
(5Z,7E,22E)-(1S,3R,20S,24S)-25-(5-methyloxazol-2-yl)-
26,27-cyclo-9,10-secocholesta-5,7,10(19),22-tetraene-1,
3,24-triol
(5Z,7E,22E)-(1S,-3R,20S,24R)-25-(5-ethyloxazol-2-yl)-26,
27-cyclo-9,10-secocholesta-5,7,10(19),22-tetraene-1,3,
24-triol
(5Z,7E,22E)-(1S,3R,20S,24S)-25-(5-ethyloxazol-2-yl)-26,
27-cyclo-9,10-secocholesta-5,7,10(19),22-tetraene-1,3,
24-triol
(5Z,7E,22E)-(1S,3R,20S,24R)-25-(5-butyloxazol-2-yl)-26,
27-cyclo-9,10-secocholesta-5,7,10(19),22-tetraene-1,3,
24-triol
(5Z,7E,22E)-(1S,3R,20S,24S)-25-(5-butyloxazol-2-yl)-26,
27-cyclo-9,10-secocholesta-5,7,10(19),22-tetraene-1,3,
24-triol
(5Z,7E,22E)-(1S,3R,20S,24R)-25-(5-pentyloxazol-2-yl)-
26,27-cyclo-9,10-secocholesta-5,7,10(19),22-tetraene-1,
3,24-triol
(5Z,7E,22E)-(1S,3R,20S,24S)-25-(5-pentyloxazol-2-yl)-26,
27-cyclo-9,10-secocholesta-5,7,10(19),22-tetraene-1,3,
24-triol
(5Z,7E,22E)-(1S,3R,20S,24R)-25-(5-propylthiazol-2-yl)-
26,27-cyclo-9,10-secocholesta-5,7,10(19),22-tetraene-1,
3,24-triol
(5Z,7E,22E)-(1S,3R,20S,24S)-25-(5-propylthiazol-2-yl)-
26,27-cyclo-9,10-secocholesta-5,7,10(19),22-tetraene-1,
3,24-triol
(5Z,7E,22E)-(1S,3R,20S,24R)-25-(5-methylthiazol-2-yl)-
26,27-cyclo-9,10-secocholesta-5,7,10(19),22-tetraene-1,
3,24-triol
(5Z,7E,22E)-(1S,3R,20S,24S)-25-(5-methylthiazol-2-yl)-
26,27-cyclo-9,10-secocholesta-5,7,10(19),22-tetraene-1,
3,24-triol
(5Z,7E,22E)-(1S,3R,20S,24R)-25-(5-ethylthiazol-2-yl)-26,
27-cyclo-9,10-secocholesta-5,7,10(19),22-tetraene-1,3,
24-triol
(5Z,7E,22E)-(1S,3R,20S,24S)-25-(5-ethylthiazol-2-yl)-26,
27-cyclo-9,10-secocholesta-5,7,10(19),22-tetraene-1,3,
24-triol
(5Z,7E,22E)-(1S,3R,20S,24R)-25-(5-butylthiazol-2-yl)-26,
27-cyclo-9,10-secocholesta-5,7,10(19),22-tetraene-1,3,
24-triol
(5Z,7E,22E)-(1S,3R,20S,24S)-25-(5-butylthiazol-2-yl)-26,
27-cyclo-9,10-secocholesta-5,7,10(19),22-tetraene-1,3,
24-triol
(5Z,7E,22E)-(1S,3R,20S,24R)-25-(5-pentylthiazol-2-yl)-
26,27-cyclo-9,10-secocholesta-5,7,10(19),22-tetraene-1,
3,24-triol
(5Z,7E,22E)-(1S,3R,20S,24S)-25-(5-pentylthiazol-2-yl)-26,
27-cyclo-9,10-secocholesta-5,7,10(19),22-tetraene-1,3,
24-triol
(5Z,7E,22E)-(1S,3R,20S,24R)-25-(4-propyloxazol-2-yl)-
26,27-cyclo-9,10-secocholesta-5,7,10(19),22-tetraene-1,
3,24-triol
(5Z,7E,22E)-(1S,3R,20S,24S)-25-(4-propyloxazol-2-yl)-
26,27-cyclo-9,10-secocholesta-5,7,10(19),22-tetraene-1,
3,24-triol
(5Z,7E,22E)-(1S,3R,20S,24R)-25-(4-methyloxazol-2-yl)-
26,27-cyclo-9,10-secocholesta-5,7,10(19),22-tetraene-1,
3,24-triol (5Z,7E,22E)-(1S,3R,20S,24S)-25-(4-methyloxazol-2-yl)-26,27-cyclo-9,10-secocholesta-5,7,10(19),22-tetraene-1,3,24-triol (5Z,7E,22E)-(1S,3R,20S,24R)-25-(4-ethyloxazol-2-yl)-26,27-cyclo-9,10-secocholesta-5,7,10(19),22-tetraene-1,3,24-triol (5Z,7E,22E)-(1S,3R,20S,24S)-25-(4-ethyloxazol-2-yl)-26,27-cyclo-9,10-secocholesta-5,7,10(19),22-tetraene-1,3,24-triol (5Z,7E,22E)-(1S,3R,20S,24R)-25-(4-butyloxazol-2-yl)-26,27-cyclo-9,10-secocholesta-5,7,10(19),22-tetraene-1,3,24-triol (5Z,7E,22E)-(1S,3R,20S,24S)-25-(4-butyloxazol-2-yl)-26,27-cyclo-9,10-secocholesta-5,7,10(19),22-tetraene-1,3,24-triol (5Z,7E,22E)-(1S,3R,20S,24R)-25-(4-pentyloxazol-2-yl)-26,27-cyclo-9,10-secocholesta-5,7,10(19),22-tetraene-1,3,24-triol (5Z,7E,22E)-(1S,3R,20S,24S)-25-(4-pentyloxazol-2-yl)-26,27-cyclo-9,10-secocholesta-5,7,10(19),22-tetraene-1,3,24-triol (5Z,7E,22E)-(1S,3R,20S,24R)-25-(4-propylthiazol-2-yl)-26,27-cyclo-9,10-secocholesta-5,7,10(19),22-tetraene-1,3,24-triol (5Z,7E,22E)-(1S,3R,20S,24S)-25-(4-propylthiazol-2-yl)-26,27-cyclo-9,10-secocholesta-5,7,10(19),22-tetraene-1,3,24-triol (5Z,7E,22E)-(1S,3R,20S,24R)-25-(4-methylthiazol-2-yl)-26,27-cyclo-9,10-secocholesta-5,7,10(19),22-tetraene-1,3,24-triol (5Z,7E,22E)-(1S,3R,20S,24S)-25-(4-methylthiazol-2-yl)-26,27-cyclo-9,10-secocholesta-5,7,10(19),22-tetraene-1,3,24-triol (5Z,7E,22E)-(1S,3R,20S,24R)-25-(4-ethylthiazol-2-yl)-26,27-cyclo-9,10-secocholesta-5,7,10(19),22-tetraene-1,3,24-triol (5Z,7E,22E)-(1S,3R,20S,24S)-25-(4-ethylthiazol-2-yl)-26,27-cyclo-9,10-secocholesta-5,7,10(19),22-tetraene-1,3,24-triol (5Z,7E,22E)-(1S,3R,20S,24R)-25-(4-butylthiazol-2-yl)-26,27-cyclo-9,10-secocholesta-5,7,10(19),22-tetraene-1,3,24-triol (5Z,7E,22E)-(1S,3R,20S,24S)-25-(4-butylthiazol-2-yl)-26,27-cyclo-9,10-secocholesta-5,7,10(19),22-tetraene-1,3,24-triol (5Z,7E,22E)-(1S,3R,20S,24R)-25-(4-pentylthiazol-2-yl)-26,27-cyclo-9,10-secocholesta-5,7,10(19),22-tetraene-1,3,24-triol (5Z,7E,22E)-(1S,3R,20S,24S)-25-(4-pentylthiazol-2-yl)-26,27-cyclo-9,10-secocholesta-5,7,10(19),22-tetraene-1,3,24-triol (5Z,7E,22E)-(1S,3R,24R)-20-methyl-25-(5-propyloxazol-2-yl)-26,27-cyclo-9,10-secocholesta-5,7,10(19),22-tetraene-1,3,24-triol (5Z,7E,22E)-(1S,3R,24S)-20-methyl-25-(5-propyloxazol-2-yl)-26,27-cyclo-9,10-secocholesta-5,7,10(19),22-tetraene-1,3,24-triol (5Z,7E,22E)-(1S,3R,24R)-20-methyl-25-(5-methyloxazol-2-yl)-26,27-cyclo-9,10-secocholesta-5,7,10(19),22-tetraene-1,3,24-triol (5Z,7E,22E)-(1S,3R,24S)-20-methyl-25-(5-methyloxazol-2-yl)-26,27-cyclo-9,10-secocholesta-5,7,10(19),22-tetraene-1,3,24-triol (5Z,7E,22E)-(1S,3R,24R)-25-(5-ethyloxazol-2-yl)-20-methyl-26,27-cyclo-9,10-secocholesta-5,7,10(19),22-tetraene-1,3,24-triol (5Z,7E,22E)-(1S,3R,24S)-25-(5-ethyloxazol-2-yl)-20-methyl-26,27-cyclo-9,10-secocholesta-5,7,10(19),22-tetraene-1,3,24-triol (5Z,7E,22E)-(1S,3R,24R)-25-(5-butyloxazol-2-yl)-20-methyl-26,27-cyclo-9,10-secocholesta-5,7,10(19),22-tetraene-1,3,24-triol (5Z,7E,22E)-(1S,3R,24S)-25-(5-butyloxazol-2-yl)-20-methyl-26,27-cyclo-9,10-secocholesta-5,7,10(19),22-tetraene-1,3,24-triol (5Z,7E,22E)-(1S,3R,24R)-20-methyl-25-(5-pentyloxazol-2-yl)-26,27-cyclo-9,10-secocholesta-5,7,10(19),22-tetraene-1,3,24-triol (5Z,7E,22E)-(1S,3R,24S)-20-methyl-25-(5-pentyloxazol-2-yl)-26,27-cyclo-9,10-secocholesta-5,7,10(19),22-tetraene-1,3,24-triol (5Z,7E,22E)-(1S,3R,24R)-20-methyl-25-(5-propylthiazol-2-yl)-26,27-cyclo-9,10-secocholesta-5,7,10(19),22-tetraene-1,3,24-triol (5Z,7E,22E)-(1S,3R,24S)-20-methyl-25-(5-propylthiazol-2-yl)-26,27-cyclo-9,10-secocholesta-5,7,10(19),22-tetraene-1,3,24-triol (5Z,7E,22E)-(1S,3R,24R)-20-methyl-25-(5-methylthiazol-2-yl)-26,27-cyclo-9,10-secocholesta-5,7,10(19),22-tetraene-1,3,24-triol (5Z,7E,22E)-(1S,3R,24S)-20-methyl-25-(5-methylthiazol-2-yl)-26,27-cyclo-9,10-secocholesta-5,7,10(19),22-tetraene-1,3,24-triol (5Z,7E,22E)-(1S,3R,24R)-25-(5-ethylthiazol-2-yl)-20-methyl-26,27-cyclo-9,10-secocholesta-5,7,10(19),22-tetraene-1,3,24-triol (5Z,7E,22E)-(1S,3R,24S)-25-(5-ethylthiazol-2-yl)-20-methyl-26,27-cyclo-9,10-secocholesta-5,7,10(19),22-tetraene-1,3,24-triol (5Z,7E,22E)-(1S,3R,24R)-25-(5-butylthiazol-2-yl)-20-methyl-26,27-cyclo-9,10-secocholesta-5,7,10(19),22-tetraene-1,3,24-triol (5Z,7E,22E)-(1S,3R,24S)-25-(5-butylthiazol-2-yl)-20-methyl-26,27-cyclo-9,10-secocholesta-5,7,10(19),22-tetraene-1,3,24-triol (5Z,7E,22E)-(1S,3R,24R)-25-(5-pentylthiazol-2-yl)-20-methyl-26,27-cyclo-9,10-secocholesta-5,7,10(19),22-tetraene-1,3,24-triol (5Z,7E,22E)-(1S,3R,24S)-25-(5-pentylthiazol-2-yl)-20-methyl-26,27-cyclo-9,10-secocholesta-5,7,10(19),22-tetraene-1,3,24-triol (5Z,7E,22E)-(1S,3R,24R)-20-methyl-25-(4-propyloxazol-2-yl)-26,27-cyclo-9,10-secocholesta-5,7,10(19),22-tetraene-1,3,24-triol (5Z,7E,22E)-(1S,3R,24S)-20-methyl-25-(4-propyloxazol-2-yl)-26,27-cyclo-9,10-secocholesta-5,7,10(19),22-tetraene-1,3,24-triol (5Z,7E,22E)-(1S,3R,24R)-20-methyl-25-(4-methyloxazol-2-yl)-26,27-cyclo-9,10-secocholesta-5,7,10(19),22-tetraene-1,3,24-triol (5Z,7E,22E)-(1S,3R,24S)-20-methyl-25-(4-methyloxazol-2-yl)-26,27-cyclo-9,10-secocholesta-5,7,10(19),22-tetraene-1,3,24-triol (5Z,7E,22E)-(1S,3R,24R)-25-(4-ethyloxazol-2-yl)-20-methyl-26,27-cyclo-9,10-secocholesta-5,7,10(19),22-tetraene-1,3,24-triol (5Z,7E,22E)-(1S,3R,24S)-25-(4-ethyloxazol-2-yl)-20-methyl-26,27-cyclo-9,10-secocholesta-5,7,10(19),22-tetraene-1,3,24-triol (5Z,7E,22E)-(1S,3R,24R)-25-(4-butyloxazol-2-yl)-20-methyl-26,27-cyclo-9,10-secocholesta-5,7,10(19),22-tetraene-1,3,24-triol (5Z,7E,22E)-(1S,3R,24S)-25-(4-butyloxazol-2-yl)-20-methyl-26,27-cyclo-9,10-secocholesta-5,7,10(19),22-tetraene-1,3,24-triol (5Z,7E,22E)-(1S,3R,24R)-20-methyl-25-(4-pentyloxazol-2-yl)-26,27-cyclo-9,10-secocholesta-5,7,10(19),22-tetraene-1,3,24-triol (5Z,7E,22E)-(1S,3R,24S)-20-methyl-25-(4-pentyloxazol-2-yl)-26,27-cyclo-9,10-secocholesta-5,7,10(19),22-tetraene-1,3,24-triol (5Z,7E,22E)-(1S,3R,24R)-20-methyl-25-(4-propylthiazol-2-yl)-26,27-cyclo-9,10-secocholesta-5,7,10(19),22-tetraene-1,3,24-triol (5Z,7E,22E)-(1S,3R,24S)-20-methyl-25-(4-propylthiazol-2-yl)-26,27-cyclo-9,10-secocholesta-5,7,10(19),22-tetraene-1,3,24-triol (5Z,7E,22E)-(1S,3R,24R)-20-methyl-25-(4-methylthiazol-2-yl)-26,27-cyclo-9,10-secocholesta-5,7,10(19),22-tetraene-1,3,24-triol (5Z,7E,22E)-(1S,3R,24S)-20-methyl-25-(4-methylthiazol-2-yl)-26,27-cyclo-9,10-secocholesta-5,7,10(19),22-tetraene-1,3,24-triol (5Z,7E,22E)-(1S,3R,24R)-25-(4-ethylthiazol-2-yl)-20-methyl-26,27-cyclo-9,10-secocholesta-5,7,10(19),22-tetraene-1,3,24-triol (5Z,7E,22E)-(1S,3R,24S)-25-(4-ethylthiazol-2-yl)-20-methyl-26,27-cyclo-9,10-secocholesta-5,7,10(19),22-tetraene-1,3,24-triol (5Z,7E,22E)-(1S,3R,24R)-25-(4-butylthiazol-2-yl)-20-methyl-26,27-cyclo-9,10-secocholesta-5,7,10(19),22-tetraene-1,3,24-triol (5Z,7E,22E)-(1S,3R,24S)-25-(4-butylthiazol-2-yl)-20-methyl-26,27-cyclo-9,10-secocholesta-5,7,10(19),22-tetraene-1,3,24-triol (5Z,7E,22E)-(1S,3R,24R)-25-(4-pentylthiazol-2-yl)-20-methyl-26,27-cyclo-9,10-secocholesta-5,7,10(19),22-tetraene-1,3,24-triol (5Z,7E,22E)-(1S,3R,24S)-25-(4-pentylthiazol-2-yl)-20-methyl-26,27-cyclo-9,10-secocholesta-5,7,10(19),22-tetraene-1,3,24-triol The natural vitamins $D_2$ and $D_3$ (cf. general formula of vitamin D) are inherently biologically inactive and are converted into biologically active metabolites [1α,25-dihydroxy vitamin $D_3$ (calcitriol) or -$D_2$] only after hydroxylation at C-atom 25 in the liver and at C-atom 1 in the kidney. The action of the active metabolites involves the regulation of the calcium and phosphate concentration in the serum; they counteract a dropping of the calcium concentration in the serum by increasing the calcium absorption in the intestine and under certain circumstances promoting calcium mobilization from the bones.

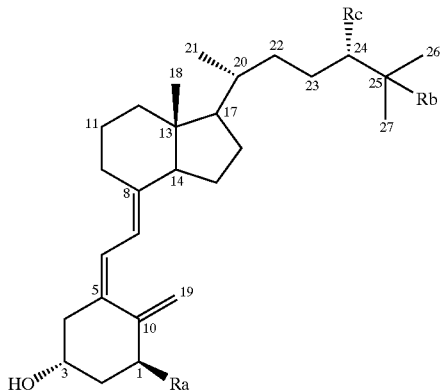

Ergocalciferol: Ra=Rb=H, Rc=$CH_3$ vitamin $D_2$ Double bond C-22/23
cholecalciferol: Ra=Rb=Rc=H vitamin $D_3$
25-hydroxycholecalciferol: Ra=Rc=H, Rb=OH
1α-hydroxycholecalciferol: Ra=OH, Rb=Rc=H
1α,25-dihydroxycholecalciferol: Ra=Rb=OH, Rc=H Calcitriol In addition to their pronounced effect on the calcium and phosphate metabolism, the active metabolites of vitamins $D_2$ and $D_3$ and their synthetic derivatives have a proliferation-inhibiting and differentiation-stimulating action on tumor cells and normal cells, such as, for example, skin cells. In addition, a pronounced effect on cells of the immune system (inhibiting of proliferation and interleukin 2-synthesis of lymphocytes, increase of cytotoxicity and phagocytosis in vitro of monocytes) has been found, which manifests itself in an immunomodulatory action, and finally, because of a stimulating action on bone-forming cells, an increased formation of bone in normal and osteoporotic rats is found [R. Bouillon et al. "Short Term Course of 1,25(OH)$_2$D$_3$ Stimulates Osteoblasts But Not Osteoclasts." Calc. Tissue Int. 49, 168–173 (1991)].

All actions are mediated by bonding to the vitamin D receptor. Because of the bonding, the activity of specific genes is regulated.

When using biologically active metabolites of vitamins $D_2$ and $D_3$, a toxic effect on the calcium metabolism is produced (hypercalcemia).

By structural manipulations of the side chain, therapeutically usable effectiveness can be separated from undesirable hypercalcemic activity. A suitable structural variant is the introduction of 24-hydroxy derivatives.

1α-Cholecalciferols that are hydroxylated in 24-position are already described in DE 25 26 981. They have a lower toxicity than the corresponding non-hydroxylated 1α-cholecalciferol. Further, 24-hydroxy derivatives are described in the following patent applications: DE 39 33 034, DE 40 03 854, DE 40 34 730, EP 0 421 561, EP 0 441 467, WO 91/12238.

Finally, 25-carboxylic acid derivatives of calcitriol that are hydroxylated at C-24 are described in WO 94/07853, which exhibit a more advantageous spectrum of action than calcitriol. While the ability to trigger a hypercalcemia is considerably weakened, the proliferation-inhibiting and differentiation-stimulating actions are maintained.

Relative to these structurally allied compounds, the substances according to the invention are distinguished in that they show a greater effect on cell differentiation, whereby the effect on the calcium balance does not increase. Other substances according to the invention, however, exhibit an antagonistic profile of action that can make new applications possible.

The vitamin D activity of the substances according to the invention is determined with the aid of the calcitriol-receptor test. It is carried out using a specific receptor protein from the intestines of juvenile pigs.

Receptor-containing binding protein is incubated in a test tube with $^3$H-calcitriol ($5\times10^{-10}$ mol/l) in a reaction volume of 0.270 ml in the absence and in the presence of test substances for two hours at 4° C. To separate free and receptor-bound calcitriol, a charcoal-dextran absorption is carried out. 250 μl of a charcoal-dextran suspension is fed to each test tube and incubated at 4° C. for 20 minutes. Then, the samples are centrifuged at 10,000×g for 5 minutes at 4° C. The supernatant is decanted and measured in a β-counter after 1 hour of equilibration in Picofluor 15™.

The competition curves that are obtained with various concentrations of test substance as well as of reference substance (unlabeled calcitriol) at constant concentration of the reference substance ($^3$H-calcitriol) are placed in relation to one another, and a competition factor (KF) is determined.

It is defined as a quotient of the concentrations of the respective test substance and the reference substance, which are necessary for 50% competition:

KF=Concentration of test substance at 50% competition/ Concentration of reference substance at 50% competition It is common to the compounds according to the invention that they all have a considerable affinity to the calcitriol receptor.

To determine the acute hypercalcemic action of various calcitriol derivatives, the test that is described below is carried out:

The action of control (solution base), reference substance (1,25(OH)$_2$-D$_3$=calcitriol) and test substance is tested in each case after one-time subcutaneous administration in groups of 10 healthy male rats (140–170 g). During the testing time, the rats are kept in special cages to determine the excretion of water and mineral substances. Urine is collected in 2 fractions (0–16 hours and 16–22 hours). An oral dose of calcium (0.1 mmol of calcium in 6.5% alpha-hydroxypropylcellulose, 5 ml/animal) replaces at 1600 hours the calcium intake that is lacking by food deprivation. At the end of the test, the animals are killed by decapitation and exsanguinated to determine the serum-calcium values. For the primary screen test in vivo, an individual standard dose (200 μg/kg) is tested. For selected substances, the result is supported by establishing a dose-effect relation.

A hypercalcemic action is shown in serum-calcium level values that are higher than in the control.

The significance of differences between substance groups and controls and between test substance and reference substance are supported with suitable statistical processes. The result is indicated as dose ratio DR (DR=factor of test substance dose/reference substance dose for comparable actions).

The differentiation-stimulating action of calcitriol analogues is also detected quantitatively.

It is known in the literature [Mangelsdorf, D. J. et al., J. Cell. Biol. 98: 391 (1984)], that the treatment of human leukemia cells (promyelocyte cell line HL 60) in vitro with calcitriol induces the differentiation of cells to macrophages.

HL 60 cells are cultivated in tissue culture medium (RPMI 10% fetal calf serum) at 37° C. in an atmosphere of 5% $CO_2$ in air.

For substance testing, the cells are centrifuged off, and 2.0×10$^5$ cells/ml in phenol red-free tissue culture medium is taken up. The test substances are dissolved in ethanol and diluted with tissue culture medium without phenol red to the desired concentration. The dilution stages are mixed with the cell suspension at a ratio of 1:10, and 100 μl each of this cell suspension that is mixed with substance is pipetted into an indentation of a 96-hole plate. For control, a cell suspension is mixed analogously with the solvent.

After incubation for 96 hours at 37° C. in 5% $CO_2$ in air, 100 μl of an NBT-TPA solution (nitro blue tetrazolium (NBT), final concentration in the batch of 1 mg/ml, tetradecanoyl phorbolmyristate-13-acetate (TPA), final concentration in the batch of 2×10$^{-7}$ mol/l) is pipetted into each indentation of the 96-hole plate in the cell suspension.

By incubation for 2 hours at 37° C. and 5% $CO_2$ in air, NBT is reduced to insoluble formazan because of the intracellular oxygen radical release, stimulated by TPA, in the cells that are differentiated to macrophages.

To complete the reaction, the indentations of the 96-hole plate are suctioned off, and the cells are affixed to the bottom of the plate by adding methanol and dried after affixing. To dissolve the intracellular formazan crystals that are formed, 100 μl of potassium hydroxide (2 mol/l) and 100 μl of dimethyl sulfoxide are pipetted into each indentation and ultrasonically treated for 1 minute. The concentration of formazan is measured by spectrophotometry at 650 nm.

As a yardstick for the differentiation induction of HL 60 cells to macrophages, the concentration of formed formazan applies. The result is indicated as a dose ratio (DR=factor of test substance dose/reference substance dose for comparable semi-maximum actions).

The results of the calcitriol-receptor test and the determination of the dose ratio of the differentiation induction of HL 60 cells and the dose ratio for hypercalcemia are summarized below:

Test Compounds (5Z,7E,22E)-(1S,3R,24R)-25-(5-Propyloxazol-2-yl)-26,27-cyclo-9,10-secocholesta-5,7,10(19),22-tetraene-1,3,24-triol 14
(5Z,7E,22E)-(1S,3R,24R)-25-(5-methyloxazol-2-yl)-26,27-cyclo-9,10-secocholesta-5,7,10(19),22-tetraene-1,3,24-triol 15
(5Z,7E,22E)-(1S,3R,24R)-25-(5-ethyloxazol-2-yl)-26,27-cyclo-9,10-secocholesta-5,7,10(19),22-tetraene-1,3,24-triol 16
(5Z,7E,22E)-(1S,3R,24R)-25-(5-pentyloxazol-2-yl)-26,27-cyclo-9,10-secocholesta-5,7,10(19),22-tetraene-1,3,24-triol 17

Comparison Compound
Calcitriol

| Compound | Competition Factor KF for Receptor Bonding | Dose Ratio for Differentiation Induction in HL 60 Cells |
| --- | --- | --- |
| 14 | 2 | 1.9 |
| 15 | 2 | 3.4 |
| 16 | 3 | 1.3 |
| 17 | 4 | >100 |
| calcitriol | 1 | 1 |

In addition to an affinity to the vitamin D receptor, which is comparable to that of calcitriol, the compounds listed partially show a likewise comparable cell-differentiating activity.

The induction of a hypercalcemia is carried out, however, only at very much higher doses than in the case of calcitriol (dose ratio for 14=300; calcitriol DR=1).

By the reduced property of triggering a hypercalcemia, the substances according to the invention are suitable in a special way for the production of pharmaceutical agents for the treatment of diseases that are characterized by hyperproliferation and deficient cell differentiation. Included in these are, for example, hyperproliferative diseases of the skin (psoriasis, pityriasis subia pilasis, acne, ichthyosis) as well as tumor diseases and precancerous stages (for example, tumors of the intestines, carcinomas of the breast, lung tumors, prostate carcinomas, leukemias, T-cell lymphomas, melanomas, Batazell Larzin, squamous carcinoma, actinic keratoses, cervix dysplasias, and metastasizing tumors of any type).

Also, for the treatment and prophylaxis of diseases that are characterized by a disequilibrium of the immune system, the substances according to the invention are suitable. These include eczemas and diseases of the atopic Formon series, as well as auto-immune diseases, such as, for example, multiple scleroses, diabetes mellitus type I, myasthenia gravis, lupus erythematosus, scleroderma, bullous skin diseases (pemphigus, pemphigoid), further rejection reactions in the case of autologous, allogeneic or xenogeneic transplants, as well as AIDS. In all these diseases, the new compounds of general formula I can be combined advantageously with other substances that have an immunosuppressive action, such as cyclosporin A, FK 506, rapamycin and anti-CD 4 antibodies.

The substances are also suitable for therapy of secondary hyperparathyroidism and renal osteodystrophia because of the property of calcitriols to drop the parathormone synthesis.

Owing to the presence of the vitamin D receptor in the insulin-producing cells of the pancreas, the substances are suitable by increasing the insulin secretion for the therapy of diabetes mellitus type II.

Further, it has been found, surprisingly enough, that by topical application of the compounds according to the invention on the skin of mice, rats and guinea pigs, an increased reddening of the skin and increase of the thickness of the epidermis can be induced. The increase in the reddening of the skin is determined from the increase in the red value of the skin surface that can be quantified with a colorimeter. The red value is typically increased 1.5-fold after the substance (dose 0.003%) is administered three times at intervals of 24 hours. The increase of the thickness of the epidermis is quantified in the histological preparation. It is typically increased 2.5-fold. The number of proliferating epidermal cells (cells in the S-phase of the cell cycle) is determined by flow cytometry and is typically increased by a factor of 6.

These properties of the derivatives in the vitamin D series according to the invention can appear suitable for therapeutic use in the case of atrophic skin, as it occurs in natural skin aging because of increased light exposure or medicinally-induced skin atrophy by treatment with glucocorticoids.

Further, it can be assumed that wound healing can be accelerated by topical application with the new compounds.

In cell populations of the hair follicle, which contribute decisively to hair growth or to hair cycle regulation, it was possible to detect vitamin $D_3$ receptor proteins [Stumpf, W. E. et al., Cell Tissue Res. 238: 489 (1984); Milde, P. et al., J. Invest. Dermatol., 97: 230 (1991)]. In addition, in vitro findings on isolated hair follicle keratinocytes show a proliferation-inhibiting and differentiation-stimulating influence of 1,25-$(OH)_2$-$D_3$.

From clinical observations, it is known that the vitamin $D_3$-resistant rickets often accompanies alopecia, which develops in early infancy. Experimental findings show that the vitamin $D_3$ binding site of the VDR in this disease mutates, i.e., is defective (Kristjansson, K. et al., J. Clin. Invest. 92: 12, 1993)]. Keratinocytes, which were isolated from the hair follicles of these patients, do not react in vitro to the addition of 1,25-$(OH)_2$-$D_3$ [Arase, S. et al., J. Dermatol. Science 2: 353 (1991)].

These findings indicate a decisive role for 1,25-$(OH)_2$-D3 in the regulation of hair growth.

These analogues are therefore especially suitable for the production of pharmaceutical agents for the treatment of diseases which accompany disrupted hair growth (androgenetic alopecia, alopecia areata/totalis, chemotherapy-induced alopecia) or for supporting physiological hair growth.

Senile and postmenopausal osteoporosis is characterized by an increased bone turnover with an overall negative balance. Owing to the bone shrinkage especially of trabecular bones, fractures result to an increased extent. Owing to the stimulating action of calcitriol, both in the number and the conduct of synthesis of cells forming new bones (osteoblasts), the substances according to the invention are suitable for therapy and prophylaxis of senile and postmenopausal osteoporosis (EP 0 634 173 A1), of steroid-induced osteoporosis as well as for accelerated healing of arthroplasties. For the therapy of various forms of osteoporosis, they can be combined advantageously with estradiol or other derivatives of estrogen.

Finally, it was possible to show that calcitriol increases the synthesis of a growth substance for nerve cells (nerve growth factor) [M. S. Saporito et al. Brain Res. 633, 189 (1994)]. The compounds according to the invention are therefore also suitable for treating degenerative diseases of the peripheral and central nervous system, such as Alzheimer's disease and amyotrophic lateral sclerosis.

In addition, it has been found that certain compounds of general formula I in HL 60 cells antagonize, surprisingly enough, the action of calcitriol. In the series of 25-oxazole derivatives, the compounds with increasing chain length on the heterocycle in the case of constantly good receptor affinity show considerably weaker differentiation-stimulating agonistic activity in HL 60 cells (Tab. 1). Compounds 16 and 17 antagonize the action of calcitriol in HL 60 cells. This property is continued with increasing chain length in radical Z of general formula I.

Such compounds that antagonize the action of calcitriol can be used for the therapy of hypercalcemias, such as, for example, in hypervitaminosis D or intoxication with calcitriol and calcitriol-like active substances, or in the case of increased extrarenal calcitriol synthesis in granulomatous diseases (sarcoidosis, tuberculosis). Also, paraneoplastic hypercalcemias (for example, in osteolytic metastases and tumors with increased synthesis of parathormone-related peptides) as well as in hypercalcemias in hyperparathyroidism.

In addition, calcitriol antagonists can be used for birth control. In the reproductive tracts of female and male animals, the vitamin D receptor is expressed. It is known that the female and male fertility of vitamin-D-deficient animals is reduced. By short-term substitution of calcitriol, the reproductive output can be increased. Calcitriol antagonists are therefore able to influence female and male fertility.

Since calcitriol, under certain conditions, shows an immunosuppressive action, calcitriol receptor antagonists can also be used as immunostimulants, e.g., in the case of weak defenses against infections.

Calcitriol is known to be able to modulate hair growth. Calcitriol antagonists can therefore be used therapeutically in the case of undesirable hair growth, e.g., in hirsutism.

Vitamin D has long been known to play a stimulating role in the formation of arteriosclerotic plaque. In such vascular lesions, a calcitriol-regulated protein, osteopontin, is found to be increased, to which a role in vascular sclerosis is attributed (R. Eisenstein et al. Arch. Path. 77, 27 (1964), L. A. Fitzpatrick et al., J. Clin. Invest. 94, 1597 (1994)]. Calcitriol antagonists are therefore suitable for therapy and prophylaxis of all types. of arteriosclerosis.

Finally, calcitriol antagonists are suitable because of the property of calcitriol to increase unspecific immune reactions of monocytic cells, for therapy of inflammatory diseases, especially of a chronic nature, such as rheumatoid arthritis, Crohn's disease, ulcerative colitis, and granulomatous diseases such as sarcoidosis and other foreign-body reactions.

This invention thus relates to pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For topical use, the compounds are advantageously formulated as creams or ointments or in a similar form of pharmaceutical agent that is suitable for topical use. Each such formulation can also contain other pharmaceutically compatible and nontoxic adjuvants, such as, e.g., stabilizers, antioxidants, binders, dyes, emulsifiers or flavoring additives. The compounds are advantageously administered by injection or intravenous infusion of suitable sterile solutions or as oral dosage via the alimentary tract or topically in the form of creams, ointments, lotions or suitable transdermal patches, as is described in EP-A 0 387 077.

The daily dose is approximately 0.1 μg/patient/day–1000 μg (1 mg)/patient/day, preferably 1.0 μg/patient/day–500 μg/patient/day.

Vitamin D derivatives with substituents at C-25 are already described in Patent Application WO 97/00242 (Schering AG). In all cases, however, the substituent is linked by a carbonyl group, a hydroxymethyl group or a double bond to carbon atom 25. Under no circumstances did linkage of carbon atom directly to a carbo- or heterocycle occur. The synthesis methods described do not allow the creation of such substitution models, so that new processes had to be developed.

The production of the vitamin D derivatives of general formula I is carried out according to the invention from a compound of general formula II,

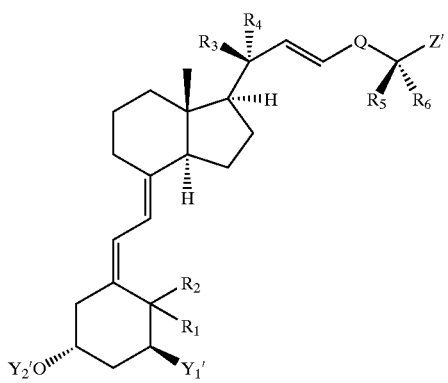

in which $Y'_1$ means a hydrogen atom or a protected hydroxyl group and $Y'_2$ means a hydroxy protective group.

Z' is distinguished from Z in that optionally present hydroxyl groups can be present in protected form.

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl (TIPS) groups or another standard hydroxy protective group (methoxymethyl, methoxyethoxymethyl, ethoxyethyl, tetrahydrofuranyl-tetrahydropryanl groups or see T. W. Greene, P. G. M. Wuts "Protective Groups in Organic Synthesis," 2$^{nd}$ Edition, John Wiley & Sons, 1991).

By simultaneous or successive cleavage of the hydroxy protective groups and optionally by partial, successive or complete esterification of the free hydroxyl groups, II is converted into a compound of general formula I.

In the case of the silyl protective groups or the trimethylsilylethoxymethyl group, tetrabutylammonium fluoride, hydrofluoric acid or hydrofluoric acid/pyridine is used for their cleavage; in the case of the ether groups (methoxymethyl, methoxyethoxymethyl, ethoxyethyl, tetrahydropyranylether), the latter are cleaved under catalytic action of acid, for example, p-toluenesulfonic acid, pyridinium-p-toluenesulfonate, acetic acid, hydrochloric acid, phosphoric acid or an acidic ion exchanger.

The esterification of the free hydroxy groups can be carried out according to standard processes with the corresponding carboxylic acid chlorides, bromides or anhydrides.

The production of the starting compounds for general formula II starts from various starting compounds depending on the ultimately desired substitution pattern in 10- and 20-position.

For the production of compounds of general formula II, in which $R_1$ and $R_2$ together mean an exocyclic methylene group, a start is made from known aldehyde III [M. Calverley Tetrahedron 43, 4609 (1987), WO 87/00834].

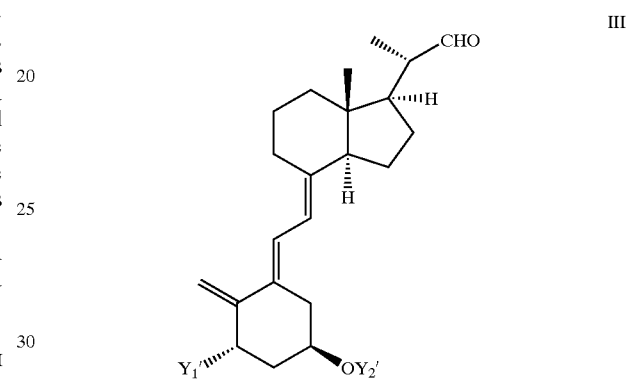

For $Y'_1$ and $Y'_2$, the already mentioned definitions apply. Protective groups other than those mentioned in the bibliographic references can be obtained by analogous procedure using correspondingly modified silyl chlorides (e.g., tert-butyldiphenylsilyl chloride instead of tert-butyldimethylsilyl chloride). By foregoing the corresponding stages for 1α-hydroxylation, derivatives of $Y'_1$=H type can be obtained.

The compounds of general formula III are now converted, analogously to known processes, into aldehydes of general formula IV [EP 647 219, WO 94/07853, M. J. Calverley, L. Binderup Bioorg. Med. Chem. Lett. 3, 1845–1848 (1993)].

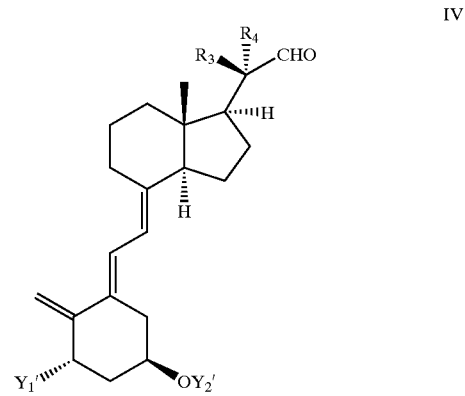

For $R_3$ and $R_4$, the definitions that are already mentioned above apply.

In creating the side chain, both compounds of general formula III and compounds of general formula IV can now be used.

Analogously to the established sequence (WO 94/07853), carboxylic acid amides of general formula V can thus be generated,

V

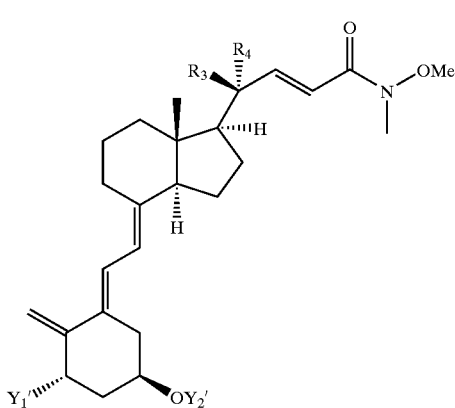

whereby for Y'$_1$, Y'$_2$, R$_3$ and R$_4$, the already given definitions apply.

To establish the natural vitamin D-triene system, a photochemical isomerization of the compounds of general formula V is performed. Irradiation with ultraviolet light is carried out in the presence of a so-called triplet sensitizer. Within the scope of this invention, anthracene is used in this respect. By cleavage of the π-bond of the 5,6-double bond, rotation of the A ring by 180° around the 5,6-single bond and reestablishing the 5,6-double bond, the stereoisomerism on the 5,6-double bond is reversed, whereby compounds of general formula VI accumulate,

VI

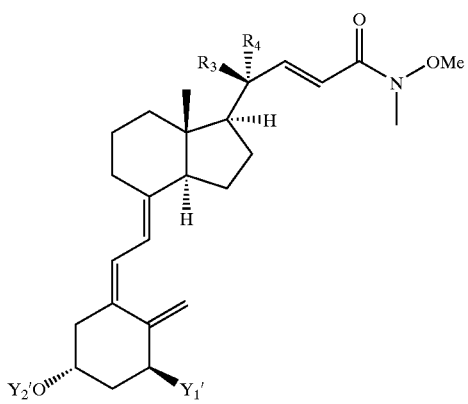

whereby Y'$_1$, Y'$_2$, R$_3$ and R$_4$ have the above-mentioned meanings. With a reducing agent (e.g., lithium aluminum hydride or diisobutylaluminum hydride), the amide group in the compound of general formula VI is reduced to aldehyde at low temperature (−60° C. to −100° C.) in a solvent such as tetrahydrofuran or another ether, whereby a compound of general formula VII accumulates,

VII

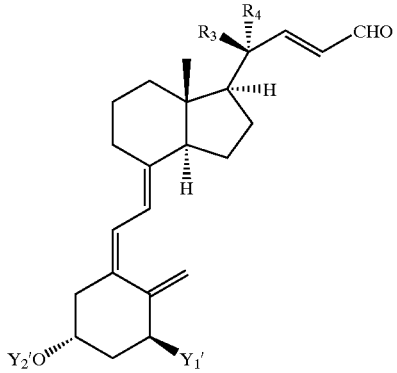

whereby radicals Y'$_1$, Y'$_2$, R$_3$ and R$_4$ have the already mentioned meanings.

The side chain now builds up further at the compound of general formula VII. By way of example, a description is given below of the use of the aldehyde of general formula VII for which the following is true: R$_3$=H and R$_4$=methyl. Correspondingly, however, the reaction possibilities below also apply for all other definitions for R$_3$ and R$_4$.

For synthesis of calcitriol derivatives with 26,27-cyclomodification, which, moreover, have oxazole substituents at C-25, the following synthesis method can be employed. Starting from 1-bromocyclopropanecarboxylic acid VIII [H. M. R. Hoffmann et al. J. Org. Chem. 54, 6096 (1989)], suitable side-chain fragments can be prepared.

VIII

The reaction with amino ketones or their hydrochlorides [M. Jackson et al., J. Am. Chem. Soc. 70, 2884 (1948), J. D. Hepworth Org. Synth. 45, 1 (1965)] of general formula IX first is carried out under condensation conditions (e.g., N,N'-dicyclohexylcarbodiimide, triethylamine),

IX

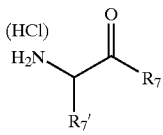

whereby R$_7$ and R'$_7$, independently of one another, mean a hydrogen atom, a straight-chain or branched, saturated or unsaturated alkyl radical with up to 12 carbon atoms, which can be interrupted at any points by oxa, thia or aza groups (substituted or unsubstituted) or sulfoxide or sulfo groups or can carry other substituents (free or protected hydroxy groups, halogen atoms). Derivatives of general formula X are thus produced.

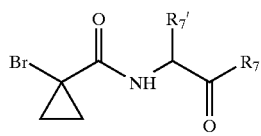

As an alternative, aminoalcohols or protected aminocarbonyl compounds can also be reacted with carboxylic acid VIII. The formation of derivatives of general formula X is then carried out by oxidation or protective group cleavage.

The formation of the oxazole ring can now be carried out under the effect of acid (e.g., sulfuric acid, phosphoric acid, polyphosphoric acid), whereby derivatives of general formula XI accumulate. Especially for the case $R_7$=H, gentler methods for oxazole formation are to be preferred [e.g., $PPh_3$, $NEt_3$, $I_2$ or $C_2Cl_6$, C. J. Moody et al. Synlett 825 (1996), W. Steglich et al. Lieb. Ann. 1916 (1978)].

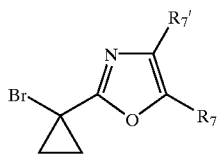

The creation of the side chain is now carried out by reaction of the cyclopropyl-metal compound that is generated by bromine-metal exchange from XI and vitamin D-C-24-aldehyde VII. The use of n-butyllithium or tert-butyllithium in hexane, diethyl ether, tetrahydrofuran or mixtures of these solvents is advantageous here at temperatures of between −100° C. and −50° C. Derivatives of general formula XII are thus obtained.

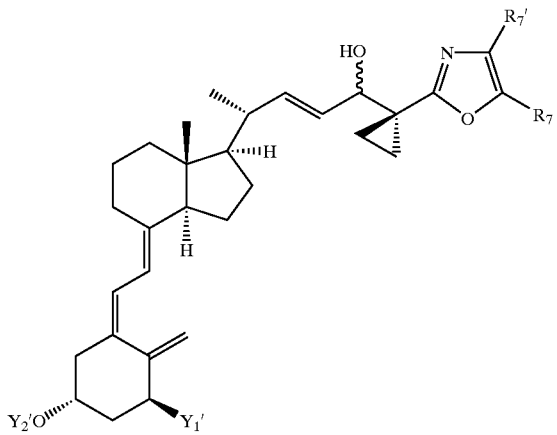

The latter can be regarded as a special case of general formula II, whose further reaction was already described and for which the following applies: Q is a hydroxymethylene group, $R_1$ and $R_2$ together form a methylene group, $R_5$ and $R_6$ together with carbon atom C-25 form a cyclopropyl ring, and Z' is an oxazole with substituents $R_7$ or $R'_7$, which has been defined previously.

The diastereomers can be separated relative to carbon atom C-24 chromatographically at this or a later stage.

A similar synthesis method can result in calcitriol derivatives that carry thiazole substituents at C-25. The derivative of general formula X must then be reacted in the presence of a sulfur reagent, such as, e.g., phosphorus pentasulfide, whereby thiazole derivatives of general formula XIII accumulate.

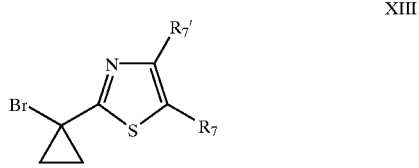

As an alternative, derivatives of general formula XIII for which $R_7$=hydrogen and $R'_7$ has the previously mentioned meaning could be obtained by reaction of corresponding amide VIII' to carboxylic acid VIII [H. M. R. Hoffmann et al. J. org. Chem. 54, 6096 (1989)]

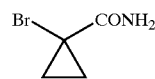

with 1-bromoketone ($BrCH_2$—CO—$R'_7$) in the presence of a sulfur reagent such as phosphorus pentasulfide (R. Kurkjy et al. J. Am. Chem. Soc. 74, 5778 (1952), G. Schwarz Org. Synth. Coll. Vol. III, 332].

For synthesis of the derivatives of general formula XIII for which $R_7$ can have the previously mentioned meaning, and $R'_7$=hydrogen, however, amide VIII' must be reacted with 2-bromaldehydes (OHC—CHBr—$R_7$) in the presence of phosphorus pentasulfide.

For synthesis of calcitriol derivatives, which carry imidazole substituents at C-25, the derivative of general formula X can be reacted in the presence of primary amines such as $R_8NH_2$, whereby imidazole derivatives of general formula XIV are produced.

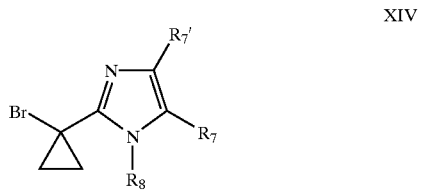

Substituent $R_8$ can be a hydrogen atom or a straight-chain or branched, saturated or unsaturated alkyl radical with up to 12 carbon atoms.

In addition, the creation of imidazole systems can also be carried out from amidine VIII″ that corresponds to carboxylic acid VIII

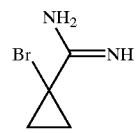

with 1-bromoketones (Br—$CH_2$—CO—$R_7$) or 2-bromaldehydes (OHC—CHBr—$R'_7$).

The linkage of thiazole or imidazole fragments can be carried out as described for the oxazole case, whereby derivatives of general formula XV are produced. In the case of several acid hydrogen atoms, either a suitable protective group technique must be used or the selective halogen/lithium exchange has to be carried out on bromocyclopropane by setting very low temperatures (−130 to −100° C.)

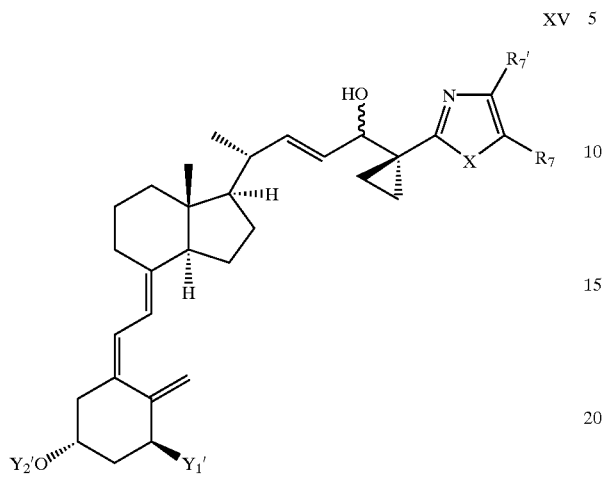

XV

In general formula XV, X can mean a sulfur atom or the previously defined unit N—R$_8$. All other radicals and the further treatment of the derivatives of general formula XV have been described previously.

Starting from carboxylic acid VIII or derivatives thereof (esters, amides, acid chlorides), 1,4-diketones of general formula XVI can be generated under standard reaction conditions [for use of functionalized organometallic reagents, see, e.g., M. Yus et al. J. Org. Chem. 56, 3825 (1991), J. Barluenga et al. J. Chem. Soc. Perk. I 3113 (1988), followed by manipulations of the functional groups such as, e.g., ketal cleavages].

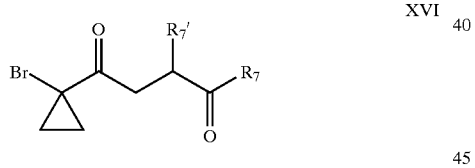

XVI

By using the reaction conditions that were already used for the reaction of the derivatives of general formula X (action of acid, phosphorus pentasulfide or the like, or primary amines such as R$_8$NH$_2$), furan, thiophene or pyrrole derivatives of general formula XVII can be obtained,

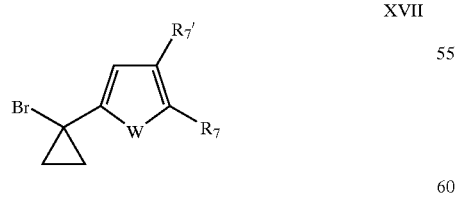

XVII whereby W can mean an oxygen atom, a sulfur atom or the N—R$_8$ group.

The linkage to the vitamin D system is carried out analogously to the previously described cases, whereby derivatives of general formula XVIII accumulate.

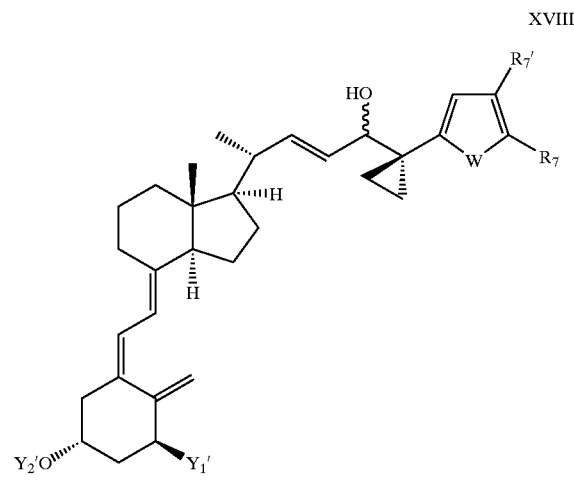

XVIII

The subsequent reaction steps as well as the radicals have already been described previously.

Carboxylic acid VIII can also be converted into other suitable components. Thus, aldehyde IXX can be produced by reduction of the carboxylic acid or a derivative (acid chloride, ester, amide—especially N-methoxy-N-methylamide) and optionally reoxidation.

IXX

Acetylene derivative XX is obtained by reaction with the Seyferth reagent [S. Schreiber et al. J. Am. Chem. Soc. 112, 5583 (1990)] or under Corey-Fuchs conditions [P. Ma et al. Synth. Comm. 25, 3641 (1995)].

XX

Heterocycles of general formulas XXIa and XXIb (isoxazoles), XXIIa and XXIIb (pyrrazole) as well as XXIIIA and XXIIIb (triazole) can be produced by 1,3-dipolar cycloadditions with nitrile oxides (R$_7$—C=N—O$^-$) diazo compounds (R$_{7\_}$CH$^-$—N=N$^+$) or alkylazides (R$_7$—N$^-$—N=N$^+$).

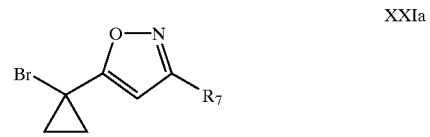

XXIa

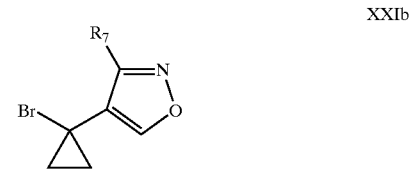

XXIb

-continued

XXIIa

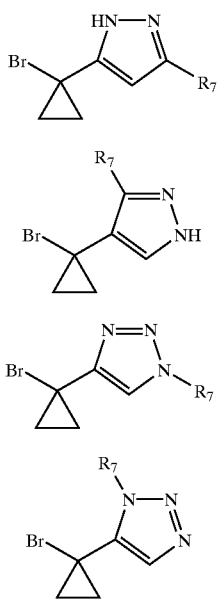

XXIIb

XXIIIa

XXIIIb

Analogously to the previously described syntheses, these heterocycles—optionally under protection of the functional groups—can be linked with vitamin D-aldehyde VII, whereby derivatives of general formula II with the corresponding heterocyclic substituents for Z' accumulate.

If aldehyde IXX is converted in a Wittig reaction into the corresponding vinyl compound, the 1,3-dipolar cycloadditions can also be carried out, which would then yield the corresponding isoxazolines, pyrazolines or triazolines. Their treatment can be carried out analogously to the heteroaromatic derivatives.

It is also possible to convert carboxylic acid VIII or a corresponding derivative (ester, amide, acid chloride) under standard conditions (e.g., Claisen condensation) into 1,3-diketones of general formula XXIV.

XXIV

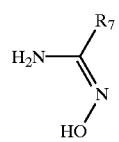

Isoxazoles of general formula XXV can now be produced in the presence of hydroxylamine, and pyrazoles of general formula XXVI can be produced with hydrazines such as $R_8$—NH—$NH_2$.

XXV

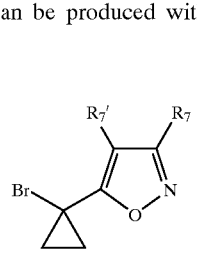

XXVI

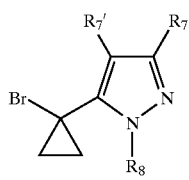

Analogously to the previously described syntheses, these heterocycles—optionally under protection of the functional groups—can be linked with vitamin D-aldehyde VII, whereby derivatives of general formula II with the corresponding heterocyclic substituents accumulate.

For synthesis of 1,2,4-oxadiazoles, derivatives of carboxylic acid VIII (acid chlorides, -esters, -orthoesters) can be reacted with amidoximes of general formula XXVII

XXVII

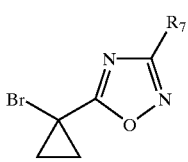

and thermally converted (optionally addition of trifluoroacetic acid anhydride) into 1,2,4-oxadiazoles of general formula XXVIII [L. B. Clapp Adv. Heterocycl. Chem. 20, 65 (1976)]. The formation of the 1,2,4-oxadiazoles can also be carried out under basic conditions (e.g., sodium methanolate).

XXVIII

Analogously to the previously described syntheses, heterocycles of general formula XXVIII—optionally under protection of the functional groups—can be linked with the vitamin D-aldehyde VII, whereby derivatives of general formula II with the corresponding heterocyclic substituents accumulate.

Carboxylic acid derivatives (e.g., esters), which already have the calcitriol skeleton (DE 42 34 382), can also be converted directly into the corresponding 1,2,4-oxadiazoles.

For synthesis of 1,3,4-oxadiazoles, derivatives of carboxylic acid VIII can be converted into 1,2-diacylhydrazines of general formula XXIX

XXIX

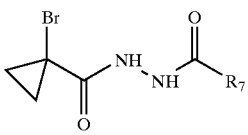

which can be reacted thermally or under acid catalysis (e.g., acetic acid, hydrochloric acid, i.a.) to 1,3,4-oxazolines of general formula XXX (DE 28 08 842).

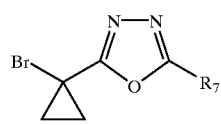

XXX

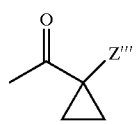

XXXIII

Analogously to the previously described syntheses, heterocycles of general formula XXX—optionally under protection of functional groups—can be linked with vitamin D-aldehyde VII, whereby derivatives of general formula II with the corresponding heterocyclic substituents accumulate.

The production of compounds that carry 6-membered rings at C-25 can be carried out quite analogously. For this purpose, the necessary reagents of general formula XXXI must be synthesized using known methods to create 6-ring-heterocycles (R. M. Acheson "An Introduction to the Chemistry of Heterocyclic Compounds," 3rd Edition, John Wiley & Sons, New York, 1976, A. R. Katritzky, J. M. Lagowsky "The Principles of Heterocyclic Chemistry," Chapman & Hall, London, 1971).

XXXI

Z" means pyridine, pyrazine, pyrimidine, pyridazine, piperidine, tetrahydropyran rings, which can be substituted like the 5-membered rings in one or more places with substituents such as $R_7$.

Another general method of side chain introduction uses the aldehyde of general formula XXXII,

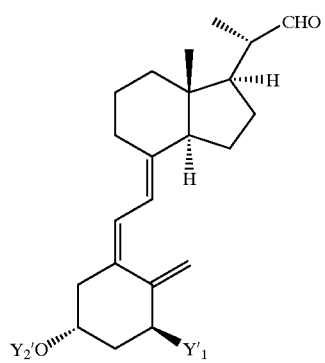

XXXII which is accessible by photochemical isomerization of aldehyde III (conditions analogous to reaction V reacted to VI). Correspondingly, the isomerization as well as further reactions also apply for aldehydes of general formula IV. By way of example, however, only the further treatment of XXXII is cited.

The introduction of the side chain is carried out here by reaction with components of general formula XXXIII, whereby Z''' can have all definitions that have already been given for Z, Z' and Z''. The synthesis of the corresponding components is possible according to standard methods. The linkage to aldehyde XXXII is carried out by deprotonation of ketone XXXIII with a base (e.g., lithium diisopropylamide, lithium-, sodium-, potassium hexamethyldisilazide, i.a.) in an aldol reaction, whereby derivatives of general formula XXXIV accumulate.

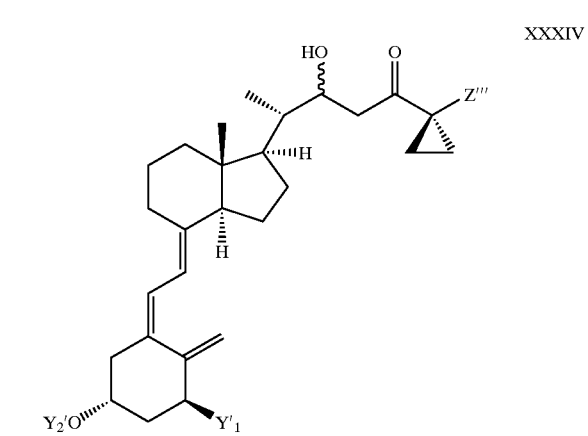

XXXIV

Conversion of the free hydroxy group into a leaving group (e.g., acetate, trifluoroacetate, methanesulfonate, toluenesulfonate, trifluoromethanesulfonate) and elimination under basic conditions (e.g., diazabicycloundecane, diazabicyclononane, triethylamine, i.a.) then yields enone derivatives of general formula XXXV

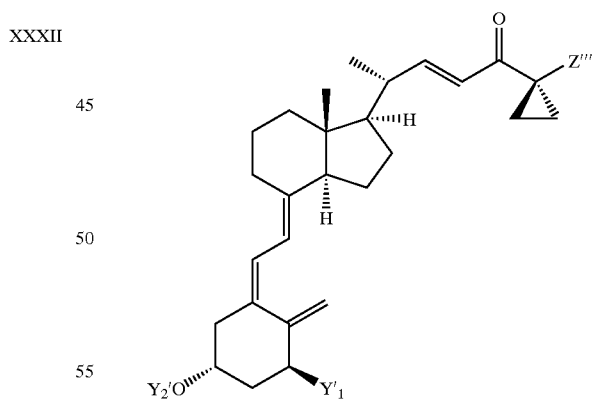

XXXV

Reduction of the keto groups with a reducing agent (e.g., sodium borohydride, sodium borohydride/cerium trichloride, lithium aluminum hydride, diisobutylaluminum hydride, i.a.) then results in derivatives of general formula II, for which the following applies: Q represents a hydroxymethyl group and Z''' is equal to Z', which are further reacted as described.

The production of compounds of general formula I, if $R_1$ and $R_2$ mean hydrogen atoms, is carried out in that a compound of general formula II',

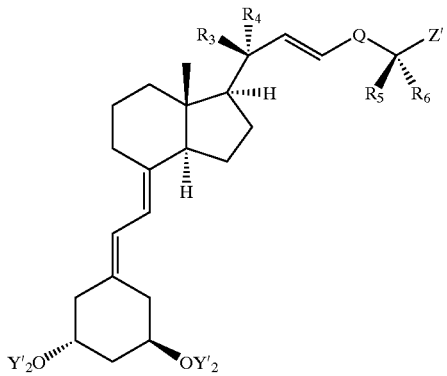

II' whereby the already mentioned meanings exist for Y'$_2$, R$_3$, R$_4$, R$_5$, R$_6$, Q and Z', is treated analogously to the conditions that are described for the reaction of II.

The production of compounds of general formula II' is carried out in a convergent synthesis method, whereby CD and A-ring fragments are separately structured. For synthesis of the CD fragments, aldehyde XXXVI, known in the literature [H. H. Inhoffen et al. Chem. Ber. 91, 780 (1958), Chem. Ber. 92, 1772 (1959), W. G. Dauben 30 Tetrahedron Lett., 677 (1989)] is used,

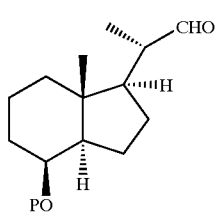

XXXVI in which P means an acyl-, alkyl- or aryl-substituted silyl or tetrahydropyranyl, tetrahydrofuranyl, methoxymethyl, ethoxyethyl group or an acyl group (e.g., acetyl group, benzoyl group) or another alcohol protective group (see T. W. Greene, P. G. M. Wuts "Protective Groups in Organic Synthesis," 2$^{nd}$ Edition, John Wiley & Sons, Inc., 1991).

According to known processes, which have already been described for the normal series (see front and see also WO 94/07853), the corresponding side chains can also be built up on the CD fragment, whereby derivatives of general formula XXXVII accumulate.

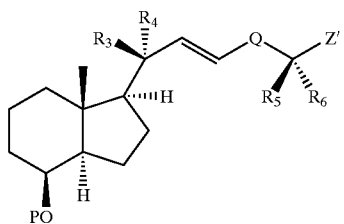

XXXVII

The radicals have been described previously. Protective group P is now removed by suitable reagents. For silyl protective groups, tetrabutylammonium fluoride, hydrofluoric acid or hydrofluoric acid/pyridine is used. In the case of the other ether groups, acids (e.g., p-toluenesulfonic acid, pyridinium-p-toluenesulfonate, acetic acid, oxalic acid, hydrochloric acid, phosphoric acid, acidic ion exchanger) are used. The acyl groups are cleaved under basic conditions (potassium carbonate, potassium hydroxide, sodium hydroxide, lithium hydroxide in alcohols, water, THF or corresponding solvent mixtures), whereby derivatives of general formula XXXVIII accumulate.

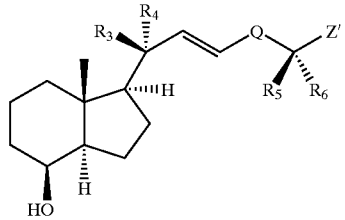

XXXVIII

The free hydroxy group is now converted with an oxidizing agent (pyridinium dichromate, pyridinium chlorochromate, barium manganate, Swern conditions, Dess-Martin reagent) into a ketone of general formula XXXIX.

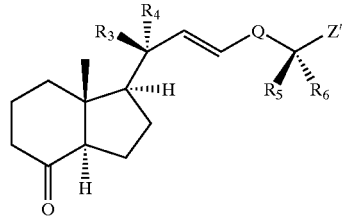

XXXIX

The compounds of general formula XXXIX are now converted by reaction with the anion of phosphine oxides of general formula XL produced by a base such as n-butyllithium or lithium diisopropylamine [H. F. DeLuca et al. Tetrahedron Lett. 32, 7663 (1991)]

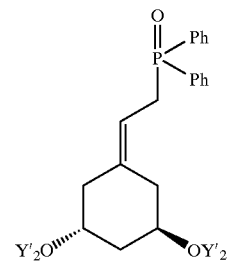

XL into a compound of general formula II'.

For the synthesis bf calcitriol derivatives of general formula II with 26,27-cyclomodification, which in addition have pyridyl substituents at C-25, the following synthesis method can be employed.

Carboxylic acid VIII is converted with pyridine thiol in the presence of N,N'-dicyclohexylcarbodiimide into thioesters XLI,

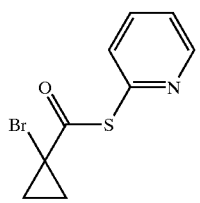

XLI which are reacted with Grignard reagents such as XLII [Examples: D. Wenkert et al. J. Org. Chem. 50, 4114 (1985); S. Borelly, L. A. Paquette J. Am. Chem. Soc. .118, 727 (1996); T. E. Bellas Tetrahedron 25, 5149 (1969)]

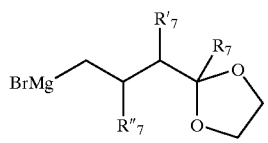

XLII to ketones of general formula XLIII. For R"$_7$, the same definition applies as for R$_7$ and R'$_7$.

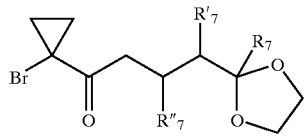

XLIII

The cyclization to pyridine derivatives of general formula XLIV can now be carried out under standard conditions (e.g., acetic acid, hydroxylamine hydrochloride) [G. Chelucci Synth. Comm. 15, 808 (1985)].

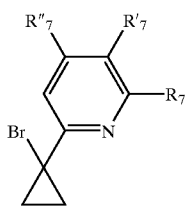

XLIV

The creation of the side chain is then carried out as in the case of oxazole derivatives by reaction of the cyclopropyl-metal compound that is generated by bromine-metal exchange and vitamin D-C-24 aldehyde VII, whereby derivatives of general formula XLV are obtained.

XLV

These can be regarded as special cases of general formula II, whose further reaction is already described.

For synthesis of calcitriol derivatives with 26,27-cyclomodification, which in addition has oxazoline substituents at C-25, the following synthesis method can be employed.

Carboxylic acid VIII is converted into the acid chloride of general formula XLVI.

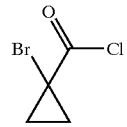

XLVI

The carboxylic acid can now be brought to reaction with amino alcohols of general formula XLVII,

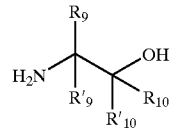

XLVII whereby R$_9$, R'$_9$, R$_{10}$, and R'$_{10}$, independently of one another, mean a hydrogen atom, a straight-chain or branched, saturated or unsaturated cyclic (aromatic, aliphatic) alkyl radical with up to 12 carbon atoms, which can be interrupted at any point by oxa, thia or aza groups (substituted or unsubstituted) or by sulfoxide or sulfo groups or can carry other substituents (free or protected hydroxyl groups, halogen atoms).

In this case, amides of general formula XLVIII are produced,

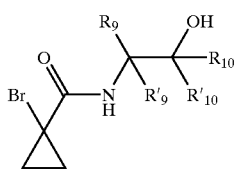

XLVIII which are converted under standard conditions (e.g., phosphorus oxychloride) into the oxazolines of general formula XLIX [N. Langlois et al. Heterocycles 42, 635 (1996)].

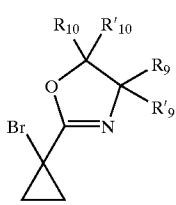

XLIX

The creation of the side chain is then carried out as in the case of the oxazole derivatives by reaction of the cyclopropyl-metal compound that is generated by bromine-metal exchange and the vitamin D-C-24-aldehyde VII, whereby derivatives of general formula L are obtained.

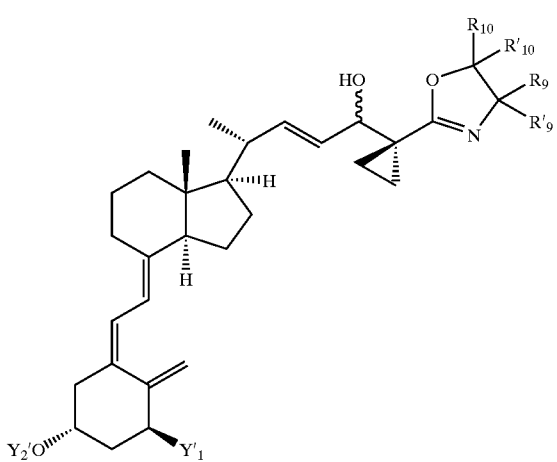

L

These can be regarded as special cases of general formula II, whose further reaction is already described.

The invention thus also contains intermediate products of general formulas XI, XII and XLIV within the production of vitamin D derivatives according to the invention

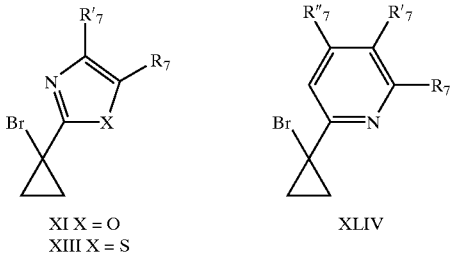

XI X = O
XIII X = S

XLIV in which $R_7$, $R'_7$ and $R''_7$, independently of one another, mean a hydrogen atom, a straight-chain or branched, saturated or unsaturated alkyl radical with up to 12 carbon atoms, which at any points can be interrupted by oxa, thia or aza groups (substituted or unsubstituted) or sulfoxide or sulfo groups or can carry other substituents (free or protected hydroxy groups, halogen atoms).

The following examples are used for a more detailed explanation of the invention.

Synthesis of the Starting Compounds in the 5-Alkyloxazole Series (5Z,7E,22E)-(1S,3R)-1,3-Bis[[dimethyl(1,1-dimethylethyl)-silyl]oxy]-9,10-secochola-5,7,10(19),22-tetraen-24-al 3 a) An amount of 1.40 g of (5E,7E,22E)-(1S,3R)-1,3-bis[[dimethyl(1,1-dimethylethyl)-silyl]oxy]-N-methyl-N-methoxy-9,10-secochola-5,7,10(19),22-tetraen-24-amide 1 (WO 94/07853) is dissolved in 200 ml of toluene, and after 232 mg of anthracene and 4 drops of triethylamine are added, it is irradiated through Pyrex glass with a high-pressure mercury-vapor lamp (Heraeus TQ 150) for 12 minutes under nitrogen. Then, it is filtered and concentrated by evaporation. After this procedure is performed several times (11 times), 11.4 g of (5Z,7E,22E)-(1S,3R)-1,3-bis[[dimethyl(1,1-dimethylethyl)silyl]oxy]-N-methyl-N-methoxy-9,10-secochola-5,7,10(19),22-tetraene-24-amide 2 is obtained as a yellow oil.

b) 7.8 g of amide 2 is dissolved in 39.15 ml of THF and treated drop by drop at −78° C. with 49.62 ml of diisobutylaluminum hydride (1.2 M in toluene). After 70 minutes, 2.84 ml of methanol is added at −78° C., and then the reaction mixture is stirred into ice-cold sodium tartrate solution and stirred thoroughly with 370 ml of diethyl ether for 1.5 hours. The ether phase is concentrated by evaporation and chromatographed on silica gel with ethyl acetate/hexane, whereby 5.44 g of title compound 3 accumulates as a yellow, resin-like material.

$^1$H-NMR (300 MHz, CDCl$_3$): δ=0.08 ppm (s, 12H); 0.58 (s, 3H); 0.88 (s, 18H); 1.17 (d, 3H); 4.20 (m, 1H); 4.38 (m, 1H); 4.85 (brs, 1H); 5.18 (brs, 1H); 6.02 (d, 1H); 6.08 (dd, 1H); 6.23 (d, 1H); 6.72 (dd, 1H); 9.48 (d, 1H)

2-(1-Bromocyclopropyl)-5-propyloxazole 7 a) A mixture of 2.57 g of 1-bromocyclopropanecarboxylic acid 4 [H. M. R. Hoffmann et al. J. Org. Chem. 54, 6096 (1989)], 2.22 g of 1-amino-2-pentanone hydrochloride 5 [M. Jackman et al. J. Am. Chem. Soc. 70, 2884 (1948)] and 3.36 g of N,N'-dicyclohexylcarbodiimide in 234 ml of methylene chloride in the presence of 2.46 ml of triethylamine is stirred overnight at room temperature. Then, it is filtered, the filtrate is concentrated by evaporation, and the residue is chromatographed on silica gel with ethyl acetate/hexane. 2.74 g of 1-bromo-N-(2-oxopentyl)-cyclopropane-1-carbamide 6 is obtained as a crystallizing oil.

$^1$H-NMR (300 MHz, CDCl$_3$): δ=0.92 pm (t, 3H); 1.32 (m, 2H); 1.68 (m, 4H); 2.45 (t, 2H); 4.12 (d, 2H); 7.58 (brs, 1H)

Obtained analogously are:

1-Bromo-N-(2-oxopropyl)-cyclopropane-1-carbamide from 1-amino-2-propanone hydrochloride [J. D. Hepworth Org. Synth. 45, 1 (1965)

1-bromo-N-(2-oxobutyl)-cyclopropane-1-carbamide from 1-amino-2-butanone hydrochloride [M. Jackman et al. J. Am. Chem. Soc. 70, 2884 (1948)]

1-bromo-N-(2-oxoheptyl)-cyclopropane-1-carbamide from 1-amino-2-heptanone hydrochloride [M. Jackman et al. J. Am. Chem. Soc. 70, 2884 (1948)]

b) 2.14 g of 6 and 6.42 g of polyphosphoric acid are held at 140° C. for 3.5 hours. The reaction mixture is then mixed with ice/sodium carbonate solution and extracted with ethyl acetate. After drying on sodium sulfate, it is chromatographed on silica gel with ethyl acetate/hexane. 1.47 g of title compound 7 is obtained as a yellow oil.

$^1$H-NMR (300 MHz, CDCl$_3$): δ=0.98 ppm (t, 3H); 1.50 (m, 2H); 1.60 (m, 4H); 2.59 (t, 2H); 6.65 (s, 1H)

2-(1-Bromocyclopropyl)-5-methyloxazole 8

4.62 g of 1-bromo-N-(2-oxopropyl)-cyclopropane-1-carbamide is held at 60° C. in 35.47 ml of concentrated sulfuric acid for 30 minutes. The cooled reaction mixture is stirred into ice water and made basic in batches with sodium carbonate decahydrate. Then, it is extracted with ethyl acetate, dried on sodium sulfate, and concentrated by evaporation. Chromatography of the oily residue on silica gel with ethyl acetate/hexane yields 2.79 g of title compound 8 a as a yellowish oil.

$^1$H-NMR (300 MHz, CDCl$_3$): δ=1.50 ppm (m, 2H); 1.60 (m, 2H); 2.30 (s, 3H); 6.65 (s, 1H)

Obtained analogously are:

2-(1-Bromocyclopropyl)-5-ethyloxazole 9 from 1-bromo-N-(2-oxobutyl)-cyclopropane-1-carbamide $^1$H-NMR (300 MHz, CDCl$_3$): δ=1.24 ppm (t, 3H); 1.50 (m, 2H); 1.60 (m, 2H); 2.65 (q, 2H); 6.65 (s, 1H)

2-(1-bromocyclopropyl)-5-pentyloxazole 10 from 1-bromo-N-(2-oxoheptyl)-cyclopropane-1-carbamide $^1$H-NMR (300 MHz, CDCl$_3$): δ=0.90 ppm (t, 3H); 1.33 (m, 4H); 1.50 (m, 2H); 2.60 (t, 2H); 6.65 (s, 1H)

EXAMPLE 1

(5Z,7E,22E)-(1S,3R,24S)-25-(5-Propyloxazol-2-yl)-26,27-cyclo-9,10-secocholesta-5,7,10(19),22-tetraene-1,3,24-triol 12a and (5Z,7E,22E)-(1S,3R,24S)-25-(5-propyloxazol-2-yl)-26,27-cyclo-9,10-secocholesta-5,7,10(19),22-tetraene-1,3,24-triol 12b 1.0 g of 2-(1-bromocyclopropyl)-5-propyloxazole 7 in 2.0 ml of diethyl ether is added drop by drop at −78° C. to 4.78 ml of tert-butyllithium (1.7 M in pentane) in 13.6 ml of diethyl ether. After 5 minutes, 869 mg of 3 in 5.44 ml of diethyl ether is added in drops. After 10 minutes, the reaction mixture is allowed to reach 0° C. and then stirred into saturated ammonium chloride solution. After extraction with diethyl ether and drying on sodium sulfate, 1.58 g of yellow oil is obtained. By chromatography on silica gel with ethyl acetate/hexane, 420 mg of (5Z,7E,22E)-(1S,3R,24S)-1,3-bis[[dimethyl(1,1-dimethyl-ethyl)silyl]oxy]-25-(5-propyloxazol-2-yl)-26,27-cyclo-9,10-secocholesta-5,7,10(19),22-tetraen-24-ol 11a and 380 mg of (5Z,7E,22E)-(1S,3R,24R)-1,3-bis[[dimethyl(1,1-dimethylethyl)-silyl]oxy]-25-(5-propyloxazol-2-yl)-26,27-cyclo-9,10-secocholesta-5,7,10(19),22-tetraen-24-ol 11b are obtained in the elution sequence as oils.

410 mg of 11a is allowed to stand in 15.9 ml of THF with 841 mg of tetrabutylammonium fluoride(trihydrate) overnight at room temperature. Then, another 420 mg of tetrabutylammonium fluoride(trihydrate) is added, and it is stirred for 5 hours. After saturated sodium bicarbonate solution and saturated sodium chloride solution are added, it is extracted with ethyl acetate. After the organic phase is dried with sodium sulfate, it is concentrated by evaporation, and the residue is chromatographed on silica gel with ethyl acetate/hexane. 110 mg of title compound 12a is obtained as a colorless oil.

$^1$H-NMR (300 MHz, CDCl$_3$): δ=0.57 ppm (s, 3H); 1.00 (m, 8H); 1.15 (m, 2H); 2.55 (t, 2H); 4.12 (d, 2H); 4.23 (m, 1H); 4.43 (m, 1H); 5.00 (brs, 1H); 5.32 (brs, 1H); 5.42 (dd, 1H); 5.58 (dd, 1H); 6.00 (d, 1H); 6.38 (d, 1H); 6.58 (s, 1H)

Analogously, title compound 12b is obtained from 11b with tetrabutylammonium fluoride(trihydrate) as a colorless foam.

$^1$H-NMR (300 MHz, CDCl$_3$): δ=0.57 ppm (s, 3H); 1.00 (m, 8H); 1.15 (m, 2H); 2.55 (t, 2H); 4.12 (d, 2H); 4.23 (m, 1H); 4.43 (m, 1H); 5.00 (brs, 1H); 5.32 (brs, 1H); 5.42 (dd, 1H); 5.53 (dd, 1H); 6.00 (d, 1H); 6.38 (d, 1H); 6.58 (s, 1H)

EXAMPLE 2

(5Z,7E,22E)-(1S,3R,24R)-25-(5-Methyloxazol-2-yl)-26,27-cyclo-9,10-secocholesta-5,7,10(19),22-tetraene-1,3,24-triol 13b Analogously to Example 1, starting from aldehyde 3, title compound 13b is obtained as a colorless foam with 2-(1-bromocyclopropyl)-5-methyloxazole 8.

$^1$H-NMR (300 MHz, CDCl$_3$): δ=0.57 ppm (s, 3H); 0.97 (m, 2H); 1.05 (m, 3H); 1.15 (m, 2H); 2.24 (s, 2H); 4.10 (d, 2H); 4.23 (m, 1H); 4.43 (m, 1H); 5.00 (brs, 1H); 5.32 (brs, 1H); 5.42 (dd, 1H); 5.53 (dd, 1H); 6.00 (d, 1H); 6.38 (d, 1H); 6.58 (s, 1H)

EXAMPLE 3

(5Z,7E,22E)-(1S,3R,24R)-25-(5-Ethyloxazol-2-yl)-26,27-cyclo-9,10-secocholesta-5,7,10(19),22-tetraene-1,3,24-triol 14b Analogously to Example 1, starting from aldehyde 3, title compound 14b is obtained as a colorless foam with 2-(1-bromocyclopropyl)-5-ethyloxazole 9.

$^1$H-NMR (300 MHz, CDCl$_3$): δ=0.57 ppm (s, 3H); 0.97 (m, 2H); 1.05 (m, 3H); 1.20 (m, 5H); 2.60 (q, 3H); 4.12 (d, 2H); 4.23 (m, 1H); 4.43 (m, 1H); 5.00 (brs, 1H); 5.32 (brs, 1H); 5.42 (dd, 1H); 5.53 (dd, 1H); 6.00 (d, 1H); 6.38 (d, 1H); 6.58 (s, 1H)

EXAMPLE 4

(5Z,7E,22E)-(1S,3R,24R)-25-(5-Pentyloxazol-2-yl)-26,27-cyclo-9,10-secocholesta-5,7,10(19),22-tetraene-1,3,24-triol 15b Analogously to Example 1, starting from aldehyde 3, title compound 15b is obtained as a colorless foam with 2-(1-bromocyclopropyl)-5-pentyloxazole 10.

$^1$H-NMR (300 MHz, CDCl$_3$): δ=0.57 ppm (s, 3H); 0.90 (t, 3H); 1.05 (m, 3H); 1.15 (m, 2H); 2.55 (s, 3H); 4.12 (d, 2H); 4.23 (m, 1H); 4.43 (m, 1H); 5.00 (brs, 1H); 5.32 (brs, 1H); 5.42 (dd, 1H); 5.53 (dd, 1H); 6.00 (d, 1H); 6.38 (d, 1H); 6.60 (s, 1H)

Synthesis of the Starting Materials in the 4-Alkylthiazole Series 2-(1-Bromocyclopropyl)-4-ethylthiazole 17

10.0 g of 1-bromopropanecarboxylic acid in 4, and 173 ml of methylene chloride are stirred with 8.36 g of N-hydroxysuccinimide for 10 minutes at room temperature under nitrogen. At 0° C., 15.0 g of N,N-dicyclohexylcarbodiimide is added, and it is stirred for 3 hours at 0° C. Then, 10.0 ml of a 33% aqueous ammonia solution is added, and it is stirred for another 3 hours at 0°

C. The reaction mixture is filtered, the filtrate is concentrated by evaporation, and the residue (14.12 g of colorless solid) is chromatographed on silica gel with ethyl acetate/hexane. 9.01 g of 1-bromocyclopropanecarboxylic acid amide 16 is obtained as a colorless solid (flash point 104–107° C.).

4.64 g of 16 in 2.0 ml of toluene is stirred with 1.11 g of phosphorus pentasulfide and 4.17 g of 1-bromo-2-butanone (from 2-butanone and bromine in the presence of methanol) for 13 minutes at 50° C. The cooled reaction mixture is mixed with ice and 100 ml of saturated sodium bicarbonate solution. Then, it is extracted with ethyl acetate, and the organic phase is dried with sodium sulfate. After the solvent is removed, the residue is chromatographed on silica gel with ethyl acetate/hexane, whereby 810 mg of title compound 17 accumulates as a yellow oil.

$^1$H-NMR (300 MHz, CDCl$_3$): δ=1.25 ppm (t, 3H); 1.60 (m, 2H); 1.75 (m, 2H); 2.72 (q, 2H); 6.78 (s, 1H)

Obtained analogously are:

2-(1-Bromocyclopropyl)-4-methylthiazole 18 from chloroacetone at 100° C. and a reaction time of 30 minutes.

$^1$H-NMR (300 MHz, CDCl$_3$): δ=1.60 ppm (m, 2H); 1.75 (m, 2H); 2.38 (s, 3H); 6.78 (s, 1H)

2-(1-Bromocyclopropyl)-4-propylthiazole 19 from 1-bromopentanone at 50° C. and a reaction time of 20 minutes.

$^1$H-NMR (300 MHz, CDCl$_3$): δ=0.95 ppm (t, 3H); 1.60 (m, 2H); 1.69 (m, 2H); 1.75 (m, 2H); 2.65 (t, 2H); 6.78 (s, 1H)

2-(1-Bromocyclopropyl)-4-butylthiazole 20 from 1-bromo-2-hexanone at 100° C. and a reaction time of 2 minutes.

$^1$H-NMR (300 MHz, CDCl$_3$): δ=0.95 ppm (t, 3H); 1.38 (m, 2H); 1.60 (m, 2H); 1.75 (m, 2H); 2.68 (t, 2H); 6.78 (s, 1H)

EXAMPLE 5

(5Z,7E,22E)-(1S,3R,24S)-25-(4-Ethylthiazol-2-yl)-26,27-cyclo-9,10-secocholesta-5,7,10(19),22-tetraene-1,3,24-triol 22a and (5Z,7E,22E)-(1S,3R,24R)-25-(4-ethylthiazol-2-yl)-26,27-cyclo-9,10-secocholesta-5,7,10(19),22-tetraene-1,3,24-triol 22b 2.94 ml of tert-butyllithium (1.7 M in pentane) is added at −20° C. under nitrogen to 8 ml of Trapp mixture (THF, ether, pentane=4:1:1) and cooled to −116° C. (ether, liquid nitrogen). Then, 580 mg of 17 is added in drops to 1 ml of Trapp mixture, and it is stirred for 1 hour at −116° C. Then, 950 mg of aldehyde 3 is added in drops to 1 ml of Trapp mixture. After 30 minutes at this temperature, saturated ammonium chloride solution is added and extracted with ethyl acetate. After the organic phase is dried on sodium sulfate and after the solvent is concentrated by evaporation, a residue of 890 mg is obtained as a yellow oil. By chromatography on silica gel with ethyl acetate/hexane, 210 mg of (5Z,7E,22E)-(1S,3R,24S)-1,3-bis[[dimethyl(1,1-dimethylethyl)silyl]oxy]-25-(4-ethyl-thiazol-2-yl)-26,27-cyclo-9,10-secocholesta-5,7,10(19),22-tetraen-24-ol 21a and 200 mg of (5Z,7E,22E)-(1S,3R,24R)-1,3-bis[[dimethyl (1,1-dimethylethyl)silyl]oxy]-25-(4-ethylthiazol-2-yl)-26,27-cyclo-9,10-secocholesta-5,7,10(19),22-tetraen-24-ol 21b are obtained in the elution sequence as light yellow oils.

210 mg of 21a is dissolved in 7 ml of THF and allowed to stand with 420 mg of tetrabutylammonium fluoride (trihydrate) overnight at room temperature under nitrogen. Then, it is poured into a mixture of saturated sodium chloride and saturated sodium bicarbonate solution (50:1), extracted with ethyl acetate, the organic phase is washed with saturated sodium chloride solution, dried on sodium sulfate and concentrated by evaporation. The residue is chromatographed on silica gel with ethyl acetate/hexane, whereby 56 mg of title compound 22a is obtained as a colorless foam.

$^1$H-NMR (300 MHz, CDCl$_3$): δ=0.50 ppm (s, 3H); 0.98 (d, 3H); 1.05 (m, 4H); 1.25 (t, 3H); 2.74 (q, 2H); 3.97 (d, 1H); 4.23 (m, 1H); 4.43 (m, 1H); 5.00 (brs, 1H); 5.32 (brs, 1H); 5.40 (dd, 1H); 5.56 (dd, 1H); 6.00 (d, 1H); 6.38 (d, 1H); 6.65 (s, 1H)

Analogously, from 21b, title compound 22b is obtained as a colorless foam with tetrabutylammonium fluoride (trihydrate).

$^1$H-NMR (300 MHz, CDCl$_3$): δ=0.52 ppm (s, 3H); 0.98 (d, 3H); 1.05 (m, 4H); 1.25 (t, 3H); 2.74 (q, 2H); 3.98 (d, 1H); 4.23 (m, 1H); 4.43 (m, 1H); 5.00 (brs, 1H); 5.32 (brs, 1H); 5.38 (dd, 1H); 5.51 (dd, 1H); 6.00 (d, 1H); 6.38 (d, 1H); 6.65 (s, 1H)

EXAMPLE 6

(5Z,7E,22E)-(1S,3R,24R)-25-(4-Methylthiazol-2-yl)-26,27-cyclo-9,10-secocholesta-5,7,10(19),22-tetraene-1,3,24-triol 23b Analogously to Example 5, starting from aldehyde 3, title compound 23b is obtained as a colorless foam with 2-(1-bromocyclopropyl)-4-methylthiazole 18.

$^1$H-NMR (300 MHz, CDCl$_3$): δ=0.52 ppm (s, 3H); 1.00 (d, 3H); 1.05 (m, 4H); 2.40 (s, 3H); 3.98 (d, 1H); 4.23 (m, 1H); 4.43 (m, 1H); 5.00 (brs, 1H); 5.32 (brs, 1H); 5.38 (dd, 1H); 5.51 (dd, 1H); 6.00 (d, 1H); 6.38 (d, 1H); 6.65 (s, 1H)

EXAMPLE 7

(5Z,7E,22E)-(1S,3R,24R)-25-(4-Propylthiazol-2-yl)-26,27-cyclo-9,10-secocholesta-5,7,10(19),22-tetraene-1,3,24-triol 24b Analogously to Example 5, starting from aldehyde 3, title compound 24b is obtained as a colorless foam with 2-(1-bromocyclopropyl)-4-propylthiazole 19.

$^1$H-NMR (300 MHz, CDCl$_3$): δ=0.52 ppm (s, 3H); 0.98 (m, 7H); 1.05 (m, 4H); 2.68 (t, 2H); 3.98 (d, 1H); 4.23 (m, 1H); 4.43 (m, 1H); 5.00 (brs, 1H); 5.32 (brs, 1H); 5.38 (dd, 1H); 5.50 (dd, 1H); 6.00 (d, 1H); 6.38 (d, 1H); 6.65 (s, 1H)

EXAMPLE 8

(5Z,7E,22E)-(1S,3R,24R)-25-(4-Butylthiazol-2-yl)-26,27-cyclo-9,10-secocholesta-5,7,10(19),22-tetraene-1,3,24-triol 25b Analogously to Example 5, starting from aldehyde 3, title compound 25b is obtained as a colorless foam with 2-(1-bromocyclopropyl)-4-butylthiazole 20.

$^1$H-NMR (300 MHz, CDCl$_3$): δ=0.52 ppm (s, 3H); 0.92 (t, 3H); 0.98 (d, 3H); 1.05 (m, 4H); 2.69 (t, 2H); 3.98 (d, 1H); 4.23 (m, 1H); 4.43 (m, 1H); 5.00 (brs, 1H); 5.32 (brs, 1H); 5.38 (dd, 1H); 5.50 (dd, 1H); 6.00 (d, 1H); 6.38 (d, 1H); 6.65 (s, 1H)

Synthesis of Starting Materials in the Phenyl Series 1-(Phenylcyclopropan-1-yl)-1-ethanone 28

4.5 g of 1-phenyl-1-cyclopropanecarboxylic acid 26 in 80 ml of methylene chloride is stirred with 3.83 g of N-hydroxysuccinimide for 10 minutes at room temperature under nitrogen. At 0° C., 6.84 g of N,N'-dicyclohexylcarbodiimide is added, and it is stirred for 1.5 more hours. Then, 7.74 ml of an aqueous dimethylamine solution is added, and it is stirred for another 30 minutes at 0° C. and for 12 hours at room temperature. It is concentrated by evaporation, and the residue is chromatographed on silica gel with ethyl acetate/hexane, whereby 4.34 g of 1-phenyl-1-cyclopropanecarboxylic acid-dimethylamide 27 accumulates as a crystallizing oil.

4.34 g of 27 is dissolved in 189 ml of THF, cooled to −10° C., and 21.5 ml of methyllithium solution (1.6 M in diethyl ether) is added in drops under nitrogen. It is stirred for 2 hours at this temperature, and the reaction mixture is then poured into saturated ammonium chloride solution. After extraction with ethyl acetate, the organic phase is dried on sodium sulfate and concentrated by evaporation. The residue is chromatographed on silica gel with ethyl acetate/hexane, whereby 3.7 g of title compound 28 is obtained as a yellowish oil.

(5Z,7E)-(1S,3R)-1,3-Bis[[dimethyl(1,1-dimethylethyl)silyl]oxy]-9,10-secopregna-5,7,10(19)-triene-20-carbaldehyde 30

7.5 g of (5E,7E)-(1S,3R)-1,3-bis[[dimethyl(1,1-dimethylethyl)silyl]oxy]-9,10-seco-pregna-5,7,10(19)-triene-20-carbaldehyde 29 [M. J. Calverley Tetrahedron 43, 4609 (1987)] is dissolved in 200 ml of toluene, 2 g of anthracene and 0.5 ml of triethylamine are added and irradiated while nitrogen is passing through it in a Pyrex apparatus with a high-pressure mercury-vapor lamp for 30 minutes. Then, it is filtered, concentrated by evaporation, and the residue is chromatographed on silica gel with ethyl acetate/hexane, whereby title compound 30 is obtained as a colorless foam.

$^1$H-NMR (300 MHz, CDCl$_3$): δ=0.05 ppm (s, 12H); 0.55 (s, 3H); 0.88 (s, 18H); 1.11 (d, 3H); 2.37 (m, 1H); 4.18 (m, 1H); 4.37 (m, 1H); 4.84 (brs, 1H); 5.17 (brs, 1H); 6.00 (d, 1H); 6.22 (d, 1H)

EXAMPLE 9

(5Z,7E,22E)-(1S,3R,24S)-25-Phenyl-26,27-cyclo-9,10-secocholesta-5,7,10(19),22-tetraene-1,3,24-triol 35a and (5Z,7E,22E)-(1S,3R,24R)-25-phenyl-26,27-cyclo-9,10-secocholesta-5,7,10(19),22-tetraene-1,3,24-triol 35b 17.4 ml of n-butyllithium solution (1.6 M in hexane) is added in drops at 0° C. to 3.86 ml of diisopropylamine in 20.7 ml of THF under nitrogen. It is stirred for 20 minutes at this temperature, cooled to −78° C. and then 4.42 g of ketone 28 is added in drops to 6.2 ml of THF. After 1 hour at −78° C., 2.3 g of aldehyde 30 is added to 18.8 ml of THF, and it is stirred for 1 more hour. The reaction mixture is then stirred into ice-cold ammonium chloride solution and extracted with ethyl acetate. After the organic phase is dried on sodium sulfate, the solvent is removed and chromatographed on silica gel with ethyl acetate/hexane, whereby 1.57 g of (5Z,7E)-(1S,3R)-1,3-bis[[dimethyl(1,1-dimethylethyl)silyl]oxy]-22-hydroxy-25-phenyl-26,27-cyclo-9,10-secocholesta-5,7,10(19)-trien-24-one 31 is obtained as a colorless foam.

1.57 g of 31 is dissolved in 6.3 ml of pyridine, mixed with 2.08 ml of acetic anhydride and stirred overnight under nitrogen at room temperature. Then, the reaction mixture is mixed with aqueous oxalic acid (5%) and extracted with ethyl acetate. After the organic phase is dried on sodium sulfate and after chromatography on silica gel with ethyl acetate/hexane, 1.44 g of (5Z,7E)-(1S,3R)-22-(acetyloxy)-1,3-bis[[dimethyl(1,1-dimethylethyl)silyl]oxy]-25-phenyl-26,27-cyclo-9,10-secocholesta-5,7,10(19)-trien-24-one 32 is obtained as a colorless foam.

1.44 g of 32 is dissolved in 40 ml of toluene and stirred with 8.13 ml of 1,8-diazabicyclo[5.4.0]undec-7-ene (DBU) for 30 minutes at 40° C. under nitrogen. The reaction mixture is diluted with 150 ml of ethyl acetate and stirred into 600 ml of 0.01N hydrochloric acid. It is extracted with ethyl acetate, dried on sodium sulfate, and the solvent is removed, whereby 1.31 g of (5Z,7E,22E)-(1S,3R)-1,3-bis[[dimethyl(1,1-dimethylethyl)silyl]oxy]-25-phenyl-26,27-cyclo-9,10-secocholesta-5,7,10(19),22-tetraen-24-one 33 is obtained as a colorless oil.

1.31 g of enone 33 is dissolved in 3.1 ml of THF and 7.2 ml of methanol and mixed at 0° C. under nitrogen with 7.2 ml of a 0.4 molar methanolic cerium trichloride-heptahydrate solution. Then, 200 mg of sodium borohydride is added in portions and stirred for 40 more minutes at 0° C. Ice water is now added, extracted with ethyl acetate and dried on sodium sulfate. The residue is chromatographed on silica gel with hexane/ethyl acetate, whereby in the elution sequence, 133 mg of (5Z,7E,22E)-(1S,3R,24S)-1,3-bis[[dimethyl(1,1-dimethylethyl)silyl]oxy]-25-phenyl-26,27-cyclo-9,10-secocholesta-5,7,10(19),22-tetraen-24-ol 34a and 374 mg of (5Z,7E,22E)-(1S,3R,24R)-1,3-bis[[dimethyl(1,1-dimethylethyl)silyl]oxy]-25-phenyl-26,27-secocholesta-5,7,10(19),22-tetraen-24-ol 34b accumulate as colorless foams.

133 mg of 34a is allowed to stand in 5.6 ml of THF with 295 mg of tetrabutylammonium fluoride(trihydrate) overnight at room temperature under nitrogen. The reaction mixture is then stirred into ice-cold saturated sodium bicarbonate solution and extracted with ethyl acetate. The combined organic phases are washed with water, dried on sodium sulfate and concentrated by evaporation. Chromatography of the residue on silica gel with ethyl acetate/hexane yields 38 mg of title compound 35a as a colorless foam.

$^1$H-NMR (300 MHz, CDCl$_3$): δ=0.57 ppm (s, 3H); 0.85 (m, 4H); 1.05 (d, 3H); 3.78 (d, 1H); 4.23 (m, 1H); 4.43 (m, 1H); 5.00 (brs, 1H); 5.30 (dd, 1H); 5.32 (brs, 1H); 5.42 (dd, 1H); 6.00 (d, 1H); 6.38 (d, 1H); 7.30 (m, 5H)

Analogously to 34a, title compound 35b is obtained as a colorless foam from 34b.

$^1$H-NMR (300 MHz, CDCl$_3$): δ=0.57 ppm (s, 3H); 0.85 (m, 4H); 1.00 (d, 3H); 3.70 (d, 1H); 4.23 (m, 1H); 4.43 (m, 1H); 5.00 (brs, 1H); 5.30 (dd, 1H); 5.32 (brs, 1H); 5.42 (dd, 1H); 6.00 (d, 1H); 6.38 (d, 1H); 7.30 (m, 5H)

Synthesis of the Starting Materials in the 4-Alkyl-Phenyl Series

4-Methylbenzene acetaldehyde 37

28.5 g of methoxymethyltriphenylphosphonium chloride is introduced into 350 ml of diethyl ether under nitrogen. At 0° C., 39.95 ml of n-butyllithium solution (1.6 M in hexane) is added in drops, and it is stirred for one hour at room temperature. 10 g of 4-methylbenzaldehyde in 50 ml of diethyl ether is now added, and it is stirred for one more hour. Sodium chloride solution is added to the reaction mixture, extracted with ethyl acetate, dried on sodium sulfate and concentrated by evaporation. After chromatography on silica gel with ethyl acetate/hexane, 7.8 g of 1-methoxy-2-(4-methylphenyl)-ethene 36 (E,Z-mixture) is obtained as a colorless oil, which is dissolved in 200 ml of acetone and is stirred overnight under nitrogen with 10 ml of 2N hydrochloric acid. Sodium chloride solution is added, extracted with ethyl acetate, dried on sodium sulfate and concentrated by evaporation. Chromatographic purification on silica gel with ethyl acetate/hexane yields 4.5 g of title compound 37 as a colorless oil.

$^1$H-NMR (300 MHz, CDCl$_3$): δ=2.38 ppm (s, 3H); 3.68 (d, 2H); 7.12 (d, 2H); 7.22 (d, 2H); 9.74 (t, 1H)

2-(4-Methylphenyl)-2-propenal 38

2.57 g of aldehyde 37 is introduced into 300 ml of methylene chloride under nitrogen, and 6.5 ml of triethylamine and 7.1 g of Eschenmoser's salt are added at 0° C. After 2.5 hours at 0° C., saturated ammonium chloride solution is added, extracted with methylene chloride, washed with sodium chloride solution, dried on sodium sulfate and concentrated by evaporation. The residue is chromatographed on silica gel with ethyl acetate/hexane, whereby 1.94 g of title compound 38 accumulates as a colorless oil.

$^1$H-NMR (300 MHz, CDCl$_3$): δ=2.39 ppm (s, 3H); 6.17 (s, 1H); 6.62 (s, 1H); 7.22 (d, 2H); 7.39 (d, 2H); 9.82 (s, 1H)

3-(4-Methylphenyl)-3-buten-2-ol 39

2.34 g of aldehyde 38 is dissolved in 150 ml of diethyl ether and cooled to −78° C. under nitrogen. 20 ml of methyllithium solution (1.6 M in diethyl ether) is now added in drops. After 1.5 hours at this temperature, it is quenched with saturated ammonium chloride solution, extracted with ethyl acetate, washed with sodium chloride solution, dried on sodium sulfate, and the solvent is removed. The residue is purified by chromatography on silica gel with ethyl acetate/hexane, whereby in addition to 237 mg of starting material, 1.06 g of title compound 39 accumulates as a colorless oil.

$^1$H-NMR (300 MHz, CDCl$_3$): δ=2.38 ppm (s, 3H); 1.35 (d, 3H); 4.82 (q, 1H); 5.28 (s, 1H); 5.34 (s, 1H); 7.18 (d, 2H); 7.32 (d, 2H)

3-(4-Methylphenyl)-3-buten-2-one 40

2.91 g of alcohol 39 is dissolved in 300 ml of methylene chloride, and 43.5 g of manganese dioxide is added under nitrogen. It is stirred overnight at room temperature, filtered on Celite, and the residue is chromatographed on silica gel with ethyl acetate/hexane, whereby 850 mg of title compound 40 in addition to 1.06 g of the starting material are obtained as colorless oils.

$^1$H-NMR (300 MHz, CDCl$_3$): δ=2.45 ppm (s, 3H); 2.60 (s, 3H); 5.94 (s, 1H); 6.12 (s, 1H); 7.28 (d, 2H); 7.88 (d, 2H)

1-[1-(4-Methylphenyl)cyclopropyl]ethanone 41

507 mg of sodium hydride (55% in paraffin oil) is introduced into 20 ml of dimethylformamide under nitrogen at 0° C., and 1.36 g of trimethylsulfonium iodide is added. After 30 minutes at this temperature, 845 mg of ketone 40 is added in drops to 4 ml of dimethylformamide. It is stirred for 1 more hour at 0° C., then quenched with sodium chloride solution, extracted with ethyl acetate, dried on sodium sulfate and concentrated by evaporation. After chromatography on silica gel with ethyl acetate/hexane, 447 mg of title compound 41 is obtained as a colorless oil.

$^1$H-NMR (300 MHz, CDCl$_3$): δ=1.14 ppm (m, 2H); 1.59 (m, 2H); 2.01 (s, 3H); 2.38 (s, 3H); 7.28 (d, 2H); 7.88 (d, 2H)

4-(1-Methylethyl)benzene acetaldehyde 43

27.7 g of methoxymethyltriphenylphosphonium chloride is introduced into 350 ml of diethyl ether under nitrogen. At 0° C., 38.8 ml of n-butyllithium solution (1.6 M in hexane) is added in drops, and it is stirred for one hour at room temperature. 12 g of 4-isopropylbenzaldehyde in 50 ml of diethyl ether is now added, and it is stirred for one more hour. Sodium chloride solution is added to the reaction mixture, extracted with ethyl acetate, dried on sodium sulfate and concentrated by evaporation. After chromatography on silica gel with ethyl acetate/hexane, 8.1 g of 1-methoxy-2-[4-(1-methylethyl)phenyl]-ethene 42 (E,Z-mixture) is obtained as a colorless oil, which is dissolved in 200 ml of acetone and stirred under nitrogen with 10 ml of 2N hydrochloric acid overnight. Sodium chloride solution is added, extracted with ethyl acetate, dried on sodium sulfate and concentrated by evaporation. Chromatographic purification on silica gel with ethyl acetate/hexane yields 5.1 g of title compound 43 as a colorless oil.

$^1$H-NMR (300 MHz, CDCl$_3$): δ=1.28 ppm (d, 6H); 2.92 (hept, 1H); 3.68 (d, 2H); 7.16 (d, 2H); 7.24 (d, 2H); 9.73 (t, 1H)

2-[4-(1-Methylethyl)phenyl]-2-propenal 44

4.65 g of aldehyde 43 is introduced into 300 ml of methylene chloride under nitrogen, and 7.9 ml of triethylamine and 6.9 g of Eschenmoser's salt are added at 0° C. After 2.5 hours at 0° C., saturated ammonium chloride solution is added, extracted with methylene chloride, washed with sodium chloride solution, dried on sodium sulfate and concentrated by evaporation. The residue is chromatographed on silica gel with ethyl acetate/hexane, whereby 3.84 g of title compound 44 accumulates as a colorless oil.

$^1$H-NMR (300 MHz, CDCl$_3$): δ=1.28 ppm (d, 6H); 2.93 (hept, 1H); 6.15 (s, 1H); 6.62 (s, 1H); 7.26 (d, 2H); 7.41 (d, 2H); 9.81 (s, 1H)

3-[4-(1-Methylethyl)phenyl]-3-buten-2-ol 45

6.1 g of aldehyde 44 is dissolved in 250 ml of diethyl ether and cooled under nitrogen to −78° C. 35.8 ml of a methllithium solution (1.6 M in diethyl ether) is now added in drops. After 1.5 hours at this temperature, it is quenched with saturated ammonium chloride solution, extracted with ethyl acetate, washed with sodium chloride solution, dried on sodium sulfate, and the solvent is removed. The residue is purified by chromatography on silica gel with ethyl acetate/hexane, whereby 2.8 g of title compound 45 accumulates as a colorless oil.

$^1$H-NMR (300 MHz, CDCl$_3$): δ=1.27 ppm (d, 6H); 2.92 (hept, 1H); 1.33 (d, 3H); 4.83 (q, 1H); 5.29 (s, 1H); 5.34 (s, 1H); 7.20 (d, 2H); 7.34 (d, 2H)

3-[4-(1-Methylethyl)phenyl]-3-buten-2-one 46

2.75 g of alcohol 45 is dissolved in 300 ml of methylene chloride, and 25.1 g of manganese dioxide is added under nitrogen. It is stirred overnight at room temperature, filtered on Celite, and the residue is chromatographed on silica gel with ethyl acetate/hexane, whereby 937 mg of title compound 46 in addition to 635 mg of the starting material is obtained as colorless oils.

$^1$H-NMR (300 MHz, CDCl$_3$): δ=1.28 ppm (d, 6H); 2.46 (s, 3H); 2.93 (hept, 1H); 5.97 (s, 1H); 6.14 (s, 1H); 7.33 (d, 2H); 7.98 (d, 2H)

1-[1-[4-(1-Methylethyl)phenyl]cyclopropyl]ethanone 47

474 mg of sodium hydride (55% in paraffin oil) is introduced into 20 ml of dimethylformamide under nitrogen at 0° C., and 1.29 g of trimethylsulfonium iodide is added. After 30 minutes at this temperature, 930 mg of ketone 46 is added in drops to 4 ml of dimethylformamide. It is stirred for 1 more hour at 0° C., then quenched with sodium chloride solution, extracted with ethyl acetate, dried on sodium sulfate and concentrated by evaporation. After chromatography on silica gel with ethyl acetate/hexane, 447 mg of title compound 47 is obtained as a colorless oil.

$^1$H-NMR (300 MHz, CDCl$_3$): δ=1.18 ppm (m, 2H); 1.28 (d, 6H); 1.60 (m, 2H); 2.92 (hept, 1H); 2.02 (s, 3H); 7.20 (d, 2H); 7.30 (d, 2H)

4-Butylbenzene acetaldehyde 49

21.1 g of methoxymethyltriphnylphosphonium chloride is introduced into 280 ml of diethyl ether under nitrogen. At 0° C., 29.6 ml of n-butyllithium solution (1.6 M in hexane) is added in drops, and it is stirred for one hour at room temperature. 10 g of 4-butylbenzaldehyde in 40 ml of diethyl ether is now added, and it is stirred for one more hour. Sodium chloride solution is added to the reaction mixture, extracted with ethyl acetate, dried on sodium sulfate and concentrated by evaporation. After chromatography on silica gel with ethyl acetate, 6.7 g of 2-(4-butylphenyl)-1-methoxyethene 48 (E,Z-mixture) is obtained as a colorless oil, which is dissolved in 200 ml of acetone and is stirred under nitrogen with 10 ml of 2N hydrochloric acid overnight. Sodium chloride solution is added, extracted with ethyl acetate, dried on sodium sulfate and concentrated by evaporation. Chromatographic purification on silica gel with ethyl acetate/hexane yields 3.9 g of title compound 49 as a colorless oil.

$^1$H-NMR (300 MHz, CDCl$_3$): δ=0.95 ppm (t, 3H); 1.37 (m, 2H); 1.62 (m, 2H); 3.68 (d, 2H); 7.14 (d, 2H); 7.20 (d, 2H); 9.74 (t, 1H)

3-(4-Butylphenyl)-3-buten-2-ol 51

3.86 g of aldehyde 43 is introduced into 300 ml of methylene chloride under nitrogen, and 6.0 ml of triethylamine and 5.3 g of Eschenmoser's salt are added at 0° C. After 2.5 hours at 0° C., saturated ammonium chloride solution is added, extracted with methylene chloride, washed with sodium chloride solution, dried on sodium sulfate and concentrated by evaporation. The residue is chromatographed on silica gel with ethyl acetate/hexane, whereby 3.24 g of 2-(4-butylphenyl)-2-propen-1-al 50 accumulates as a colorless oil, which is dissolved in 200 ml of diethyl ether and cooled under nitrogen to −78° C. 27.4 ml of a methyllithium solution (1.6 M in diethyl ether) is now added in drops. After 1.5 hours at this temperature, it is quenched with saturated ammonium chloride solution, extracted with ethyl acetate, washed with sodium chloride solution, dried on sodium sulfate, and the solvent is removed. The residue is purified by chromatography on silica gel with ethyl acetate/hexane, whereby 1.8 g of title compound 51 accumulates as a colorless oil.

$^1$H-NMR (300 MHz, CDCl$_3$): δ=0.97 ppm (t, 3H); 1.35 (d, 3H); 1.61 (m, 4H); 2.62 (t, 2H); 4.83 (q, 1H); 5.29 (s, 1H); 5.34 (s, 1H); 7.18 (d, 2H); 7.33 (d, 2H)

3-(4-Butylphenyl)-3-buten-2-one 52

1.07 g of alcohol 51 is dissolved in 100 ml of methylene chloride, and 9.1 g of manganese dioxide is added under nitrogen. It is stirred overnight at room temperature, filtered on Celite and the residue is chromatographed on silica gel with ethyl acetate/hexane, whereby 301 mg of title compound 52 in addition to 395 mg of the starting material are obtained as colorless oils.

$^1$H-NMR (300 MHz, CDCl$_3$): δ=0.95 ppm (t, 3H); 1.37 (m, 2H); 1.60 (m, 2H); 2.43 (s, 3H); 2.65 (t, 2H); 5.94 (s, 1H); 6.12 (s, 1H); 7.18 (d, 2H); 7.22 (d, 2H)

1-[1-(4-Butylphenyl)cyclopropyl]ethanone 53

507 mg of sodium hydride (55% in paraffin oil) is introduced into 20 ml of dimethylformamide under nitrogen at 0° C., and 1.38 g of trimethylsulfonium iodide is added. After 30 minutes at this temperature, 1.06 g of ketone 52 is added in drops to 4 ml of dimethylformamide. It is stirred for 1 more hour at 0° C., then quenched with sodium chloride solution, extracted with ethyl acetate, dried on sodium sulfate and concentrated by evaporation. After chromatography on silica gel with ethyl acetate/hexane, 702 mg of title compound 53 is obtained as a colorless oil.

$^1$H-NMR (300 MHz, CDCl$_3$): δ=0.96 ppm (m, 2H); 1.17 (m, 2H); 1.37 (hex, 2); 1.59 (m, 2H); 1.60 (m, 2H); 2.64 (t, 2H); 2.02 (s, 3H); 7.17 (d, 2H); 7.29 (d, 2H)

EXAMPLE 10

(5Z,7E)-(1S,3R,24R)-25-(4-Methylphenyl)-26,27-cyclo-9,10-secocholesta-5,7,10(19),20(22)-tetraene-1,3,24-triol 59b, (5Z,7E,22E)-(1S,3R,24S)-25-(4-methylphenyl)-26,27-cyclo-9,10-secocholesta-5,7,10 (19),22-tetraene-1,3,24-triol 60a and (5Z,7E,22E)-(1S,3R,24R)-25-(4-methylphenyl)-26,27-cyclo-9,10-secocholesta-5,7,10(19),22-tetraene-1,3,24-triol 60b 1.01 ml of n-butyllithium solution (1.6 M in hexane) is added in drops at 0° C. to 0.33 ml of diisopropylamine in 10 ml of THF under nitrogen. It is stirred for 20 minutes at this temperature, cooled to −78° C., and then 440 mg of ketone 41 is added in drops to 2 ml of THF. After 1 hour at −78° C., 500 mg of aldehyde 30 in 10 ml of THF is added, and it is stirred for one more hour. The reaction mixture is then stirred into ice-cold ammonium chloride solution and extracted with ethyl acetate. After the organic phase is dried on sodium sulfate, the solvent is removed and chromatographed on silica gel with ethyl acetate/hexane, whereby 529 mg of (5Z,7E)-(1S,3R)-1,3-bis[[dimethyl(1,1-dimethylethyl)silyl]oxy]-22-hydroxy-25-(4-methylphenyl)-26,27-cyclo-9,10-secocholesta-5,7,10(19)-trien-24-one 54 is obtained as a colorless foam.

529 mg of 54 is dissolved in 20 ml of toluene, mixed with 0.34 ml of acetic anhydride, 0.49 ml of triethylamine as well as a spatula tip full of dimethylaminopyridine (DMAP), and it is stirred overnight under nitrogen at room temperature. Then, the reaction mixture is treated with sodium bicarbonate solution and extracted with ethyl acetate. After the organic phase is dried on sodium sulfate and after chromatography on silica gel with ethyl acetate/hexane, 439 mg of (5Z,7E)-(1S,3R)-22-(acetyloxy)-1,3-bis[[dimethyl(1,1-dimethylethyl)silyl]oxy]-25-(4-methylphenyl)-26,27-cyclo-9,10-secocholesta-5,7,10(19)-trien-24-one 55 is obtained as a colorless foam, which is dissolved in 20 ml of toluene and is stirred with 3 ml of 1,8-diazabicyclo[5.4.0]undec-7-ene (DBU) for 30 minutes at 40° C. under nitrogen. The reaction mixture is diluted with ethyl acetate and acidified with 0.01N hydrochloric acid. It is extracted with ethyl acetate, dried on sodium sulfate, and the solvent is removed, whereby 395 mg of (5Z,7E,22E)-(1S,3R)-1,3-bis[[dimethyl (1,1-dimethylethyl)silyl]oxy]-25-(4-methylphenyl)-26,27-cyclo-9,10-secocholesta-5,7,10(19),22-tetraen-24-one 56 is obtained as a colorless oil.

56: $^1$H-NMR (300 MHz, CDCl$_3$): δ=0.05 ppm (s, 6H); 0.49 (s, 3H); 0.89 (s, 18H); 0.97 (d, 3H); 1.11 (m, 4H); 2.38 (s, 3H); 4.19 (m, 1H); 4.38 (m, 1H); 4.86 (s, 1H); 5.18 (s, 1H); 5.99 (d, 1H); 6.01 (d, 1H); 6.22 (d, 1H); 6.63 (d, 1H); 7.15 (d, 2H); 7.22 (d, 2H)

395 mg of enone 56 is dissolved in 2 ml of THF and 4 ml of methanol and treated at 0° C. under nitrogen with 217 mg of cerium trichloride (heptahydrate). Then, 18 mg of sodium borohydride is added, and it is stirred for 2 more hours at 0° C. Ice water is now added, extracted with ethyl acetate and dried on sodium sulfate. The residue is chromatographed on silica gel with ethyl acetate/hexane, whereby in the elution sequence, 115 mg of (5Z,7E)-(1S,3R,24R)-1,3-bis[[dimethyl(1,1-dimethylethyl)silyl]oxy]-25-(4-methylphenyl)-26,27-cyclo-9,10-secocholesta-5,7,10(19), 20(22)-tetraen-24-ol 57b, 50 mg of (5Z,7E,22E)-(1S,3R,24S)-1,3-bis[[dimethyl(1,1-dimethylethyl)silyl]oxy]-25-(4-methylphenyl)-26,27-cyclo-9,10-secocholesta-5,7,10(19), 22-tetraen-24-ol 58a and 30 mg of (5Z,7E,22E)-(1S,3R,24R)-1,3-bis[[dimethyl(1,1-dimethylethyl)silyl]oxy]-25-(4-methylphenyl)-26,27-cyclo-9,10-secocholesta-5,7,10(19), 22-tetraen-24-ol 58b accumulate as colorless foams.

115 mg of 57b is dissolved in 15 ml of THF and stirred under nitrogen with 468 mg of tetrabutylammonium fluoride (trihydrate) overnight at room temperature. Saturated sodium bicarbonate solution is then added and extracted with ethyl acetate. The combined organic phases are washed with water, dried on sodium sulfate and concentrated by evaporation. Chromatography of the residue on silica gel with ethyl acetate/hexane yields 31 mg of title compound 59b as a colorless foam.

$^1$H-NMR (300 MHz, CD$_2$Cl$_2$): δ=0.41 ppm (s, 3H); 1.56 (s, 3H); 2.30 (s, 3H); 3.17 (m, 1H); 4.18 (m, 1H); 4.38 (m, 1H); 4.96 (s, 1H); 5.22 (t, 1H); 5.28 (s, 1H); 6.01 (d, 1H); 6.34 (d, 1H); 7.08 (d, 2H); 7.22 (d, 2H)

Analogously to 59b, title compounds 60a and 60b are obtained as colorless foams from 58a and 58b.

60a: $^1$H-NMR (300 MHz, CD$_2$Cl$_2$): δ=0.52 ppm (s, 3H); 0.99 (d, 3H); 2.28 (s, 3H); 3.67 (m, 1H); 4.18 (m, 1H); 4.38 (m, 1H); 4.96 (s, 1H); 5.28 (dd, 1H); 5.29 (s, 1H); 5.39 (dd, 1H); 6.01 (d, 1H); 6.36 (d, 1H); 7.08 (d, 1H); 7.19 (d, 1H)

60b: $^1$H-NMR (300 MHz, CD$_2$Cl$_2$): δ=0.53 ppm (s, 3H); 0.98 (d, 3H); 3.28 (s, 3H); 3.70 (m, 1H); 4.18 (m, 1H); 4.38 (m, 1H); 4.96 (s, 1H); 5.27 (dd, 1H); 5.29 (s, 1H); 5.37 (dd, 1H); 6.01 (d, 1H); 6.36 (d, 1H); 7.09 (d, 1H); 7.20 (d, 1H)

EXAMPLE 11

(5Z,7E)-(1S,3R,24R)-25-[4-(1-Methylethyl)phenyl]-26,27-cyclo-9,10-secocholesta-5,7,10(19),20(22)-tetraene-1,3,24-triol 66b, (5Z,7E,22E)-(1S,3R,24S)-25-[4-(1-methylethyl)-phenyl]-26,27-cyclo-9,10-secocholesta-5,7,10(19),22-tetraene-1,3,24-triol 67a and (5Z,7E,22E)-(1S,3R,24R)-25-[4-(1-methylethyl)phenyl]-26,27-cyclo-9,10-secocholesta-5,7,10(19), 22-tetraene-1,3,24-triol 67b 1.11 ml of n-butyllithium solution (1.6 M in hexane) is added in drops at 0° C. to 0.36 ml of diisopropylamine in 10 ml of THF under nitrogen. It is stirred for 20 minutes at this temperature, cooled to −78° C., and then 560 mg of ketone 47 is added in drops to 2 ml of THF. After 1 hour at −78° C., 500 mg of aldehyde 30 is added to 10 ml of THF, and it is stirred for 1 more hour. The reaction mixture is then treated with ammonium chloride solution and extracted with ethyl acetate. After the organic phase is dried on sodium sulfate, the solvent is removed and chromatographed on silica gel with ethyl acetate/hexane, whereby 497 mg of (5Z,7E)-(1S, 3R)-1,3-bis[[dimethyl(1,1-dimethylethyl)silyl]oxy]-22-hydroxy-25-[4-(1-methyl-ethyl)phenyl]-26,27-cyclo-9,10-secocholesta-5,7,10(19)-trien-24-one 61 is obtained as a colorless foam.

490 mg of 61 is dissolved in 20 ml of toluene, mixed with 0.30 ml of acetic anhydride, 0.44 ml of triethylamine as well as a spatula tip full of dimethylaminopyridine (DMAP), and it is stirred overnight under nitrogen at room temperature. Then, the reaction mixture is treated with sodium bicarbonate solution and extracted with ethyl acetate. After the organic phase is dried on sodium sulfate and after chromatography on silica gel with ethyl acetate/hexane, 379 mg of (5Z,7E)-(1S,3R)-22-(acetyloxy)-1,3-bis[[dimethyl(1,1-dimethylethyl)silyl]oxy]-25-[4-(1-methylethyl)phenyl]-26, 27-cyclo-9,10-secocholesta-5,7,10(19)-trien-24-one 62 is obtained as a colorless foam, which is dissolved in 20 ml of toluene and is stirred with 3 ml of 1,8-diazabicyclo[5.4.0] undec-7-ene (DBU) for 30 minutes at 40° C. under nitrogen. The reaction mixture is diluted with ethyl acetate and acidified with 0.01N hydrochloric acid. It is extracted with ethyl acetate, dried on sodium sulfate and the solvent is removed, whereby 355 mg of (5Z,7E,22E)-(1S,3R)-1,3-bis[[dimethyl(1,1-dimethylethyl)silyl]oxy]-25-[4-(1-methylethyl)phenyl]-26,27-cyclo-9,10-secocholesta-5,7,10 (19),22-tetraen-24-one 63 is obtained as a colorless oil.

63: $^1$H-NMR (300 MHz, CDCl$_3$): δ=0.06 ppm (s, 6H); 0.48 (s, 3H); 0.90 (s, 18H); 0.98 (d, 3H); 1.29 (d, 6H); 2.92 (hept, 1H); 4.18 (m, 1H); 4.37 (m, 1H); 4.85 (s, 1H); 5.18 (s, 1H); 5.95 (d, 1H); 6.00 (d, 1H); 6.22 (d, 1H); 6.60 (d, 1H); 7.20 (d, 2H); 7.23 (d, 2H).

350 mg of enone 63 is dissolved in 2 ml of THF and 4 ml of methanol and treated at 0° C. under nitrogen with 190 mg of cerium trichloride heptahydrate. Then, 16 mg of sodium borohydride is added, and it is stirred for 2 more hours at 0° C. Ice water is now added, extracted with ethyl acetate and dried on sodium sulfate. The residue is chromatographed on silica gel with ethyl acetate/hexane, whereby in the elution sequence, 27 mg of (5Z,7E)-(1S,3R,24R)-1,3-bis[[dimethyl (1,1-dimethylethyl)silyl]oxy]-25-[4-(1-methylethyl) phenyl]-26,27-cyclo-9,10-secocholesta-5,7,10(19),20(22)-tetraen-24-ol 64b, 40 mg of (5Z,7E,22E)-(1S,3R,24S)-1,3-bis[[dimethyl(1,1-dimethylethyl)silyl]oxy]-25-[4-(1-methylethyl)phenyl]-26,27-cyclo-9,10-secocholesta-5,7,10 (19),22-tetraen-24-ol 65a and 48 mg of (5Z,7E,22E)-(1S, 3R,24R)-1,3-bis[[dimethyl(1,1-dimethylethyl)silyl]oxy]-25-[4-(1-methylethyl)phenyl]-26,27-cyclo-9,10-secocholesta-5,7,10(19),22-tetraen-24-ol 65b accumulate as colorless foams.

27 mg of 64b is dissolved in 5 ml of THF and stirred under nitrogen with 112 mg of tetrabutylammonium fluoride (trihydrate) overnight at room temperature. Saturated sodium bicarbonate solution is then added and extracted with ethyl acetate. The combined organic phases are washed with water, dried on sodium sulfate and concentrated by evaporation. Chromatography of the residue on silica gel with ethyl acetate/hexane yields 12 mg of title compound 66b as a colorless foam.

$^1$H-NMR (300 MHz, CD$_2$Cl$_2$): δ=0.45 ppm (s, 3H); 1.23 (d, 6H); 1.56 (s, 3H); 2.86 (hept, 1H); 3.18 (m, 1H); 4.17 (m, 1H); 4.37 (m, 1H); 4.96 (s, 1H); 5.18 (s, 1H); 5.25 (t, 1H); 6.00 (d, 1H); 6.36 (d, 1H); 7.14 (d, 2H); 7.27 (d, 2H)

Analogously to 66b, title compounds 67a and 67b are obtained as colorless foams from 65a and 65b.

67a: $^1$H-NMR (300 MHz, CD$_2$Cl$_2$): δ=0.52 ppm (s, 3H); 0.98 (d, 3H); 1.20 (d, 6H); 2.86 (hept, 1H); 3.71 (m, 1H);

4.17 (m, 1H); 4.37 (m, 1H); 4.95 (s, 1H); 5.28 (s, 1H); 5.30 (dd, 1H); 5.39 (dd, 1H); 5.99 (d, 1H); 6.34 (d, 1H); 7.10 (d, 1H); 7.22 (d, 1H)

67b: $^1$H-NMR (300 MHz, CD$_2$Cl$_2$): δ=0.53 ppm (s, 3H); 0.99 (d, 3H), 1.21 (d, 6H); 2.86 (hept, 1H); 367 (m, 1H); 4.17 (m, 1H); 4.37 (m, 1H); 4.96 (s, 1H); 5.28 (s, 1H); 5.29 (dd, 1H); 5.38 (dd, 1H); 6.01 (d, 1H); 6.37 (d, 1H); 7.13 (d, 1H); 7.25 (d, 1H)

EXAMPLE 12

(5Z,7E)-(1S,3R,24R)-25-(4-Butylphenyl)-26,27-cyclo-9,10-secocholesta-5,7,10(19),20(22)-tetraene-1,3,24-triol 73b, (5Z,7E,22E)-(1S,3R,24S)-25-(4-butylphenyl)-26,27-cyclo-9,10-secocholesta-5,7,10 (19),22-tetraene-1,3,24-triol 74a, and (5Z,7E,22E)-(1S,3R,24R)-25-(4-butylphenyl)-26,27-cyclo-9,10-secocholesta-5,7,10(19),22-tetraene-1,3,24-triol 74b 1.28 ml of n-butyllithium solution (1.6 M in hexane) is added in drops at 0° C. to 0.42 ml of diisopropylamine in 10 ml of THF under nitrogen. It is stirred for 20 minutes at this temperature, cooled to −78° C. and then 692 mg of ketone 53 is added in drops to 4 ml of THF. After 1 hour at −78° C., 484 mg of aldehyde 30 is added to 10 ml of THF, and it is stirred for 1 more hour. The reaction mixture is then treated with ammonium chloride solution and extracted with ethyl acetate. After the organic phase is dried on sodium sulfate, the solvent is removed and chromatographed on silica gel with ethyl acetate/hexane, whereby 456 mg of (5Z,7E)-(1S,3R)-1,3-bis[[dimethyl(1,1-dimethylethyl)silyl]oxy]-25-(4-butylphenyl)-22-hydroxy-26,27-cyclo-9,10-secocholesta-5,7,10(19)-trien-24-one 68 is obtained as a colorless foam.

450 mg of 68 is dissolved in 18 ml of toluene, mixed with 0.27 ml of acetic anhydride, 0.40 ml of triethylamine and a spatula tip full of dimethylaminopyridine (DMAP), and it is stirred overnight under nitrogen at room temperature. Then, the reaction mixture is treated with sodium bicarbonate solution and extracted with ethyl acetate. After the organic phase is dried on sodium sulfate and after chromatography on silica gel with ethyl acetate/hexane, 399 mg of (5Z,7E)-(1S,3R)-22-(acetyloxy)-1,3-bis[[dimethyl(1,1-dimethylethyl)silyl]oxy]-25-(4-butylphenyl)-26,27-cyclo-9,10-secocholesta-5,7,10(19)-trien-24-one 69 is obtained as a colorless foam, which is dissolved in 18 ml of toluene and is stirred with 2.7 ml of 1,8-diazabicyclo[5.4.0]undec-7-ene (DBU) for 30 minutes at 40° C. under nitrogen. The reaction mixture is diluted with ethyl acetate and acidified with 0.01N hydrochloric acid. It is extracted with ethyl acetate, dried on sodium sulfate, and the solvent is removed, whereby 357 mg of (5Z,7E,22E)-(1S,3R)-1,3-bis[[dimethyl (1,1-dimethylethyl)silyl]oxy]-25-(4-butylphenyl)-26,27-cyclo-9,10-secocholesta-5,7,10(19),22-tetraen-24-one 70 is obtained as a colorless oil.

70: $^1$H-NMR (300 MHz, CDCl$_3$): δ=0.08 ppm (s, 6H); 0.48 (s, 3H); 0.89 (s, 18H); 0.93 (t, 3H); 0.95 (d, 3H); 2.62 (t, 2H); 4.19 (m, 1H); 4.38 (m, 1H); 4.86 (s, 1H); 5.18 (s, 1H); 5.97 (d, 1H); 6.00 (d, 1H); 6.22 (d, 1H); 6.63 (d, 1H); 7.16 (d, 2H); 7.22 (d, 2H)

350 mg of enone 70 is dissolved in 2 ml of THF and 4 ml of methanol and treated at 0° C. under nitrogen with 186 mg of cerium trichloride heptahydrate. Then, 16 mg of sodium borohydride is added, and it is stirred for 2 more hours at 0° C. Ice water is now added, extracted with ethyl acetate, and dried on sodium sulfate. The residue is chromatographed on silica gel with ethyl acetate/hexane, whereby in the elution sequence, 24 mg of (5Z,7E)-(1S,3R,24R)-1,3-bis[[dimethyl (1,1-dimethylethyl)silyl]oxy]-25-(4-butylphenyl)-26,27-cyclo-9,10-secocholesta-5,7,10(19),20(22)-tetraen-24-ol 71b, 40 mg of (5Z,7E,22E)-(1S,3R,24S)-1,3-bis[[dimethyl (1,1-dimethylethyl)silyl]oxy]-25-(4-butylphenyl)-26,27-cyclo-9,10-secocholesta-5,7,10(19),22-tetraen-24-ol 72a and 51 mg of (5Z,7E,22E)-(1S,3R,24R)-1,3-bis[[dimethyl (1,1-dimethylethyl)silyl]oxy]-25-(4-butylphenyl)-26,27-cyclo-9,10-secocholesta-5,7,10(19),22-tetraen-24-ol 72b accumulate as colorless foams.

24 mg of 71b is dissolved in 5 ml of THF, and stirred under nitrogen with 97 mg of tetrabutylammonium fluoride (trihydrate) overnight at room temperature. Saturated sodium bicarbonate solution is then added and extracted with ethyl acetate. The combined organic phases are washed with water, dried on sodium sulfate and concentrated by evaporation. Chromatography of the residue on silica gel with ethyl acetate/hexane yields 13 mg of title compound 73b as a colorless foam.

$^1$H-NMR (300 MHz, CD$_2$Cl$_2$): δ=0.42 ppm (s, 3H); 0.91 (t, 3H); 1.68 (s, 3H); 2.58 (t, 2H); 3.18 (m, 1H); 4.17 (m, 1H); 4.38 (m, 1H); 4.98 (s, 1H); 5.25 (t, 1H); 5.30 (s, 1H); 6.02 (d, 1H); 6.36 (d, 1H); 7.09 (d, 2H); 7.27 (d, 2H)

Analogously to 73b, title compounds 74a and 74b are obtained as colorless foams from 72a and 72b.

74a: $^1$H-NMR (300 MHz, CD$_2$Cl$_2$): δ=0.55 ppm (s, 3H); 0.92 (t, 3H); 0.98 (d, 3H); 2.58 (t, 2H); 3.71 (m, 1H); 4.16 (m, 1H); 4.37 (m, 1H); 4.97 (s, 1H); 5.29 (s, 1H); 5.31 (dd, 1H); 5.39 (dd, 1H); 6.00 (d, 1H); 6.36 (d, 1H); 7.08 (d, 1H); 7.23 (d, 1H)

74b: $^1$H-NMR (300 MHz, CD$_2$Cl$_2$): δ=0.56 ppm (s, 3H); 0.93 (t, 3H); 0.98 (d, 3H); 2.58 (t, 2H); 3.68 (m, 1H); 4.17 (m, 1H); 4.38 (m, 1H); 4.98 (s, 1H); 5.28 (dd, 1H); 5.29 (s, 1H); 5.38 (dd, 1H); 6.01 (d, 1H); 6.37 (d, 1H); 7.08 (d, 1H); 7.22 (d, 1H)

Synthesis of the Starting Materials in the 4-Alkyloxazole Series

2-(1-Bromocyclopropyl)-4-methyloxazole 77

7.45 g of N,N'-dicyclohexylcarbodiimide is added at 0° C. under nitrogen to a solution of 5.0 g of 1-bromocyclopropanecarboxylic acid 4 and 4.18 g of N-hydroxysuccinimide in 87 ml of methylene chloride, and it is stirred for 1.5 more hours. Then, 9.40 g of 2-aminopropionaldehyde dimethylacetal is added, and it is stirred for 2 hours at room temperature. After dilution with methylene chloride, it is filtered, concentrated by evaporation, and the residue is chromatographed on silica gel with ethyl acetate/hexane. 6.18 g of 1-bromo-N-[(2,2-dimethoxy-1-methyl)ethyl]-cyclopropane-1-carboxamide 75 is obtained as a colorless cloudy oil, which is taken up in 247 ml of acetonitrile and is stirred with 12.4 ml of 2N hydrochloric acid for 7 hours at room temperature. After sodium chloride solution is added, it is extracted with ethyl acetate, dried on sodium sulfate, and the solvent is removed. The residue is chromatographed on silica gel with ethyl acetate/hexane, whereby 3.83 g of 1-bromo-N-[(1-formyl) ethyl]cyclopropyl-1-carboxamide 76 accumulates.

3.43 g of amide 76, 5.54 g of hexachloroethane and 7.62 ml of triethylamine are dissolved in 47 ml of acetonitrile and cooled to −25° C. 6.14 g of triphenylphosphine is added, and it is stirred for 4.5 more hours at room temperature. It is now filtered, concentrated by evaporation, and the residue is chromatographed on silica gel with ethyl acetate/hexane, whereby 2.06 g of title compound 77 is obtained as a yellow oil.

$^1$H-NMR (300 MHz, CDCl$_3$): δ=1.50 ppm (m, 2H); 1.65 (m, 2H); 2.13 (s, 3H); 7.32 (s, 1H)

2-(1-Bromocyclopropyl)-4-ethyloxazole 80

7.45 g of N,N'-dicyclohexylcarbodiimide is added at 0° C. under nitrogen to a solution of 5.0 g of 1-bromocyclopropanecarboxylic acid 4 and 4.18 g of N-hydroxysuccinimide in 87 ml of methylene chloride, and it is stirred for 1.5 more hours. Then, 7.46 ml of 2-amino-1-butanol is added, and it is stirred for 2 hours at room temperature. After dilution with methylene chloride, it is filtered, concentrated by evaporation, and the residue is chromatographed on silica gel with ethyl acetate/hexane. 5.44 g of 1-bromo-N-[(1-hydroxymethyl)propyl]-cyclopropane-1-carboxamide 78 is obtained as a yellowish oil.

2.23 ml of oxalyl chloride in 102 ml of methylene chloride is mixed drop by drop at −78° C. under nitrogen with 3.6 ml of dimethylsulfoxide in 41 ml of methylene chloride. Then, 5.43 g of amide alcohol 78 in 41 ml of methylene chloride and, after 15 minutes, 14.3 ml of triethylamine are added in drops at −78° C. After another 30 minutes, sodium chloride solution is added, extracted with methylene chloride, dried on sodium sulfate and concentrated by evaporation. The residue is chromatographed on silica gel with ethyl acetate/hexane, whereby 3.4 g of 1-bromo-N-[(1-formyl)propyl]-cyclopropane-1-carboxamide 79 is obtained as a yellow oil, which is converted into title compound 80 analogously to the reaction of amide 76.

$^1$H-NMR (300 MHz, CDCl$_3$): δ=1.19 ppm (t, 3H); 1.50 (m, 2H); 1.62 (m, 2H); 2.50 (q, 2H); 7.29 (s, 1H)

2-(1-Bromocyclopropyl)-4-propyloxazole 81

Analogously to the synthesis of oxazole 80, title compound 81 is obtained with use of 2-aminopentanol.

$^1$H-NMR (300 MHz, CDCl$_3$): δ=0.92 ppm (t, 3H); 1.50 (m, 2H); 1.62 (m, 4H); 2.45 (t, 2H); 7.30 (s, 1H)

EXAMPLE 13

(5Z,7E,22E)-(1S,3R,24S)-25-(4-Methyloxazol-2-yl)-26,27-cyclo-9,10-secocholesta-5,7,10(19),22-tetraene-1,3,24-triol 83a and (5Z,7E,22E)-(1S,3R,24R)-25-(4-methyloxazol-2-yl)-26,27-cyclo-9,10-secocholesta-5,7,10(19),22-tetraene-1,3,24-triol 83b 2.75 ml of tert-butyllithium (1.7 M in pentane) is introduced at −20° C. under nitrogen into 8 ml of diethyl ether, cooled to −78° C., and 505 mg of 2-(1-bromocyclopropyl)-4-methyloxazole 77 is added in drops to 1.15 ml of diethyl ether. After 5 minutes, aldehyde 3 is added in drops to 3 ml of diethyl ether, it is stirred for 10 minutes at −78° C. and then allowed to reach 0° C. within 1.5 hours. Then, ammonium chloride solution is added, extracted with ethyl acetate, dried on sodium sulfate and concentrated by evaporation. The residue is chromatographed on silica gel with ethyl acetate/hexane, whereby in the elution sequence, 180 mg of (5Z,7E,22E)-(1S,3R,24S)-1,3-bis-[[dimethyl(1,1-dimethylethyl)silyl]oxy]-25-(4-methyloxazol-2-yl)-26,27-cyclo-9,10-secocholesta-5,7,10(19),22-tetraen-24-ol 82a and 180 mg of (5Z,7E,22E)-(1S,3R,24R)-1,3-bis-[[dimethyl(1,1-dimethylethyl)silyl]oxy]-25-(4-methyloxazol-2-yl)-26,27-cyclo-9,10-secocholesta-5,7,10(19),22-tetraen-24-ol 82b is obtained as colorless oils. 180 mg of disilyl ether 82a is dissolved in 7.3 ml of THF and stirred with 384 mg of tetrabutylammonium fluoride(trihydrate) overnight at room temperature under nitrogen. A mixture of sodium chloride and sodium bicarbonate solution is then added, extracted with ethyl acetate, the organic phase is washed with sodium chloride solution, dried on sodium sulfate, and the solvent is removed. The residue is chromatographed on silica gel with ethyl acetate/hexane, whereby 63 mg of title compound 83a is obtained as a colorless foam.

$^1$H-NMR (300 MHz, CDCl$_3$): δ=0.52 ppm (s, 3H); 1.00 (d, 3H); 1.05 (m, 4H); 2.11 (s, 3H); 4.10 (m, 2H); 4.23 (m, 1H); 4.43 (m, 1H); 5.00 (brs, 1H); 5.32 (brs, 1H); 5.42 (dd, 1H); 5.58 (dd, 1H); 6.00 (d, 1H); 6.38 (d, 1H); 7.18 (s, 1H)

Title compound 83b is analogously obtained as a colorless foam from disilyl ether 82b.

$^1$H-NMR (300 MHz, CDCl$_3$): δ=0.52 ppm (s, 3H); 0.98 (d, 3H); 1.05 (m, 4H), 2.08 (s, 3H); 4.08 (m, 1H); 4.21 (m, 1H); 4.40 (m, 1H); 4.48 (brs, 1H); 5.30 (brs, 1H); 5.40 (dd, 1H); 5.51 (dd, 1H); 5.98 (d, 1H); 6.35 (d, 1H); 7.18 (s, 1H)

EXAMPLE 14

(5Z,7E,22E)-(1S,3R,24R)-25-(4-Ethyloxazol-2-yl)-26,27-cyclo-9,10-secocholesta-5,7,10(19),22-tetraene-1,3,24-triol 84b Analogously to Example 13, title compound 84b is obtained as a colorless foam from aldehyde 3 and oxazole 80.

$^1$H-NMR (300 MHz, CDCl$_3$): δ=0.52 ppm (s, 3H); 0.98 (d, 3H); 1.08 (t, 3H); 2.48 (q, 2H); 4.09 (d, 1H); 4.23 (m, 1H); 4.43 (m, 1H); 4.47 (brs, 1H); 5.30 (brs, 1H); 5.40 (dd, 1H); 5.52 (dd, 1H); 6.00 (d, 1H); 6.36 (d, 1H); 7.15 (s, 1H)

EXAMPLE 15

(5Z,7E,22E)-(1S,3R,24R)-25-(4-Propyloxazol-2-yl)-26,27-cyclo-9,10-secocholesta-5,7,10(19),22-tetraene-1,3,24-triol 85b Analogously to Example 13, title compound 85b is obtained as a colorless foam from aldehyde 3 and oxazole 81.

$^1$H-NMR (300 MHz, CDCl$_3$): δ=0.50 ppm (s, 3H); 0.91 (t, 3H); 0.98 (d, 3H); 1.20 (m, 4H); 2.40 (t, 2H); 4.08 (d, 1H); 4.20 (m, 1H); 4.40 (m, 1H); 4.45 (brs, 1H); 5.28 (brs, 1H); 5.38 (dd, 1H); 5.50 (dd, 1H); 5.95 (d, 1H); 6.45 (d, 1H); 7.15 (s, 1H)

EXAMPLE 16

(5Z,7E,22E)-(1S,3R,24R)-25-(5-Butyloxazol-2-yl)-26,27-cyclo-9,10-secocholesta-5,7,10(19),22-tetraene-1,3,24-triol 88b 1-Bromo-N-(2-oxohexyl)-cyclopropane-1-carbamide 86 is produced analogously to amide 6, and converted into 2-(1-bromocyclopropyl)-5-butyloxazole 87 as described for compound 8.

87: $^1$H-NMR (300 MHz, CDCl$_3$): δ=0.92 ppm (t, 3H); 1.40 (m, 2H); 1.50 (m, 2H); 1.60 (m, 4H); 2.60 (t, 2H); 6.65 (s, 1H)

Analogously to Example 1, title compound 88b is obtained as a colorless foam from aldehyde 3 and oxazole 87.

$^1$H-NMR (300 MHz, CDCl$_3$): δ=0.57 ppm (s, 3H); 0.90 (t, 3H); 0.97 (m, 2H); 1.05 (d, 3H); 1.15 (m, 2H); 2.58 (m, 3H); 4.12 (d, 1H); 4.23 (m, 1H); 4.43 (m, 1H); 5.00 (brs, 1H); 5.32 (brs, 1H); 5.42 (dd, 1H); 5.53 (dd, 1H); 6.00 (d, 1H); 6.38 (d, 1H); 6.58 (s, 1H)

Starting Materials in the 5-Alkyl-Thiazole Series

2-(1-Bromocyclopropyl)-5-butylthiazole 89

500 mg of amide 86 and 212 mg of phosphorus pentasulfide are heated in 2 ml of dioxane for 25 minutes to 100° C. and, after cooling, poured into dilute sodium hydroxide solution. After extraction with ethyl acetate and drying on sodium sulfate, it is concentrated by evaporation, and the oily residue is chromatographed on silica gel with ethyl acetate/hexane. 240 mg of title compound 89 is obtained as a colorless oil.

$^1$H-NMR (300 MHz, CDCl$_3$): δ=0.92 ppm (t, 3H); 1.48 (m, 2H); 1.65 (m, 6H); 2.75 (t, 2H); 7.32 (s, 1H)

2-(1-Bromocyclopropyl)-5-ethylthiazole 90

Analogously to the production of thiazole 89, title compound 90 is obtained as a colorless oil from amide 9.

$^1$H-NMR (300 MHz, CDCl$_3$) δ=1.28 ppm (t, 3H); 1.58 (m, 2H); 1.70 (m, 2H); 2.80 (q, 2H); 7.32 (s, 1H)

EXAMPLE 17

(5Z,7E,22E)-(1S,3R,24S)-25-(5-Butylthiazol-2-yl)-26,27-cyclo-9,10-secocholesta-5,7,10(19),22-tetraene-1,3,24-triol 92a and (5Z,7E,22E)-(1S,3R,24R)-25-(5-butylthiazol-2-yl)-26,27-cyclo-9,10-secocholesta-5,7,10(19),22-tetraene-1,3,24-triol 92b 5.9 ml of tert-butyllithium (1.7 M in pentane) is added at −78° C. under nitrogen to 16 ml of Trapp mixture (THF/diethyl ether/pentane 4:1:1). At −116° C., 1.3 g of thiazole 89 is added in drops to 2.4 ml of Trapp mixture. After 1 hour, 1.0 g of aldehyde 3 is added to 6.4 ml of Trapp mixture, and it is stirred for 1 hour at −116° C. and for 1 hour at −78° C. It is then quenched with ammonium chloride solution, extracted with diethyl ether and dried on sodium sulfate. After concentration by evaporation, the residue is chromatographed on silica gel with ethyl acetate/hexane, whereby in the elution sequence, 470 mg of (5Z,7E,22E)-(1S,3R,24S)-1,3-bis-[[dimethyl(1,1-dimethylethyl)silyl]oxy]-25-(5-butylthiazol-2-yl)-26,27-cyclo-9,10-secocholesta-5,7,10(19),22-tetraen-24-ol 91a and 440 mg of (5Z,7E,22E)-(1S,3R,24R)-1,3-bis-[[dimethyl(1,1-dimethylethyl)silyl]oxy]-25-(5-butylthiazol-2-yl)-26,27-cyclo-9,10-secocholesta-5,7,10(19),22-tetraen-24-ol 91b accumulate as yellow oils.

460 mg of disilyl ether 91a is dissolved in 17 ml of THF and treated under nitrogen with 900 mg of tetrabutylammonium fluoride(trihydrate). It is stirred overnight and then a mixture of sodium chloride and sodium bicarbonate solution is added. Then, it is extracted with ethyl acetate, the organic phase is washed with sodium chloride solution, dried on sodium sulfate and concentrated by evaporation. The residue is chromatographed on silica gel, whereby 139 mg of title compound 92a is obtained as a colorless foam.

92a: $^1$H-NMR (300 MHz, CDCl$_3$): δ=0.52 ppm (s, 3H); 0.92 (t, 3H); 0.98 (d, 3H); 1.08 (m, 4H); 2.75 (t, 2H); 4.00 (d, 1H); 4.23 (m, 1H); 4.43 (m, 1H); 5.00 (brs, 1H); 5.32 (brs, 1H); 5.40 (dd, 1H); 5.55 (dd, 1H); 6.00 (d, 1H); 6.38 (d, 1H); 7.25 (s, 1H)

Title compound 92b is obtained analogously as a colorless foam from disilyl ether 91b.

92b: $^1$H-NMR (300 MHz, CDCl$_3$): δ=0.52 ppm (s, 3H); 0.92 (t, 3H); 0.98 (d, 3H); 1.08 (m, 4H); 2.75 (t, 2H); 4.00 (d, 1H); 4.23 (m, 1H); 4.43 (m, 1H); 5.00 (brs, 1H); 5.32 (brs, 1H); 5.40 (dd, 1H); 5.55 (dd, 1H); 6.00 (d, 1H); 6.38 (d, 1H); 7.25 (s, 1H)

EXAMPLE 18

(5Z,7E,22E)-(1S,3R,24R)-25-(5-Ethylthiazol-2-yl)-26,27-cyclo-9,10-secocholesta-5,7,10(19),22-tetraene-1,3,24-triol 93b Analogously to Example 17, starting from aldehyde 3, the title compound is obtained as a colorless foam with thiazole 90.

$^1$H-NMR (300 MHz, CDCl$_3$): δ=0.52 ppm (s, 3H); 0.98 (d, 3H); 1.08 (m, 4H); 1.28 (t, 3H); 2.80 (q, 2H); 4.01 (d, 1H); 4.23 (m, 1H); 4.43 (m, 1H); 5.00 (brs, 1H); 5.32 (brs, 1H); 5.40 (dd, 1H); 5.52 (dd, 1H); 6.00 (d, 1H); 6.37 (d, 1H); 7.28 (s, 1H)

EXAMPLE 19

(5Z,7E,22E)-(1S,3R,24S)-25-(3-Butyl-1,2,4-oxadiazol-5-yl)-26,27-cyclo-9,10-secocholesta-5,7,10(19),22-tetraene-1,3,24-triol 95a 28 mg of sodium is dissolved in 0.8 ml of methanol, and 200 mg of (5Z,7E,22E)-(1S,3R,24S)-1,3-bis-[[dimethyl(1,1-dimethylethyl)silyl]oxy]-24-hydroxy-26,27-cyclo-9,10-secocholesta-5,7,10(19),22-tetraene-25-carboxylic acid methyl ester 94a (for production, see DE 42 34 382) is added under nitrogen to 0.8 ml of methanol and 55 mg of valerylamidoxime [K. P. Flora et al. Cancer Res. 1291 (1978)] and heated to boiling for 9.25 hours. The reaction mixture is added to sodium chloride solution, extracted with ethyl acetate, and the organic phase is washed with sodium chloride solution. After drying with sodium sulfate and concentration by evaporation, the oily residue is purified chromatographically on silica gel with ethyl acetate/hexane, whereby 40 mg of title compound 95a is obtained as a colorless foam.

$^1$H-NMR (300 MHz, CDCl$_3$): δ=0.52 ppm (s, 3H); 0.95 (t, 3H); 1.02 (d, 3H); 1.20 (m, 4H); 2.68 (t, 2H); 4.23 (m, 2H); 4.43 (m, 1H); 5.00 (brs, 1H); 5.32 (brs, 1H); 5.42 (dd, 1H); 5.62 (dd, 1H); 6.00 (d, 1H); 6.38 (d, 1H)

EXAMPLE 20

(5Z,7E,22E)-(1S,3R,24R)-25-(3-Butyl-1,2,4-oxadiazol-5-yl)-26,27-cyclo-9,10-secocholesta-5,7,10(19),22-tetraene-1,3,24-triol 95b Analogously to Example 20, starting from (5Z,7E,22E)-(1S,3R,24R)-1,3-bis-[[dimethyl(1,1-dimethylethyl)silyl]oxy]-24-hydroxy-26,27-cyclo-9,10-secocholesta-5,7,10(19),22-tetraene-25-carboxylic acid methyl ester 94b (for production, see DE 42 34 382), title compound 95b is obtained as a colorless foam.

$^1$H-NMR (300 MHz, CDCl$_3$): δ=0.52 ppm (s, 3H); 0.92 (t, 3H); 1.03 (d, 3H); 1.20 (m, 4H); 2.70 (t, 2H); 3.55 (brd, 1H); 4.23 (m, 2H); 4.43 (m, 1H); 5.00 (brs, 1H); 5.32 (brs, 1H); 5.43 (dd, 1H); 5.58 (dd, 1H); 6.00 (d, 1H); 6.38 (d, 1H)

EXAMPLE 21

(5Z,7E,22E)-(1S,3R,24R)-25-(3-Ethyl-1,2,4-oxadiazol-5-yl)-26,27-cyclo-9,10-secocholesta-5,7,10(19),22-tetraene-1,3,24-triol 96b Analogously to Example-20, starting from (5Z,7E,22E)-(1S,3R,24R)-1,3-bis-[[dimethyl(1,1-dimethylethyl)silyl]oxy]-24-hydroxy-26,27-cyclo-9,10-secocholesta-5,7,10(19),22-tetraene-25-carboxylic acid methyl ester 94b (for production, see DE 42 34 382), title compound 96b is obtained as a colorless foam with propionamidoxime [K. P. Flora et al. Cancer Res. 1291 (1978)].

$^1$H-NMR (300 MHz, CDCl$_3$): δ=0.52 ppm (s, 3H); 1.02 (d, 3H); 1.20 (m, 4H); 1.32 (t, 3H); 2.75 (q, 2H); 4.23 (m, 2H); 4.43 (m, 1H); 5.00 (brs, 1H); 5.32 (brs, 1H); 5.43 (dd, 1H); 5.58 (dd, 1H); 6.00 (d, 1H); 6.38 (d, 1H)

Starting Materials for the 25-Pyridyl Series 2-(1-Bromocyclopropyl)-pyridine 100

10.0 g of 1-bromocyclopropanecarboxylic acid 4, 7.0 g of 2-pyridine thiol and 13.8 g of N,N'-dicyclohexylcarbodiimide are dissolved in 150 ml of ethyl acetate and stirred for 2 hours under nitrogen at room temperature. After sodium chloride solution is added, it is extracted with ethyl acetate, the organic phase is washed with saturated sodium chloride solution, dried on sodium sulfate and concentrated by evaporation. The oily residue is chromatographed on silica gel with ethyl acetate/hexane, whereby 8.25 g of 1-bromo-S-(2-pyridyl)-cyclopropanethioate 97 is obtained as a yellow oil. 10.11 g of thioester 97 in 26 ml of THF is mixed drop by drop at 0° C. with 3-(1,3-dioxolan-2-yl)-propylmagnesium bromide 98 [D. Wenkert et al. J. org. Chem. 50, 4114 (1985)]. After 3 hours at room temperature, the suspension in stirred into ammonium chloride solution and extracted with ethyl acetate. It is dried on sodium sulfate, concentrated by evaporation, and the residue is chromatographed on silica gel with ethyl acetate/hexane, whereby 7.92 g of 1-(1-bromocyclopropyl)-4-(1-dioxolan-2-yl)-butan-1-one 99 is obtained as a colorless oil. 6.68 g of ketone 99 in 76 ml of acetic acid is heated to boiling with 5.08 g of hydroxylamine hydrochloride for 1 hour under nitrogen. After the acetic acid is evaporated, the oily residue is mixed with ice and made basic with about 20% sodium hydroxide solution. Then, it is diluted with sodium chloride solution and extracted with ethyl acetate. The organic phase is dried on sodium sulfate and concentrated by evaporation. The residue is chromatographed on silica gel with ethyl acetate/hexane, whereby 2.73 g of title compound 100 is obtained as a light yellow oil.

$^1$H-NMR (300 MHz, CDCl$_3$): δ=1.55 ppm (m, 2H); 1.68 (m, 2H); 7.10 (m, 1H); 7.65 (m, 1H); 7.75 (m, 1H); 8.48 (m, 1H)

2-(1-Bromocyclopropyl)-6-methylpyridine 103

Starting from 1-(1-bromocyclopropyl)-5,5-ethylenedioxyhexan-1-one 102, which is obtained by reaction of thioester 97 with Grignard reagent 101 [S. Borrelly, L. A. Paquette J. Am. Chem. Soc. 118, 727 (1996), T. E. Bellas et al. Tetrahedron 25, 5149 (1969)], title compound 103 is produced analogously to 99.

$^1$H-NMR (300 MHz, CDCl$_3$): δ=1.50 ppm (m, 2H); 1.65 (m, 2H); 2.50 (s, 3H); 6.98 (m, 1H); 7.52 (m, 2H)

EXAMPLE 22

(5Z,7E,22E)-(1S,3R,24S)-25-(2-Pyridyl)-26,27-cyclo-9,10-secocholesta-5,7,10(19),22-tetraene-1,3,24-triol 105a and (5Z,7E,22E)-(1S,3R,24R)-25-(2-pyridyl)-26,27-cyclo-9,10-secocholesta-5,7,10(19),22-tetraene-1,3,24-triol 105b At −20° C., 8.5 ml of tert-butyllithium (1.7 M in pentane) is added under nitrogen to 24 ml of diethyl ether. At −78° C., 1.34 g of 100 is added in drops to 3.2 ml of diethyl ether, and it is stirred for 30 minutes at −78° C. Then, 1.34 g of aldehyde 3 is added in drops to 8.3 ml of diethyl ether, stirred for another 30 minutes at −78° C. and then allowed to reach 0° C. within 90 minutes. Then, it is quenched with ammonium chloride solution, extracted with ethyl acetate, dried on sodium sulfate and concentrated by evaporation. The residue is chromatographed on silica gel with ethyl acetate/hexane, whereby in the elution sequence, 120 mg of (5Z,7E,22E)-(1S,3R,24S)-1,3-bis-[[dimethyl(1,1-dimethylethyl)-silyl]oxy]-25-(2-pyridyl)-26,27-cyclo-9,10-secocholesta-5,7,10(19),22-tetraen-24-ol 104a and 100 mg of (5Z,7E,22E)-(1S,3R,24R)-1,3-bis-[[dimethyl(1,1-dimethylethyl)-silyl]oxy]-25-(2-pyridyl)-26,27-cyclo-9,10-secocholesta-5,7,10(19),22-tetraen-24-ol 104b are obtained as colorless foams in each case.

120 mg of disilyl compound 104a is dissolved in 4.8 ml of THF and stirred with 257 mg of tetrabutylammonium fluoride(trihydrate) under nitrogen overnight at room temperature. The reaction mixture is then poured into a mixture of sodium chloride and sodium bicarbonate solution, extracted with ethyl acetate, the organic phase is washed with sodium chloride solution, dried on sodium sulfate and concentrated by evaporation. The residue is chromatographed on silica gel with ethyl acetate/hexane, whereby 19 mg of title compound 105a accumulates as a colorless foam.

105a: $^1$H-NMR (300 MHz, CDCl$_3$): δ=0.48 ppm (s, 3H); 0.88 (m, 4H); 0.95 (d, 3H); 3.88 (d, 1H); 4.23 (m, 2H); 4.43 (m, 1H); 4.98 (brs, 1H); 5.32 (brs, 1H); 5.38 (dd, 1H); 5.50 (dd, 1H); 5.98 (d, 1H); 6.38 (d, 1H); 6.98 (d, 1H); 7.12 (brt, 1H); 7.60 (brt, 1H); 8.45 (d, 1H)

Disilyl ether 104b is treated analogously with tetrabutylammonium fluoride(trihydrate), whereby title compound 105b is obtained as a colorless foam.

105b: $^1$H-NMR (300 MHz, CDCl$_3$): δ=0.50 ppm (s, 3H); 0.88 (m, 4H); 0.95 (d, 3H); 3.88 (d, 1H); 4.23 (m, 2H); 4.43 (m, 1H); 4.98 (brs, 1H); 5.32 (brs, 1H); 5.40 (m, 2H); 6.00 (d, 1H); 6.38 (d, 1H); 6.98 (d, 1H); 7.12 (brt, 1H); 7.60 (brt, 1H); 8.45 (d, 1H)

EXAMPLE 23

(5Z,7E,22E)-(1S,3R,24R)-25-(6-Methyl-2-pyridyl)-26,27-cyclo-9,10-secocholesta-5,7,10(19),22-tetraene-1,3,24-triol 106b Analogously to Example 22, starting from aldehyde 3, title compound 106b is obtained as a colorless foam with pyridine derivative 103.

$^1$H-NMR (300 MHz, CDCl$_3$): δ=0.50 ppm (s, 3H); 0.85 (m, 4H); 0.95 (d, 3H); 2.51 (s, 3H); 3.80 (d, 1H); 4.23 (m, 2H); 4.43 (m, 1H); 4.98 (brs, 1H); 5.32 (brs, 1H); 5.40 (m, 2H); 5.48 (d, 1H); 6.38 (d, 1H); 6.45 (d, 1H); 6.70 (d, 1H); 7.48 (t, 1H)

Starting Materials in the 25-Oxazoline Series 2-(1-Bromocyclopropyl)-5,5-dimethyl-2-oxazoline 109

47 g of carboxylic acid 4 is mixed under nitrogen with 78 ml of thionyl chloride, and it is stirred overnight at room temperature. Then, excess thionyl chloride is distilled off, and the residue is fractionated in an oil pump vacuum, whereby 44.74 g of 1-bromocyclopropane-carboxylic acid chloride 107 accumulates as a colorless oil (boiling point 35–37° C., 0.05 mm).

$^1$H-NMR (300 MHz, CDCl$_3$): δ=1.69 ppm (m, 2H); 2.09 (m, 2H)

1.69 g of 2-amino-2-methyl-1-propanol is introduced into 85 ml of methylene chloride under nitrogen at room temperature, and 2.38 g of sodium carbonate is added to 38 ml of water and then 3.6 g of acid chloride 107. It is stirred overnight at room temperature and then treated with methanolic 2N sodium hydroxide solution. The organic phase is separated, dried on sodium sulfate and concentrated by evaporation. The residue is chromatographed on silica gel with ethyl acetate/hexane, whereby 3.83 g of 1-bromocyclopropanecarboxylic acid-1,1-dimethyl-2-hydroxy-ethylamide 108 is obtained as a colorless oil.

$^1$H-NMR (300 MHz, CDCl$_3$): δ=1.32 ppm (m, 2H); 1.33 (s, 6H); 1.68 (m, 2H); 3.61 (d, 2H); 4.25 (t, 1H); 6.87 (brs, 1H)

800 mg of amide 107 is dissolved in 8 ml of toluene, and 3 ml of phosphorus oxychloride is added in drops at room temperature under nitrogen. After 30 minutes, it is concentrated by evaporation, the residue is taken up in methylene chloride and stirred vigorously with 10 ml of sodium carbonate solution (10%) for 30 minutes. The phases are separated, the organic phase is dried on sodium sulfate, filtered and concentrated by evaporation, whereby 750 mg of title compound 109 accumulates as a colorless oil.

$^1$H-NMR (300 MHz, CDCl$_3$): δ=1.29 ppm (s, 6H), 1.38 (m, 2H); 1.58 (m, 2H); 4.01 (s, 2H)

(5R)-2-(1-Bromocyclopropyl)-5-phenyl-2-oxazoline 111

739 mg of D-(−)-α-phenylglycinol is dissolved in 27 ml of methylene chloride, and 678 mg of sodium carbonate is added to 11 ml of water and 1.09 g of acid chloride 107 at room temperature. It is stirred overnight and then mixed with methanolic sodium hydroxide solution, the organic phase is separated, dried on sodium sulfate and concentrated by evaporation. The residue is chromatographed on silica gel with ethyl acetate/hexane, whereby 1.09 g of (1R)-1-bromocyclopropanecarboxylic acid-2-hydroxy-1-phenylethylamide 110 is isolated as a colorless oil.

$^1$H-NMR (300 MHz, CDCl$_3$): δ=1.35 ppm (s, 2H); 1.70 (m, 2H); 2.30 (t, 1H); 3.90 (t, 2H); 5.03 (m, 1H); 7.37 (m, 5H); 7.52 (brs, 1H)

Analogously to 107, amide 110 is converted into title compound 111.

$^1$H-NMR (300 MHz, CDCl$_3$): δ=1.46 ppm (m, 2H); 1.69 (m, 2H); 4.21 (t, 1H); 4.72 (dd, 1H); 5.23 (dd, 1H); 7.30 (m, 5H)

2-(1-Bromocyclopropyl)-5-methyl-2-oxazoline 113

Analogously to the production of amide 110, 2.18 g of acid chloride 107 is reacted with 780 mg of DL-2-amino-1-propanol, whereby 1.7 g of 1-bromocyclopropanecarboxylic acid-2-hydroxy-1-methylethylamide 112 is obtained as a colorless oil.

$^1$H-NMR (300 MHz, CDCl$_3$): δ=1.22 ppm (d, 3H); 1.32 (m, 2H); 1.70 (m, 2H); 2.60 (t, 1H); 3.58 (m, 1H); 3.69 (m, 1H); 4.03 (m, 1H); 6.92 (brs, 1H)

Analogously to 107, amide 112 is converted into title compound 113.

$^1$H-NMR (300 MHz, CDCl$_3$): δ=1.28 ppm (d, 3H); 1.40 (m, 2H); 1.59 (m, 2H); 3.87 (t, 2H); 4.22 (m, 1H); 4.44 (dd, 1H)

5(R)-2-(1-Bromocyclopropyl)-5-ethyl-2-oxazoline 115

Analogously to the production of amide 110, 2.18 g of acid chloride 107 is reacted with 962 mg of (−)-2-amino-1-butanol, whereby 2.3 g of (1R)-1-bromocyclopropanecarboxylic acid-2-hydroxy-1-ethylethylamide 114 is obtained as a colorless oil.

$^1$H-NMR (300 MHz, CDCl$_3$): δ=0.98 ppm (t, 3H); 1.32 (m, 2H); 1.70 (m, 2H); 2.60 (t, 1H); 3.58 (m, 1H); 3.69 (m, 1H); 4.03 (m, 1H); 6.92 (brs, 1H)

Analogously to 107, amide 114 is converted into title compound 115.

$^1$H-NMR (300 MHz, CDCl$_3$): δ=0.92 ppm (t, 3H); 1.38 (m, 2H); 1.58 (m, 2H); 1.70 (m, 2H); 3.98 (t, 1H); 4.38 (dd, 1H); 6.90 (brs, 1H)

25-Oxazoline Series

EXAMPLE 24

(5Z,7E,22E)-(1S,3R,24S)-25-(5,5-Dimethyl-2-oxazolin-2-yl)-26,27-cyclo-9,10-secocholesta-5,7,10 (19),22-tetraene-1,3,24-triol 117a and (5Z,7E,22E)-(1S,3R,24R)-25-(5,5-dimethyl-2-oxazolin-2-yl)-26, 27-cyclo-9,10-secocholesta-5,7,10(19),22-tetraene-1, 3,24-triol 117b 2.16 ml of tert-butyllithium is introduced under nitrogen into 6 ml of diethyl ether, and it is cooled to −78° C. 430 mg of oxazoline 109 is added in drops to 1 ml of diethyl ether, and it is stirred for 5 more minutes. Then, 400 mg of aldehyde 3 is added to 1 ml of diethyl ether. It is allowed to reach 0° C. within 1.5 hours, and it is hydrolyzed with ammonium chloride solution. After extraction with ethyl acetate and drying on sodium sulfate, it is concentrated by evaporation, and the residue is chromatographed on silica gel with ethyl acetate/hexane, whereby 90 mg of (5Z,7E, 22E)-(1S,3R,24S)-1,3-bis-[[dimethyl(1,1-dimethylethyl) silyl]oxy]-25-(5,5-dimethyl-2-oxazolin-2-yl)-26,27-cyclo-9,10-secocholesta-5,7,10(19),22-tetraen-24-ol 116a and 50 mg of (5Z,7E,22E)-(1S,3R,24R)-1,3-bis-[[dimethyl(1,1-dimethylethyl)-silyl]oxy]-25-(5,5-dimethyl-2-oxazolin-2-yl)-26,27-cyclo-9,10-secocholesta-5,7,10(19),22-tetraen-24-ol 116b are obtained one right after the other as colorless foams.

116a: $^1$H-NMR (300 MHz, CDCl$_3$): δ=0.07 ppm (s, 6H); 0.53 (s, 3H); 0.88 (s, 18H); 1.02 (d, 3H); 1.28 (s, 6H); 3.80 (d, 1H); 3.86 (d, 1H); 3.97 (d, 1H); 4.18 (m, 1H); 4.38 (m, 1H); 4.88 (brs, 1H); 4.98 (brs, 1H); 5.19 (brs, 1H); 5.40 (dd, 1H); 5.56 (dd, 1H); 6.01 (d, 1H); 6.23 (d, 1H)

116b: $^1$H-NMR (300 MHz, CDCl$_3$): δ=0.07 ppm (s, 6H); 0.53 (s, 3H); 0.88 (s, 18H); 1.03 (d, 3H); 1.28 (s, 3H); 3.80 (d, 1H); 3.86 (d, 1H); 3.94 (d, 1H); 4.18 (m, 1H); 4.38 (m, 1H); 4.88 (brs, 1H); 4.98 (brs, 1H); 5.19 (brs, 1H); 5.40 (dd, 1H); 5.50 (dd, 1H); 6.01 (d, 1H); 6.23 (d, 1H)

90 mg of the disilyl ether is dissolved in 10 ml of THF, 156 mg of tetrabutylammonium fluoride(trihydrate) is added and stirred under nitrogen for 12 hours at room temperature. The reaction mixture is poured into water, extracted with ethyl acetate, dried on sodium sulfate and concentrated by evaporation. The residue is chromatographed on silica gel with ethyl acetate/hexane, whereby 36 mg of title compound 117a is obtained as a colorless foam.

$^1$H-NMR (300 MHz, CDCl$_3$): δ=0.58 ppm (s, 3H); 0.78 (m, 2H); 0.84 (m, 2H); 1.02 (d, 3H); 1.28 (s, 6H); 3.80 (d, 1H); 3.84 (d, 1H); 3.97 (d, 1H); 4.22 (m, 1H); 4.42 (m, 1H); 5.00 (brs, 1H); 5.33 (brs, 1H); 5.39 (dd, 1H); 5.55 (dd, 1H); 6.01 (d, 1H); 6.38 (d, 1H)

Analogously, disilyl ether 116b is converted into title compound 117b.

$^1$H-NMR (300 MHz, CDCl$_3$): δ=0.58 ppm (s, 3H); 0.78 (m, 2H); 0.84 (m, 2H); 1.03 (d, 1H); 1.28 (s, 6H); 3.80 (d, 1H); 3.84 (d, 1H); 3.92 (d, 1H); 4.22 (m, 1H); 4.42 (m, 1H), 5.00 (brs, 1H); 5.32 (brs, 1H); 5.40 (dd, 1H); 5.50 (dd, 1H); 6.01 (d, 1H); 6.38 (d, 1H)

EXAMPLE 25

(5Z,7E,22E)-[1S,3R,24S,25(R)]-25-(5-Phenyl-2-oxazolin-2-yl)-26,27-cyclo-9,10-secocholesta-5,7,10 (19),22-tetraene-1,3,24-triol 119a and (5Z,7E,22E)-[1S,3R,24R,25(R)]-25-(5-phenyl-2-oxazolin-2-yl)-26,27-cyclo-9,10-secocholesta-5,7,10(19),22-tetraene-1,3,24-triol 119b 1.84 ml of tert-butyllithium.is introduced under nitrogen into 5 ml of diethyl ether, and it is cooled to −78° C. 450 mg of oxazoline 111 is added in drops to 1 ml of diethyl ether, and it is stirred for 5 more minutes. Then, 337 mg of aldehyde 3 is added to 1 ml of diethyl ether. It is allowed to reach 0° C. within 1.5 hours and hydrolyzed with ammonium chloride solution. After extraction with ethyl acetate and drying on sodium sulfate, it is concentrated by evaporation, and the residue is chromatographed on silica gel with ethyl acetate/hexane, whereby 110 mg of (5Z,7E, 22E)-[1S,3R,24S,25(R)]-1,3-bis-([dimethyl(1,1-dimethylethyl)silyl]oxy]-25-(5-phenyl-2-oxazolin-2-yl)-26, 27-cyclo-9,10-secocholesta-5,7,10(19),22-tetraen-24-ol 118a and 100 mg of (5Z,7E,22E)-[1S,3R,24R,25(R)]-1,3-bis-[[dimethyl(1,1-dimethylethyl)-silyl]oxy]-25-(5-phenyl-2-oxazolin-2-yl)-26,27-cyclo-9,10-secocholesta-5,7,10(19), 22-tetraen-24-ol 118b are obtained as colorless foams.

110 mg of disilyl ether 118a is dissolved in 15 ml of THF, 182 mg of tetrabutylammonium fluoride(trihydrate) is added and stirred under nitrogen for 12 hours at room temperature. The reaction mixture is poured into water, extracted with ethyl acetate, dried on sodium sulfate and concentrated by evaporation. The residue is chromatographed on silica gel with ethyl acetate/hexane, whereby 36 mg of title compound 119a is obtained as a colorless foam.

$^1$H-NMR (300 MHz, CDCl$_3$): δ=0.58 ppm (s, 3H); 0.88 (m, 2H); 0.92 (m, 2H); 1.06 (d, 3H); 4.00 (t, 1H); 4.01 (m, 1H); 4.22 (m, 1H); 4.42 (m, 1H); 4.53 (dd, 1H); 4.82 (brs, 1H) 5.00 (brs, 1H); 5.22 (dd, 1H); 5.33 (brs, 1H), 5.50 (dd, 1H); 5.62 (dd, 1H); 6.01 (d, 1H); 6.38 (d, 1H); 7.30 (m, 5H)

Disilylether 118b is analogously converted into title compound 119b.

$^1$H-NMR (300 MHz, CDCl$_3$): δ=0.58 ppm (s, 3H); 0.88 (m, 2H); 0.94 (m, 2H); 1.07 (d, 3H); 3.98 (t, 1H); 4.02 (m, 1H); 4.22 (m, 1H); 4.42 (m, 1H); 4,55 (dd, 1H); 4.90 (brs, 1H): 5.00 (brs, 1H); 5.22 (dd, 1H); 5.32 (brs, 1H), 5.50 (m, 2H); 6.01 (d, 1H); 6.38 (d, 1H); 7.30 (m, 5H)

EXAMPLE 26

(5Z,7E,22E)-(1S,3R,24S)-25-(5-Methyl-2-oxazolin-2-yl)-26,27-cyclo-9,10-secocholesta-5,7,10(19),22-tetraene-1,3,24-triol 121a and (5Z,7E,22E)-(1S,3R, 24R)-25-(5-methyl-2-oxazolin-2-yl)-26,27-cyclo-9, 10-secocholesta-5,7,10(19),22-tetraene-1,3,24-triol 121b 1.84 ml of tert-butyllithium is introduced under nitrogen into 5 ml of diethyl ether, and it is cooled to −78° C. 350 mg of oxazoline 113 is added in drops to 1 ml of diethyl ether, and it is stirred for 5 more minutes. Then, 337 mg of aldehyde 3 is added to 1 ml of diethyl ether. It is allowed to reach 0° C. within 1.5 hours and hydrolyzed with ammonium chloride solution. After extraction with ethyl acetate and drying on sodium sulfate, it is concentrated by evaporation, and the residue is chromatographed on silica gel with ethyl acetate/hexane, whereby 110 mg of (5Z,7E, 22E)-(1S,3R,24S)-1,3-bis-[[dimethyl(1,1-dimethylethyl) silyl]oxy]-25-(5-methyl-2-oxazolin-2-yl)-26,27-cyclo-9,10-secocholesta-5,7,10(19),22-tetraen-24-ol 120a and 100 mg of (5Z,7E,22E)-(1S,3R,24R)-1,3-bis-[[dimethyl(1,1-dimethylethyl)-silyl]oxy]-25-(5-methyl-2-oxazolin-2-yl)-26,27-cyclo-9,10-secocholesta-5,7,10(19),22-tetraen-24-ol 120b are obtained one right after the other as colorless foams. 90 mg of disilyl ether 120a is dissolved in 12 ml of THF, 156 mg of tetrabutylammonium fluoride(trihydrate) is added, and it is stirred under nitrogen for 12 hours at room temperature. The reaction mixture is poured into water, extracted with ethyl acetate, dried on sodium sulfate and concentrated by evaporation. The residue is chromatographed on silica gel with ethyl acetate/hexane, whereby 41 mg of title compound 121a is obtained as a colorless foam.

$^1$H-NMR (300 MHz, CDCl$_3$): δ=0.56 ppm (s, 3H); 0.87 (m, 4H); 1.04 (d, 3H); 1.28 (d, 3H); 3.69 (t, 1H); 3.99 (d, 1H); 4.22 (m, 3H); 4.42 (m, 1H); 4.53 (dd, 1H); 5.00 (brs, 1H); 5.32 (brs, 1H); 5.39 (dd, 1H); 5.54 (dd, 1H); 6.01 (d, 1H); 6.38 (d, 1H)

Analogously, disilyl ether 120b is converted into title compound 121b.

$^1$H-NMR (300 MHz, CDCl$_3$): δ=0.56 ppm (s, 3H); 0.87 (m, 4H); 1.03 (d, 3H); 1.26 (d, 3H); 3.67 (t, 1H); 3.95 (d, 1H); 4.22 (m, 3H); 4.42 (m, 1H); 4.53 (dd, 1H); 5.00 (brs, 1H); 5.32 (brs, 1H); 5.45 (m, 2H); 6.01 (d, 1H); 6.38 (d, 1H)

EXAMPLE 27

(5Z,7E,22E)-[1S,3R,24S,25(R)]-25-(5-Ethyl-2-oxazolin-2-yl)-26,27-cyclo-9,10-secocholesta-5,7,10 (19),22-tetraene-1,3,24-triol 123a and (5Z,7E,22E)-[1S,3R,24R,25(R)]-25-(5-ethyl-2-oxazolin-2-yl)-26, 27-cyclo-9,10-secocholesta-5,7,10(19),22-tetraene-1, 3,24-triol 123b 2.17 ml of tert-butyllithium is introduced under nitrogen into 6 ml of diethyl ether, and it is cooled to −78° C. 436 mg of oxazoline 113 is added in drops to 1 ml of diethyl ether, and it is stirred for 5 more minutes. Then, 400 mg of aldehyde 3 is added to 1 ml of diethyl ether. It is allowed to reach 0° C. within 1.5 hours, and it is hydrolyzed with ammonium chloride solution. After extraction with ethyl acetate and drying on sodium sulfate, it is concentrated by evaporation, and the residue is chromatographed on silica gel with ethyl acetate/hexane, whereby 70 mg of (5Z,7E, 22E)-[1S,3R,24S,25(R)]-1,3-bis-[[dimethyl(1,1-dimethylethyl)silyl]oxy]-25-(5-ethyl-2-oxazolin-2-yl)-26, 27-cyclo-9,10-secocholesta-5,7,10(19),22-tetraen-24-ol 122a and 40 mg of (5Z,7E,22E)-[1S,3R,24R,25(R)]-1,3-bis-[[dimethyl(1,1-dimethylethyl)-silyl]oxy]-25-(5-ethyl-2-oxazolin-2-yl)-26,27-cyclo-9,10-secocholesta-5,7,10(19), 22-tetraen-24-ol 122b are obtained one right after the other as colorless foams.

70 mg of disilyl, ether 122a is dissolved in 10 ml of THF, 122 mg of tetrabutylammonium fluoride(trihydrate) is added, and it is stirred under nitrogen for 12 hours at room temperature. The reaction mixture is poured into water, extracted with ethyl acetate, dried on sodium sulfate and concentrated by evaporation. The residue is chromatographed on silica gel with ethyl acetate/hexane, whereby 36 mg of title compound 123a is obtained as a colorless foam.

$^1$H-NMR (300 MHz, CDCl$_3$): δ=0.57 ppm (s, 3H); 0.79 (m, 2H); 0.85 (m, 2H); 0.96 (t, 3H); 1.03 (d, 3H); 3.78 (t, 1H); 3.99 (d, 1H); 4.13 (m, 2H); 4.22 (m, 1H): 4.42 (m, 1H); 5.00 (brs, 1H); 5.32 (brs, 1H); 5.39 (dd, 1H); 5.56 (dd, 1H); 6.01 (d, 1H)6.39 (d, 1H)

Analogously, disilyl ether 122b is converted into title compound 123b.

$^1$H-NMR (300 MHz, CDCl$_3$): δ=0.56 ppm (s, 3H); 0.79 (m, 2H); 0.85 (m, 2H); 0.94 (t, 3H); 1.02 (d, 3H); 3.78 (t, 1H); 3.93 (d, 1H); 4.13 (m, 2H); 4.22 (m, 1H); 4.42 (m, 1H); 5.00 (brs, 1H); 5.32 (brs, 1H); 5.45 (m, 2H); 6.01 (d, 1H); 6.39 (d, 1H)

20-Methyl-Series

EXAMPLE 28

(5Z,7E,22E)-(1S,3R,24S)-20-Methyl-25-(4-methylthiazol-2-yl)-26,27-cyclo-9,10-secocholesta-5,7,10(19),22-tetraene-1,3,24-triol 126a and (5Z,7E, 22E)-(1S,3R,24R)-20-methyl-25-(4-methylthiazol-2-yl)-26,27-cyclo-9,10-secocholesta-5,7,10(19),22-tetraene-1,3,24-triol 126b 640 mg of (5E,7E,22E)-(1S,3R)-1,3-bis[[dimethyl(1,1-dimethylethyl)silyl]oxy]-20-methyl-9,10-secochola-5,7,10

(19),22-tetraen-24-al 124 (WO 94/07853) is treated analogously to aldehyde 29, and 620 mg of (5Z,7E,22E)-(1S,3R)-1,3-bis[[dimethyl(1,1-dimethylethyl)silyl]oxy]-20-methyl-9,10-secochola-5,7,10(19),22-tetraen-24-al 125 is obtained as a colorless foam.

$^1$H-NMR (300 MHz, CDCl$_3$): δ=0.05 ppm (s, 12H); 0.52 (s, 3H); 0.87 (s, 3H); 1.10 (s, 3H); 1.17 (s, 3H); 4.18 (m, 1H); 4.38 (m, 1H); 4.82 (brs, 1H); 5.18 (brs, 1H); 5.99 (d, 1H); 6.02 (dd, 1H); 6.20 (d, 1H); 7.00 (d, 1H); 9.52 (d, 1H)

Analogously to Example 5, aldehyde 125 is converted with 2-(1-bromocyclopropyl)-4-methylthiazole 18 into title compounds 126a and 126b which after chromatographic separation accumulate as colorless foams.

126a: $^1$H-NMR (300 MHz, CDCl$_3$): δ=0.50 ppm (s, 3H); 0.97 (s, 3H); 1.04 (s, 3H); 2.39 (s, 1H); 3.98 (d, 1H); 4.22 (m, 1H); 4.43 (m, 1H); 5.00 (brs, 1H); 5.32 (dd, 1H); 5.33 (brs, 1H); 5.86 (d, 1H); 5.98 (d, 1H); 6.48 (d, 1H); 6.64 (s, 1H)

126b: $^1$H-NMR (300 MHz, CDCl$_3$): δ=0.49 ppm (s, 3H); 0.96 (s, 3H); 1.05 (s, 3H); 2.39 (s, 1H); 3.98 (d, 1H); 4.22 (m, 1H); 4.43 (m, 1H); 5.00 (brs, 1H); 5.31 (dd, 1H); 5.33 (brs, 1H); 5.86 (d, 1H); 5.98 (d, 1H); 6.48 (d, 1H); 6.64 (s, 1H)

20-Epi Series

EXAMPLE 29

(5Z,7E,22E)-(1S,3R,20S,24S)-25-(5-Butyloxazol-2-yl)-26,27-cyclo-9,10-secocholesta-5,7,10(19),22-tetraene-1,3,24-triol 131a and (5Z,7E,22E)-(1S,3R,20S,24R)-25-(5-butyloxazol-2-yl)-26,27-cyclo-9,10-secocholesta-5,7,10(19),22-tetraene-1,3,24-triol 131b 2.1 g of (5E,7E)-(1S,3R,20R)-1,3-bis[[dimethyl(1,1-dimethylethyl)silyl]oxy]-9,10-secopregna-5,7,10(19)-triene-20-carbaldehyde 127 [M. J. Calverley, L. Binderup Bioorg. Med. Chem. Lett. 3, 1845 (1993)] is treated analogously to aldehyde 29, and 2.0 g of (5Z,7E)-(1S,3R,20R)-1,3-bis[[dimethyl(1,1-dimethylethyl)silyl]oxy]-9,10-secopregna-5,7,10(19)-triene-20carbaldehyde 128 is obtained as a colorless foam.

$^1$H-NMR (300 MHz, CDCl$_3$): δ=0.05 ppm (s, 12H); 0.56 (s, 3H); 0.87 (s, 3H); 1.17 (d, 3H); 4.18 (m, 1H); 4.38 (m, 1H); 4.83 (brs, 1H); 5.18 (brs, 1H); 6.00 (d, 1H); 6.22 (d, 1H); 9.54 (d, 1H)

1.9 g of aldehyde-128 is introduced into 28 ml of toluene, 2.6 g of N-methoxy-N-methyl-2-(triphenylphosphoranylidene)-acetamide is added under nitrogen [D. A. Evans et al. J. Am. Chem. Soc. 112, 7001 (1990)] and heated for 3 days to 80° C. After cooling, it is poured into water, extracted with ethyl acetate, dried on sodium sulfate and concentrated by evaporation. The residue is chromatographed on silica gel with ethyl acetate/hexane, whereby 1.6 g of (5Z,7E,22E)-(1S,3R,20R)-1,3-bis[[dimethyl(1,1-dimethylethyl)silyl]oxy]-N-methyl-N-methoxy-9,10-secochola-5,7,10(19),22-tetraen-24-amide 129 accumulates as a colorless foam.

1.4 g of amide 129 is dissolved in 25 ml of THF and cooled to −78° C. under nitrogen. 10 ml of diisobutylaluminium solution (1 M in hexane) is added in drops, and it is stirred for 1 more hour. 0.8 ml of methanol is now added in drops, and the mixture is allowed to reach room temperature. The reaction mixture is now poured into potassium-sodium tartrate solution, extracted with ethyl acetate, and the organic phase is dried on sodium sulfate and concentrated by evaporation. The residue is chromatographed on silica gel with ethyl acetate/hexane, whereby 1.1 g of (5Z,7E,22E)-(1S,3R,20R)-1,3-bis[[dimethyl(1,1-dimethylethyl)silyl]oxy]-9,10-secochola-5,7,10(19),22-tetraen-24-al 130 is obtained as a colorless foam.

$^1$H-NMR (300 MHz, CDCl$_3$): δ=0.05 ppm (s, 12H); 0.53 (s, 3H); 0.87 (s, 3H); 1.10 (d, 3H); 4.20 (m, 1H); 4.39 (m, 1H); 4.85 (brs, 1H); 5.20 (brs, 1H); 6.00 (d, 1H); 6.10 (dd, 1H); 6.22 (d, 1H); 6.79 (dd, 1H); 9.53 (d, 1H)

Analogously to Example 16, aldehyde 130 is converted with 2-(1-bromocyclopropyl)-5-butyloxazole 87 into title compounds 131a and 131b which after chromatographic separation accumulate as colorless foams.

131a: $^1$H-NMR (300 MHz, CDCl$_3$): δ=0.56 ppm (s, 3H); 0.90 (t, 3H); 0.96 (m, 2H); 1.11 (d, 3H); 1.15 (m, 2H); 2.57 (s, 3H); 4.10 (d, 1H); 4.22 (m, 1H); 4.43 (m, 1H); 5.00 (brs, 1H); 5.33 (brs, 1H); 5.41 (dd, 1H); 5.58 (dd, 1H); 6.00 (d, 1H); 6.37 (d, 1H); 6.57 (s, 1H)

131a: $^1$H-NMR (300 MHz, CDCl$_3$): δ=0.57 ppm (s, 3H); 0.90 (t, 3H); 0.97 (m, 2H); 1.10 (d, 3H); 1.15 (m, 2H); 2.58 (s, 3H); 4.10 (d, 1H); 4.22 (m, 1H); 4.43 (m, 1H); 5.00 (brs, 1H); 5.33 (brs, 1H); 5.42 (dd, 1H); 5.53 (dd, 1H); 6.00 (d, 1H); 6.38 (d, 1H); 6.58 (s, 1H)

Starting Materials in the 5-Alkyloxazole Series

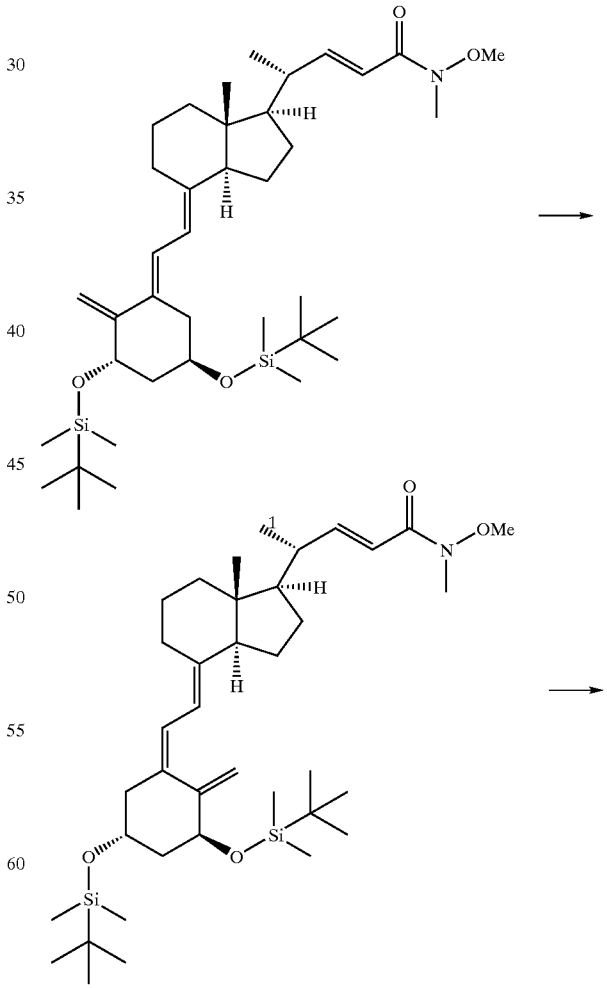

2

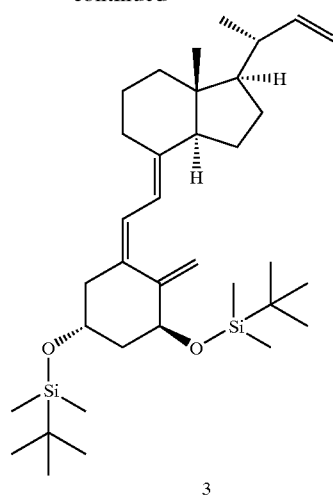
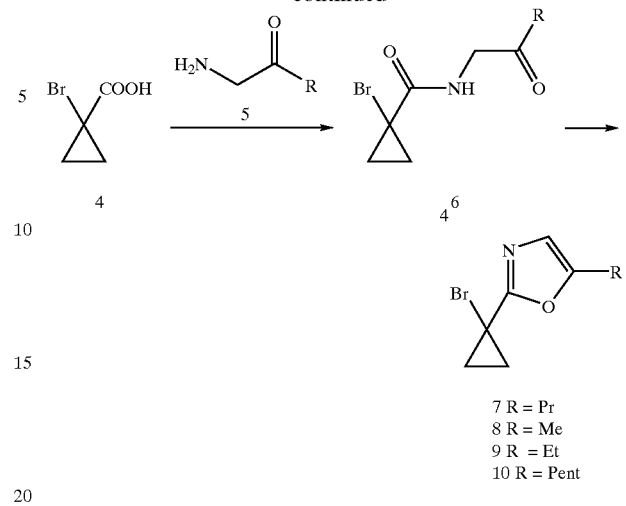
5-Alkyloxazole Derivatives
7 R = Pr
8 R = Me
9 R = Et
10 R = Pent
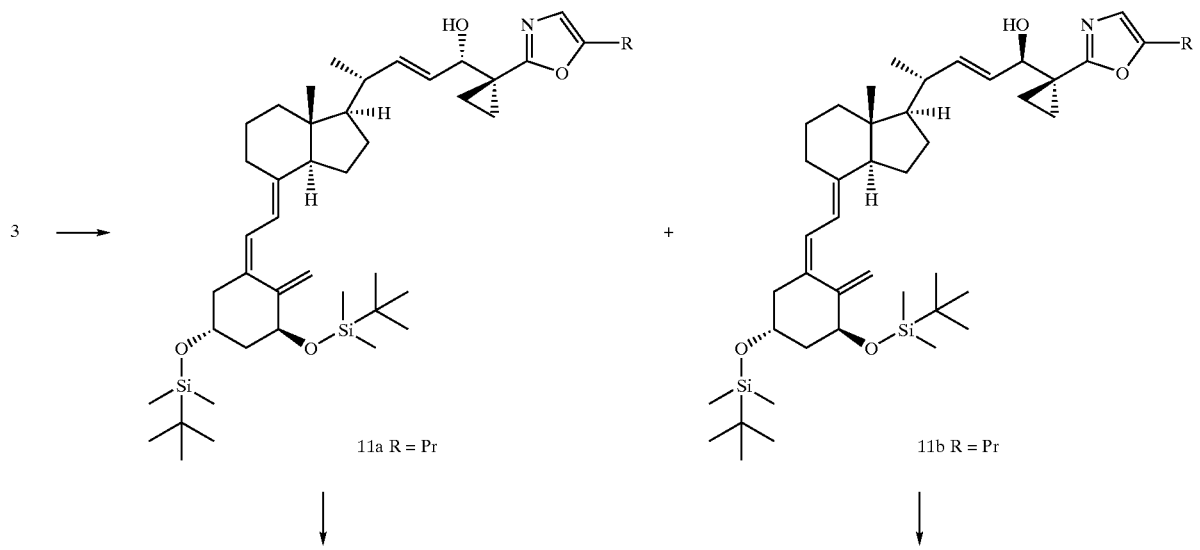
11a R = Pr
11b R = Pr
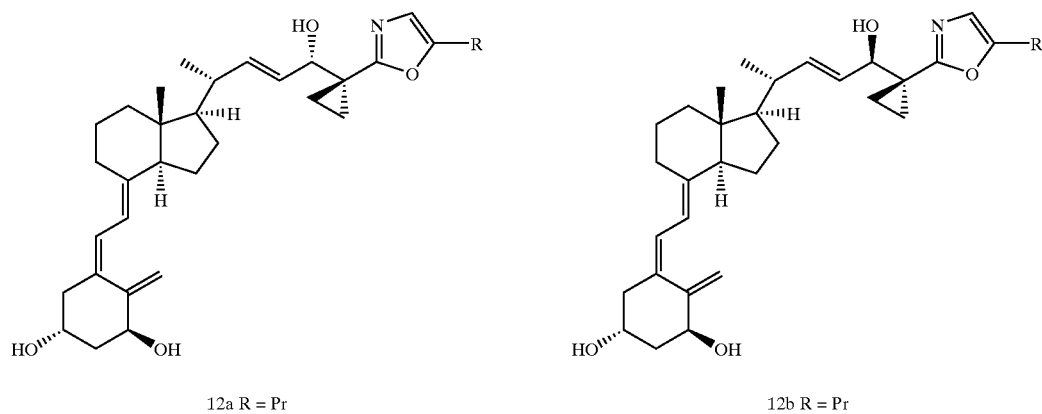
12a R = Pr
12b R = Pr 3 ⟶
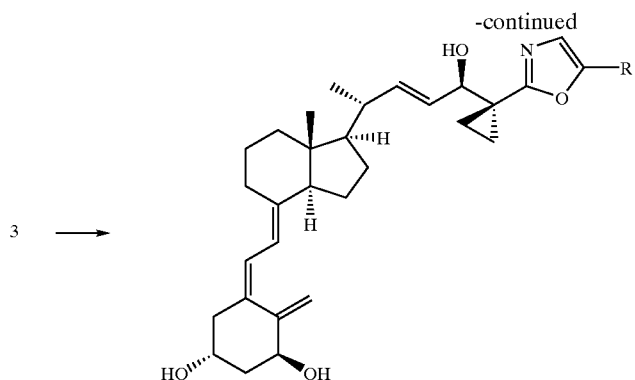
13b R = Me
14b R = Et
15b R = Pent
Starting Materials in the 4-Alkylthiazale Series
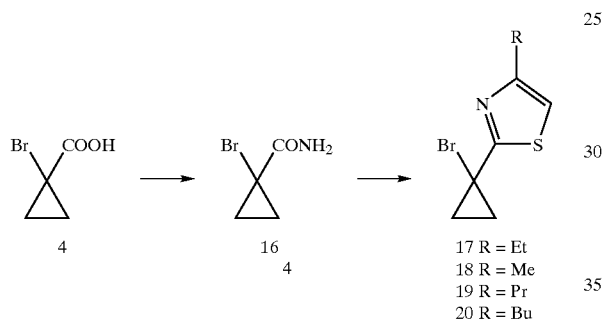
17 R = Et
18 R = Me
19 R = Pr
20 R = Bu
4-Alkylthiazole Derivatives
3 ⟶
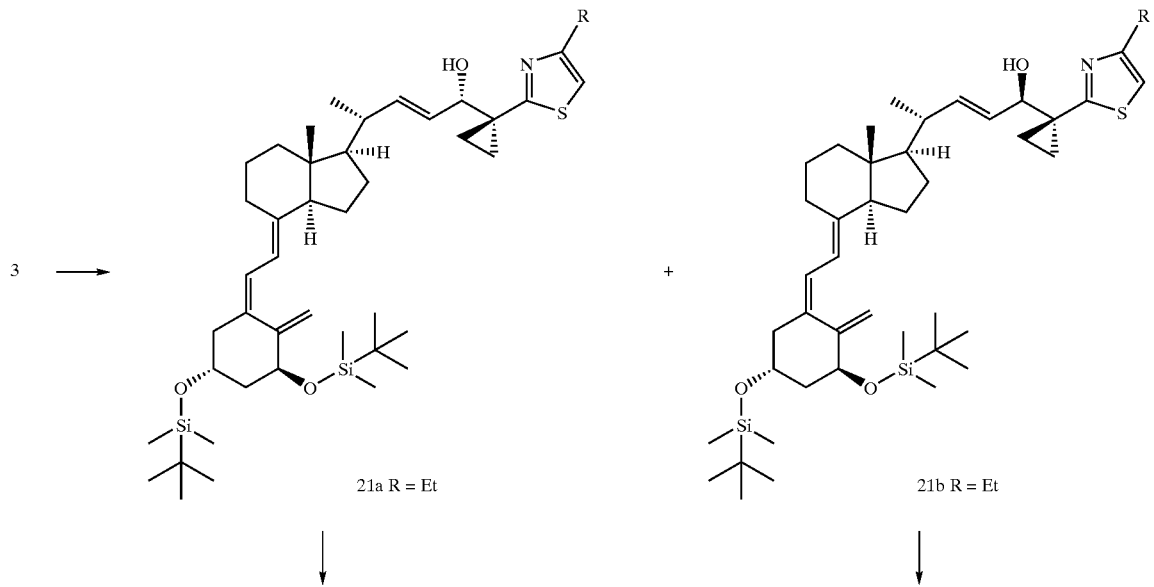
21a R = Et                    21b R = Et
↓                              ↓

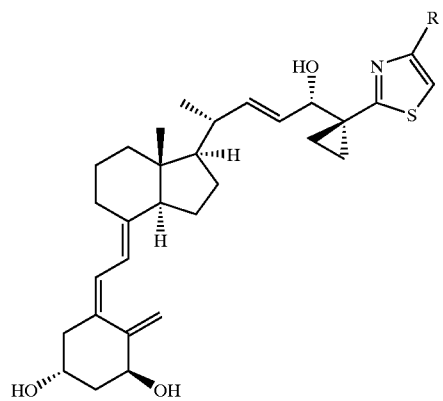
22a R = Et
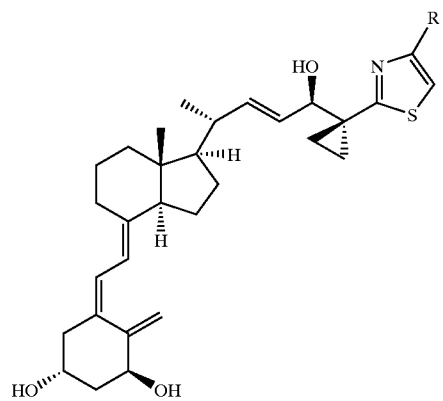
22b R = Et
3 →
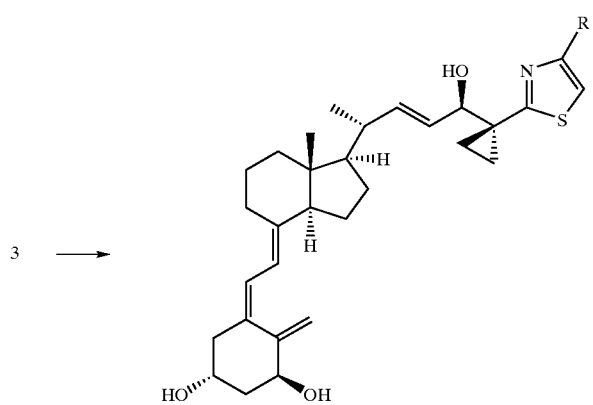
23b R = Me
24b R = Pr
25b R = Bu
Starting Materials in the Phenyl Series
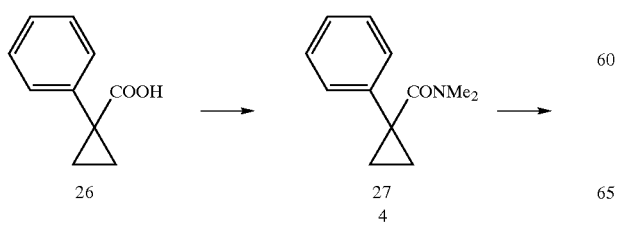
26   27
-continued
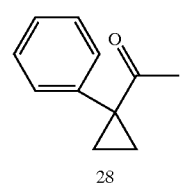
28

Phenyl Derivatives
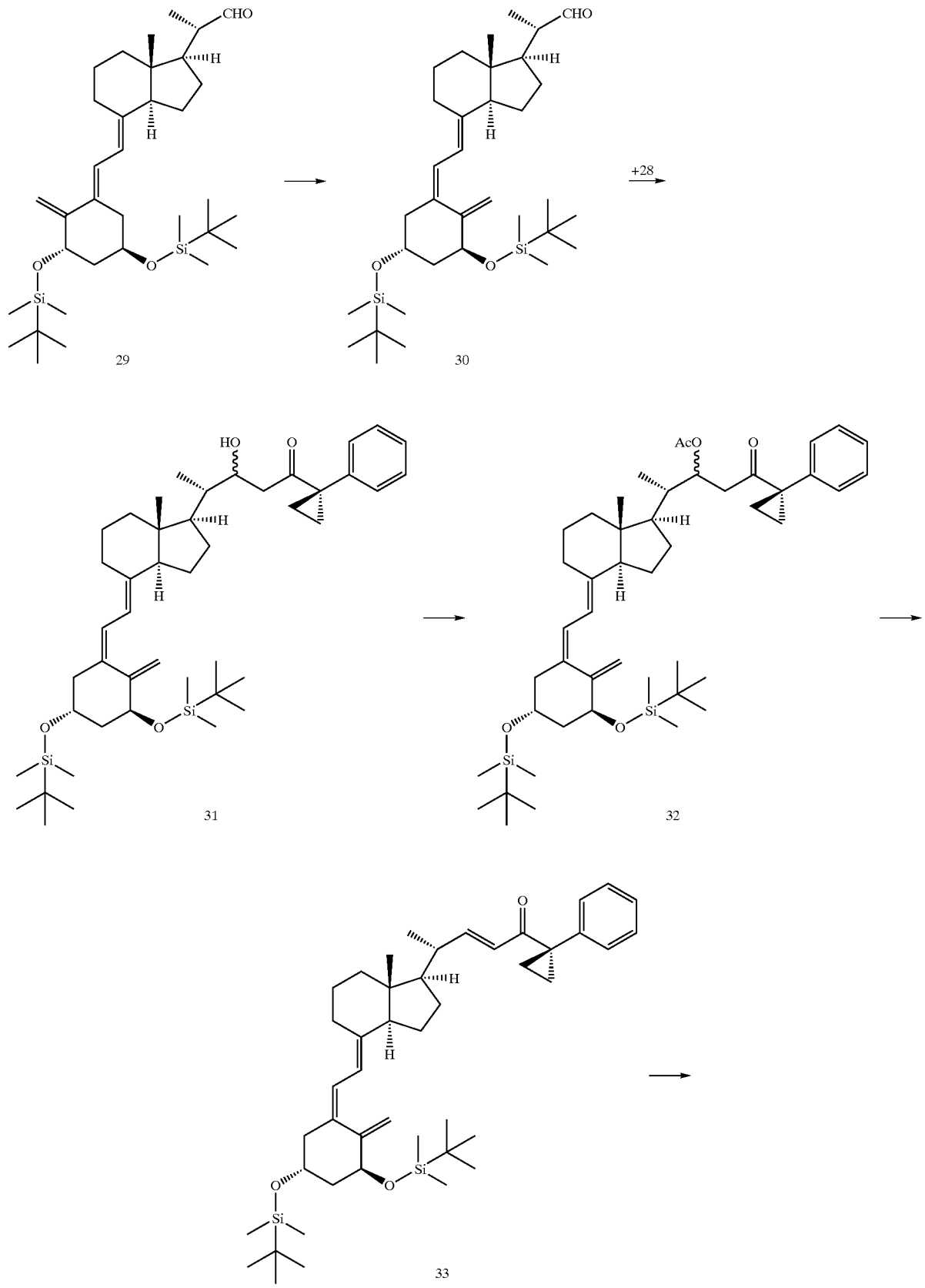

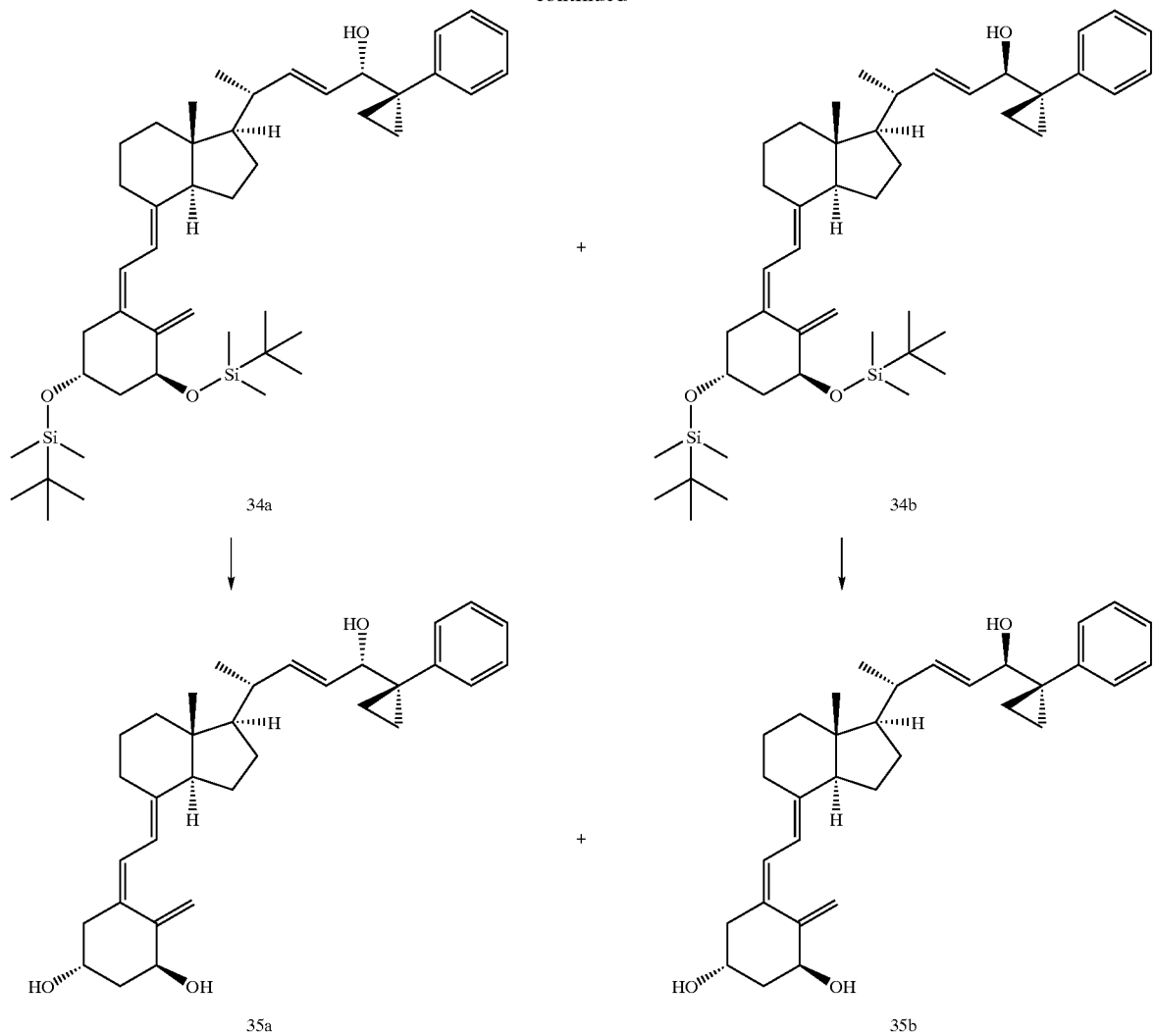
34a → 35a
+
34b → 35b
Starting Materials in the 4-Alkylphenyl Series
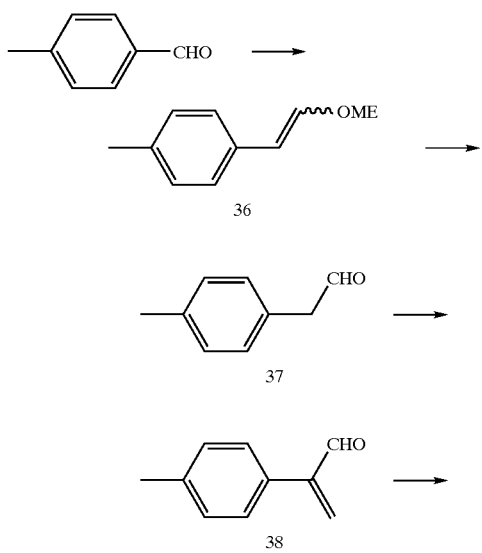
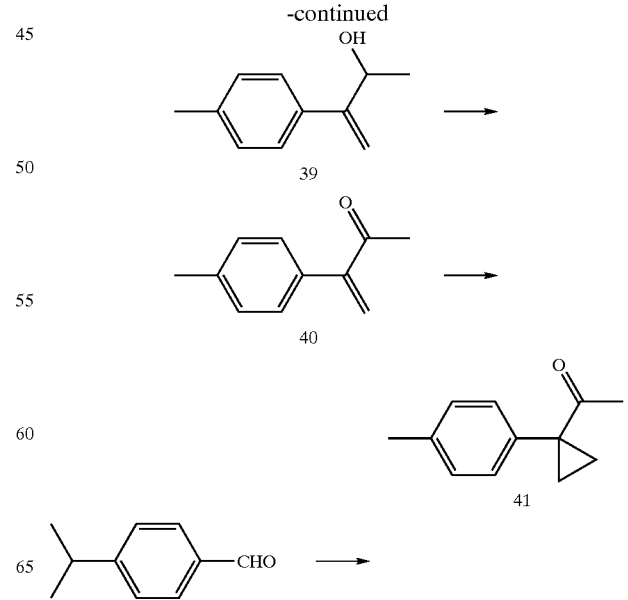

75
-continued
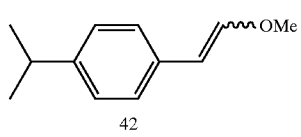
42
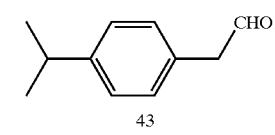
43
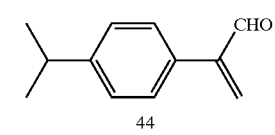
44
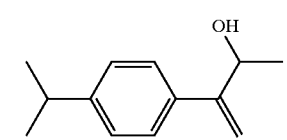
45
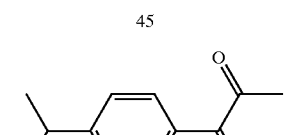
46
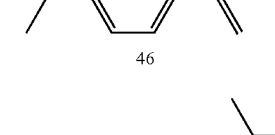
47
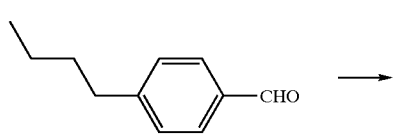
76
-continued
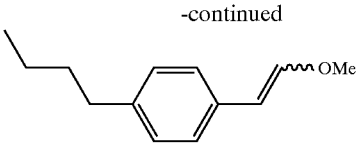
48
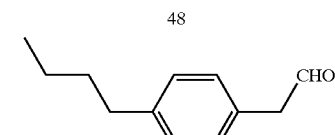
49
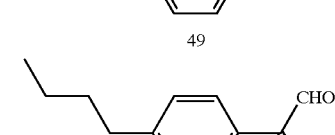
50
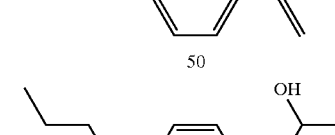
51
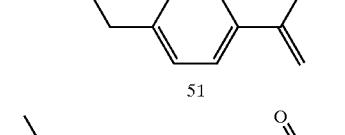
52
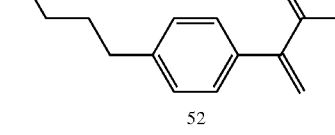
53
4-Alkylphenyl Derivatives
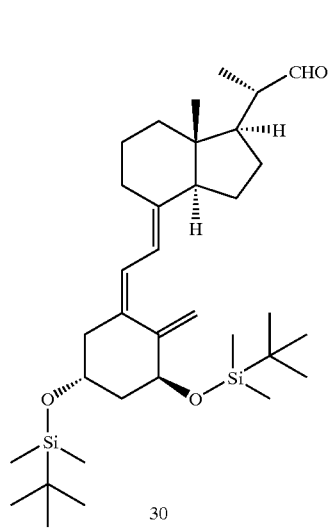
30
+41, 47, 53 →
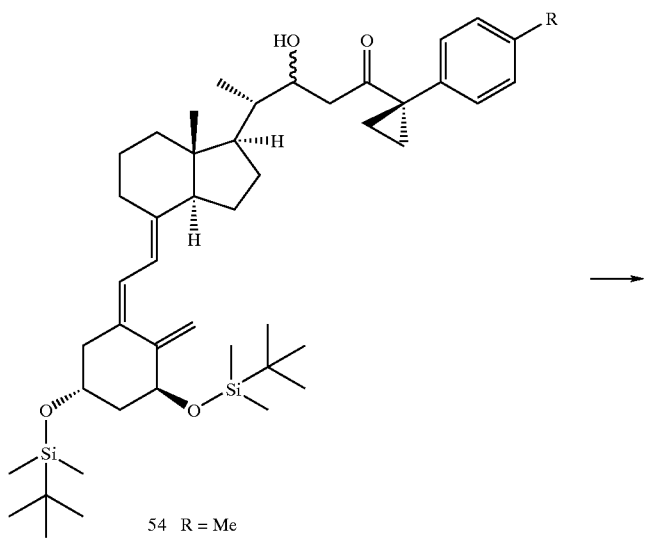
54  R = Me
61  R = iPr
68  R = Bu

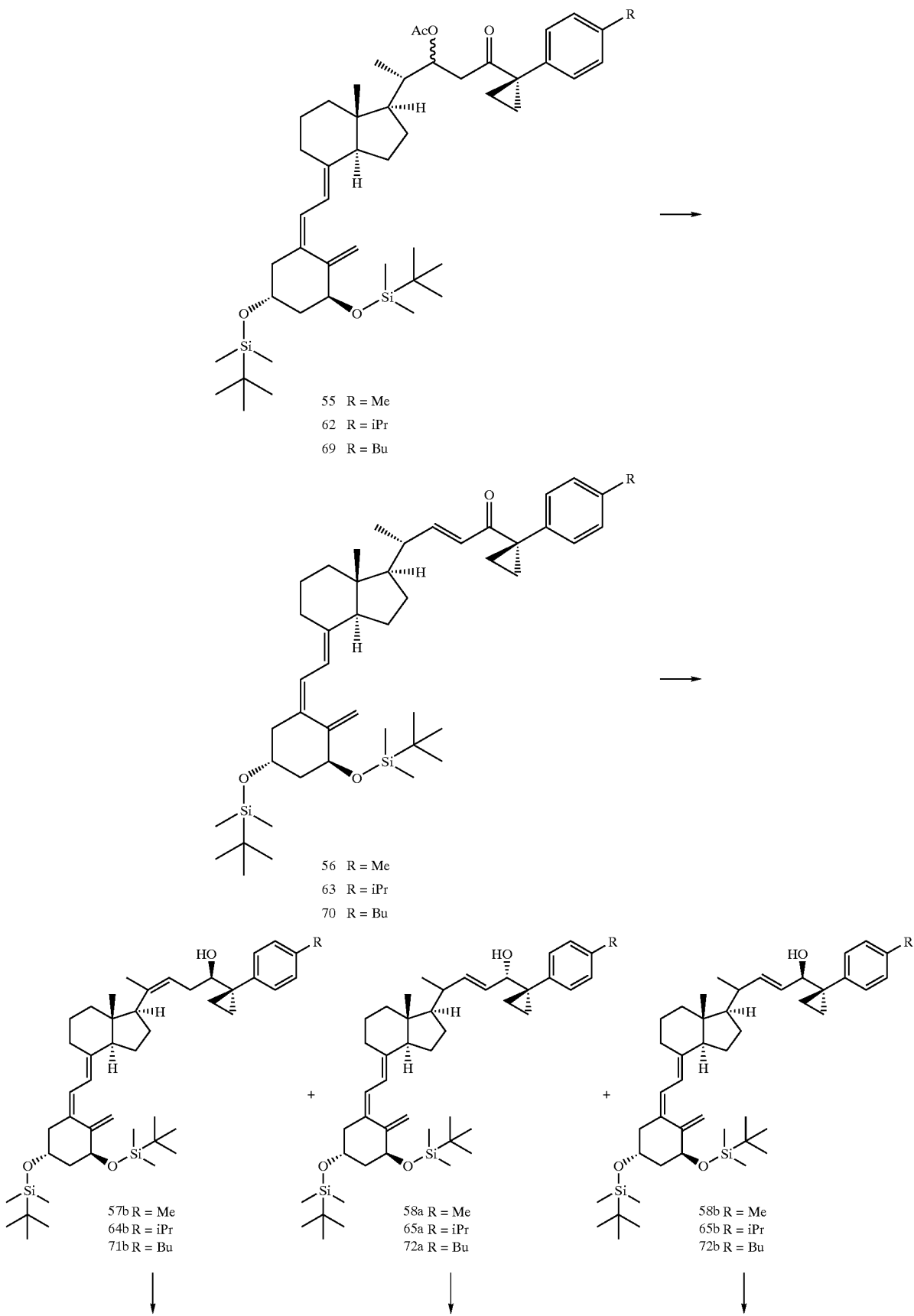
-continued
55 R = Me
62 R = iPr
69 R = Bu
56 R = Me
63 R = iPr
70 R = Bu
57b R = Me
64b R = iPr
71b R = Bu
58a R = Me
65a R = iPr
72a R = Bu
58b R = Me
65b R = iPr
72b R = Bu

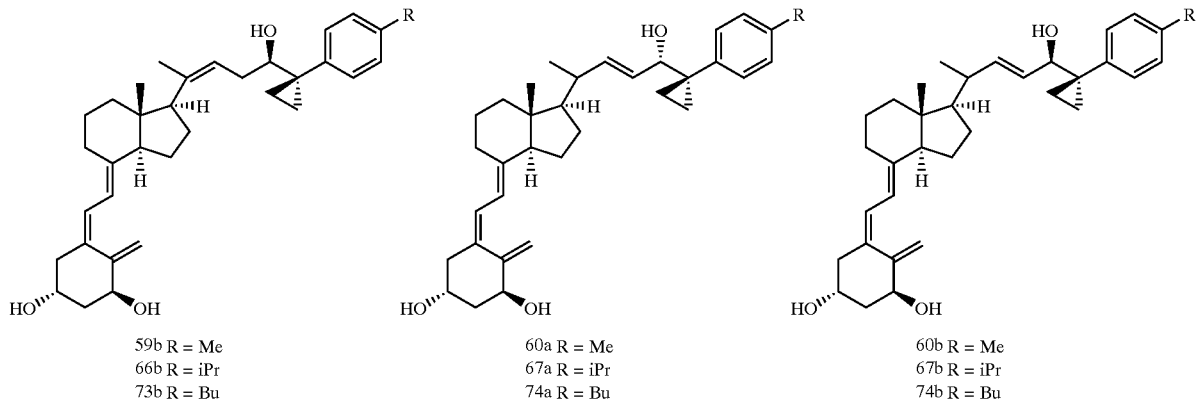
| 59b R = Me | 60a R = Me | 60b R = Me |
| 66 R = iPr | 67a R = iPr | 67b R = iPr |
| 73b R = Bu | 74a R = Bu | 74b R = Bu |
Starting Materials in the 4-Alkyloxazole Series
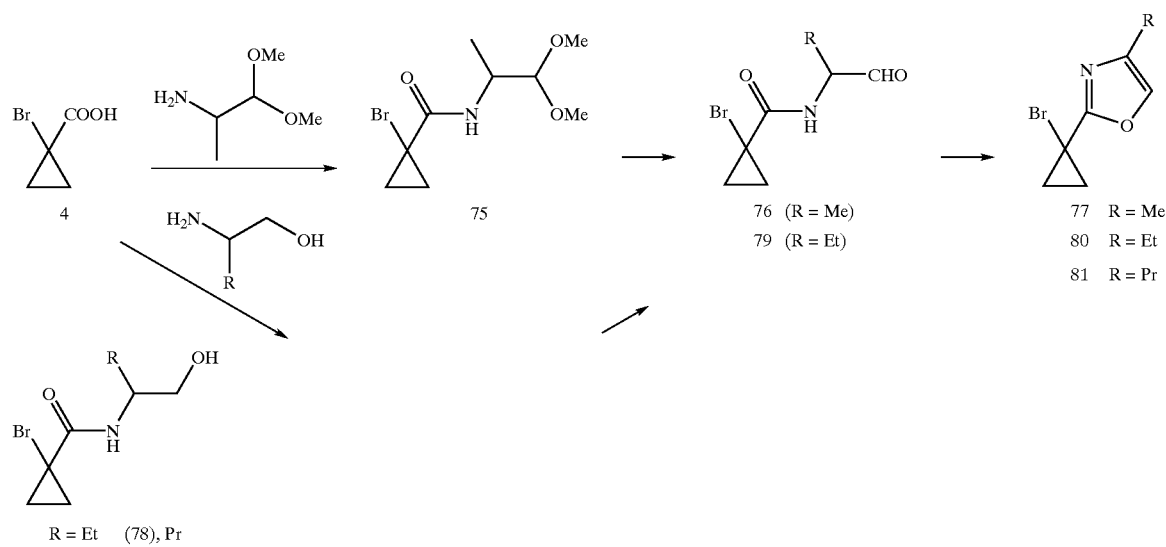
| 76 (R = Me) | 77 R = Me |
| 79 (R = Et) | 80 R = Et |
| | 81 R = Pr |
R = Et (78), Pr
4-Alkyloxazole Series
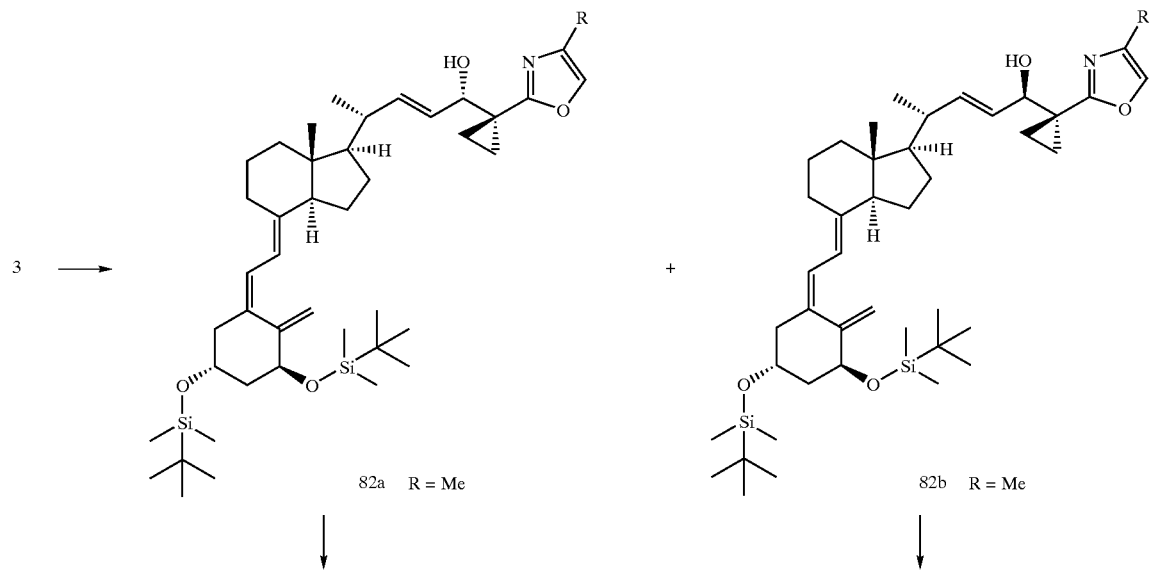
82a R = Me 　　　　　82b R = Me 81 82
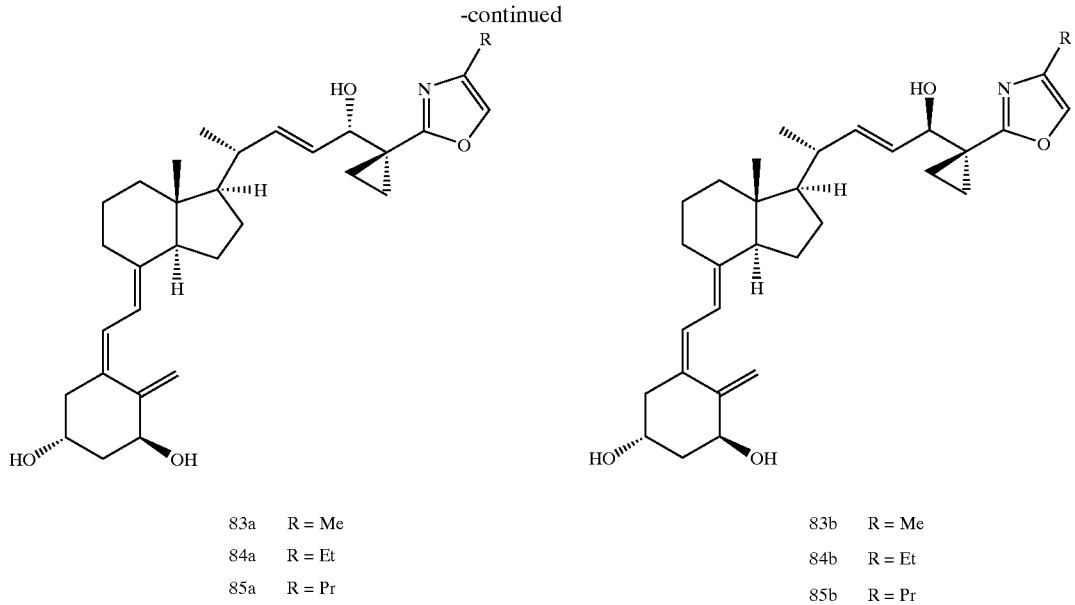
| 83a | R = Me | 83b | R = Me |
| 84a | R = Et | 84b | R = Et |
| 85a | R = Pr | 85b | R = Pr |
5-Butyloxazole Derivative
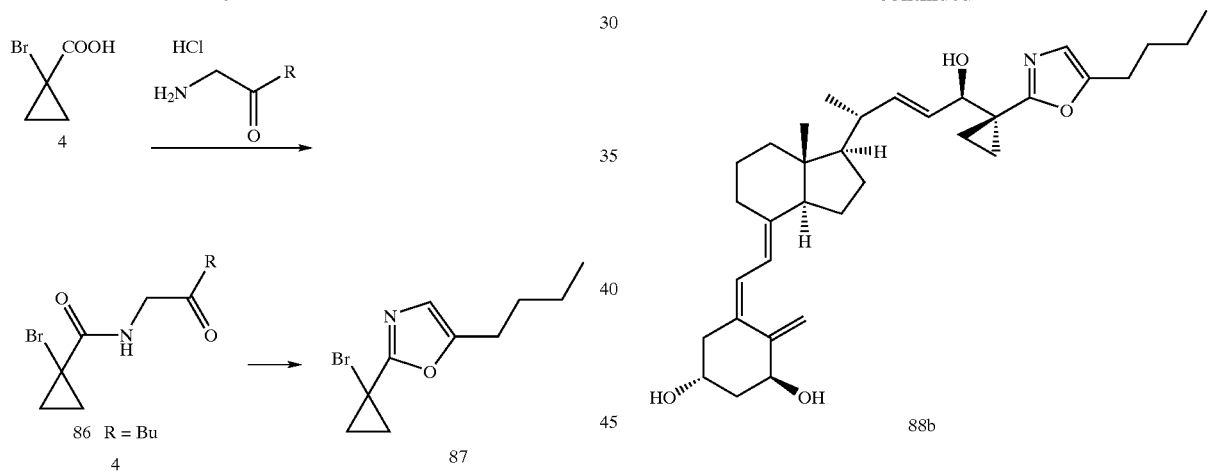
Starting Material for the 5-Alkylthiazole Series
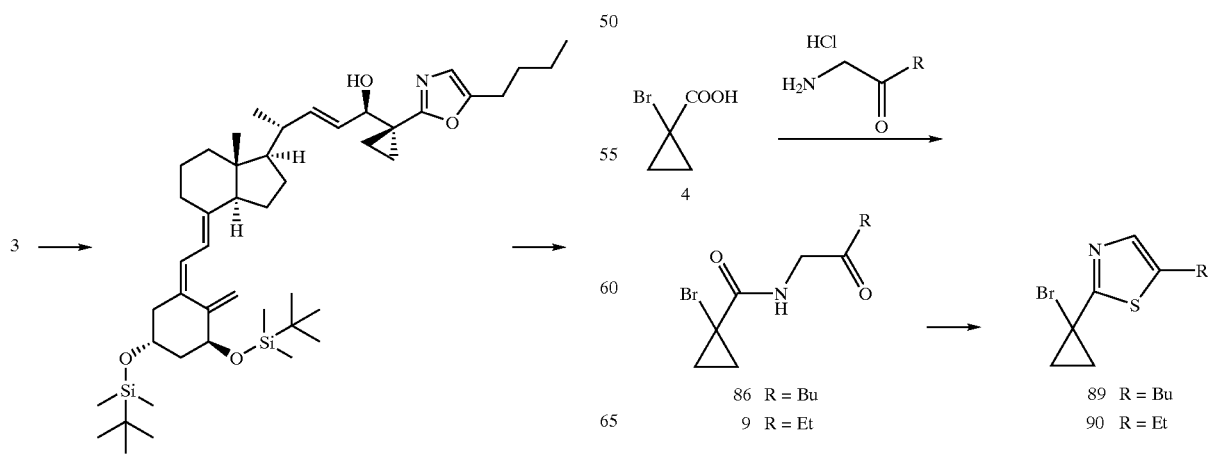
86 R = Bu
9 R = Et
89 R = Bu
90 R = Et

83
5-Alkylthiazole Series
84
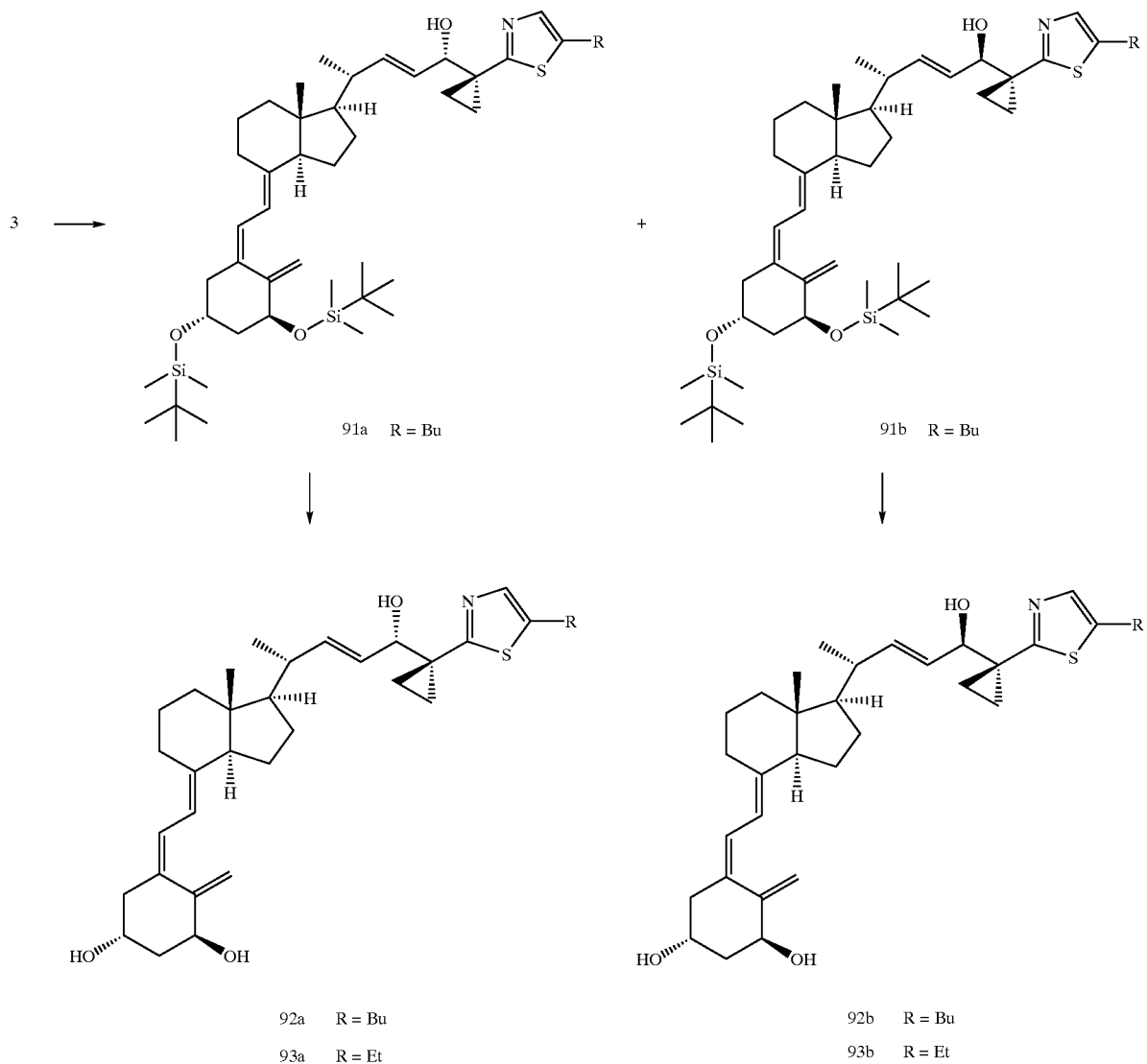
91a  R = Bu
91b  R = Bu
92a  R = Bu
93a  R = Et
92b  R = Bu
93b  R = Et
1,2,4-Oxadiazole Series
-continued
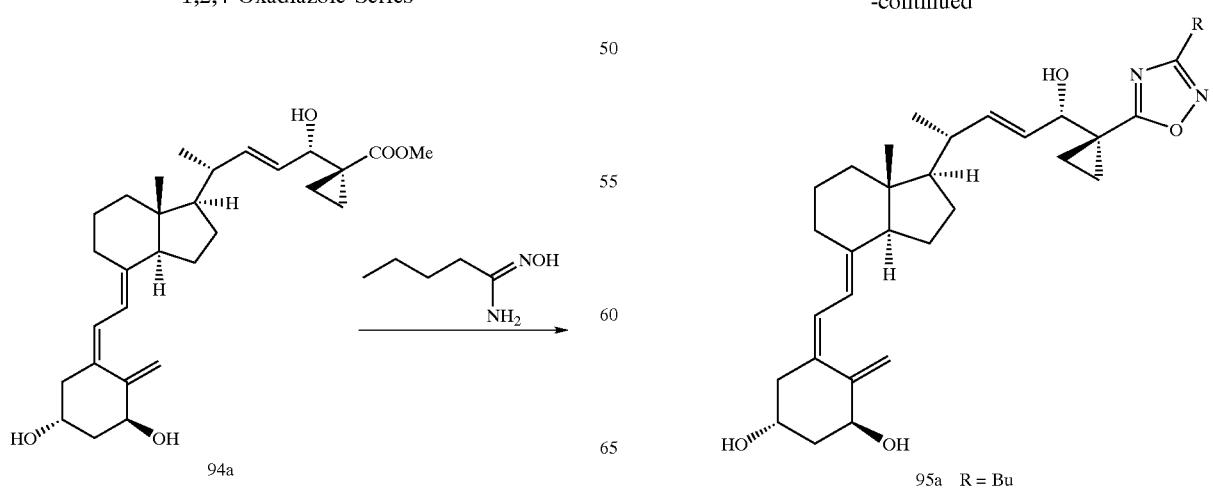
94a
95a  R = Bu 85
-continued
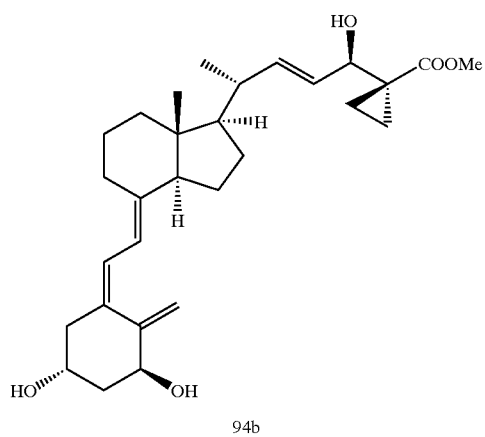
94b
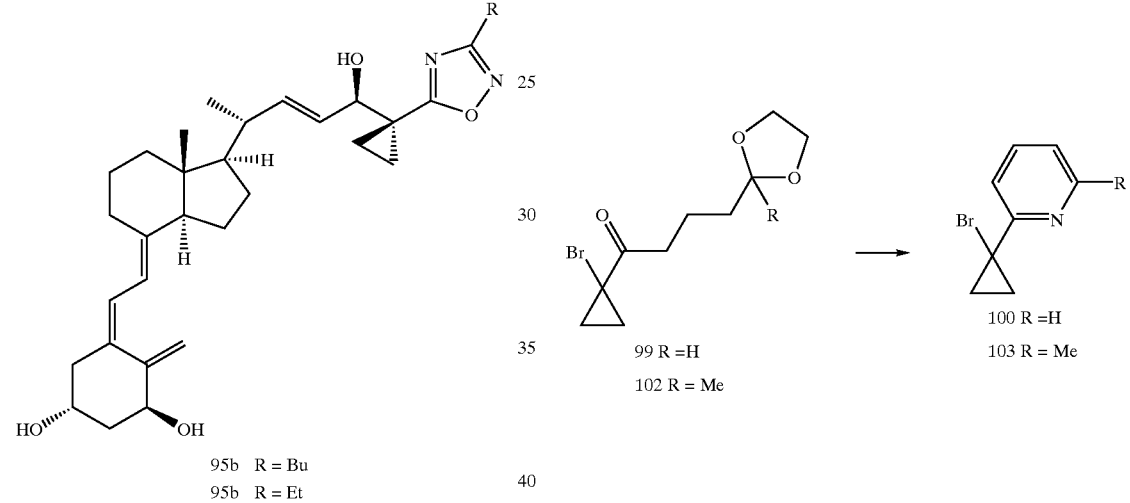
95b R = Bu
95b R = Et
86
Starting Materials for the 25-Pyridyl Series
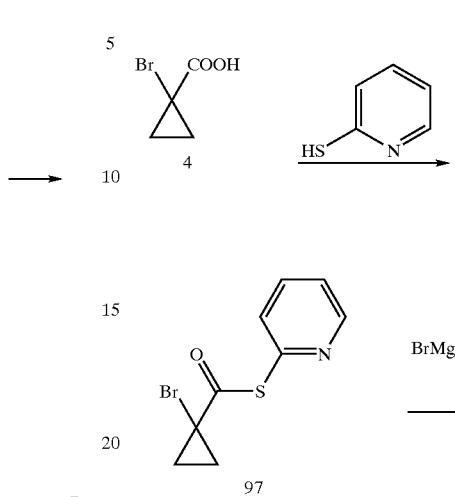
25-Pyridyl Series
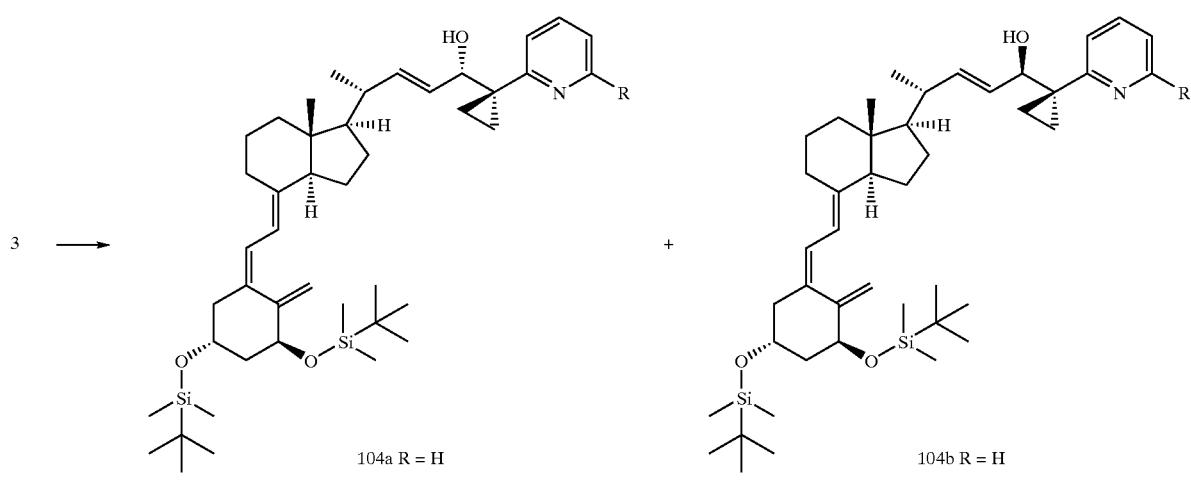
104a R = H          104b R = H

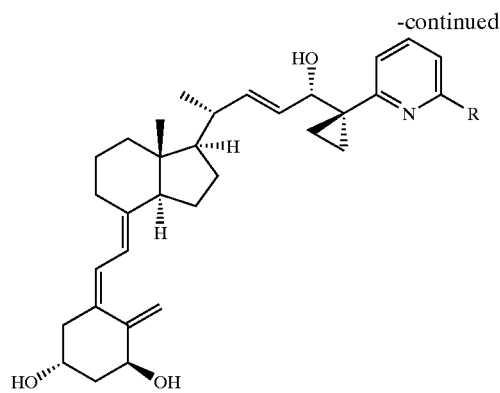
105a R = H
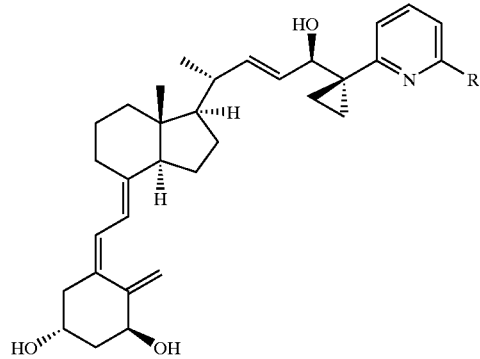
105b R = H
106b R = Me
Starting Materials in the 25-Oxazoline Series
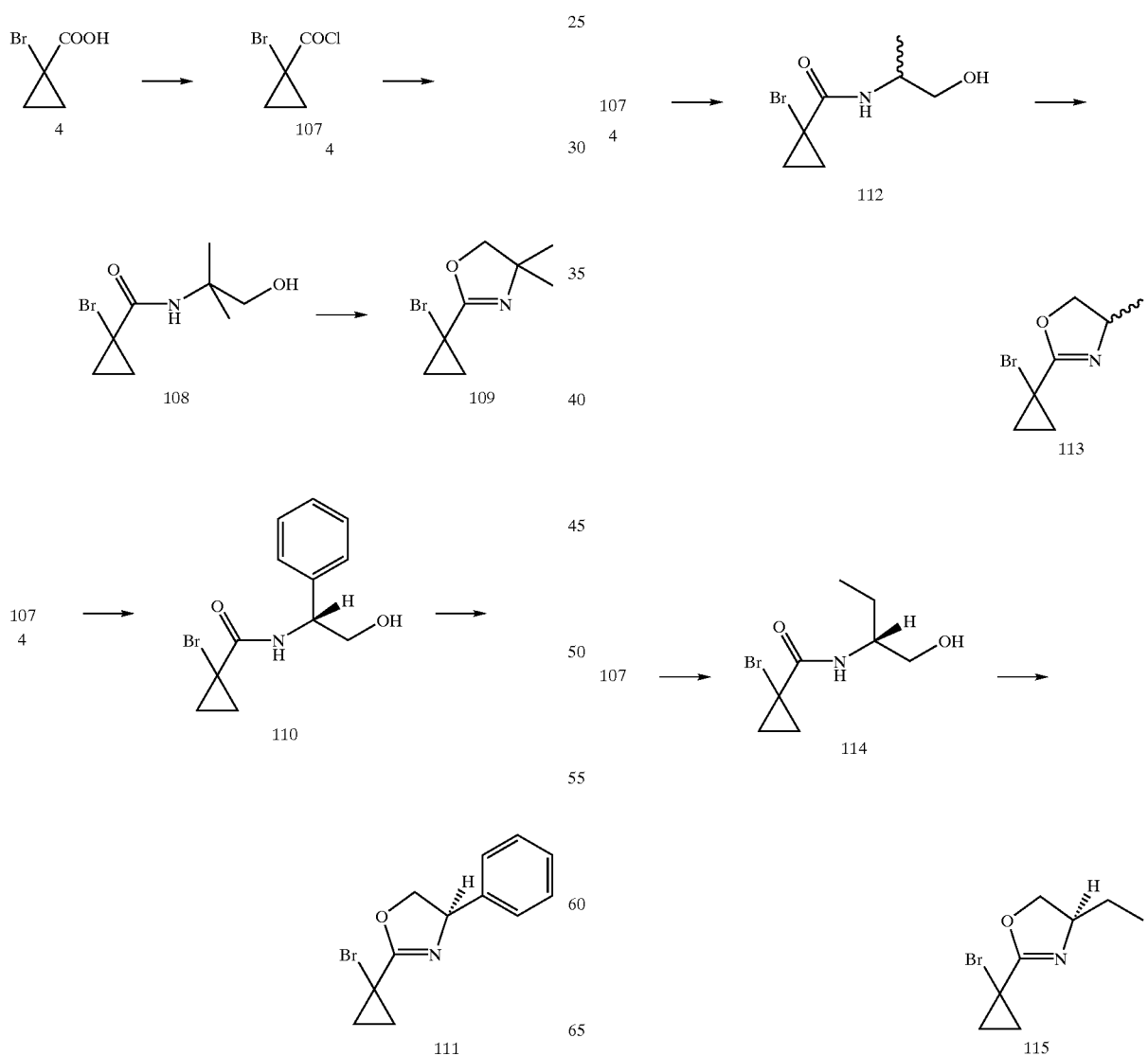

89 90
25-Oxazoline Series
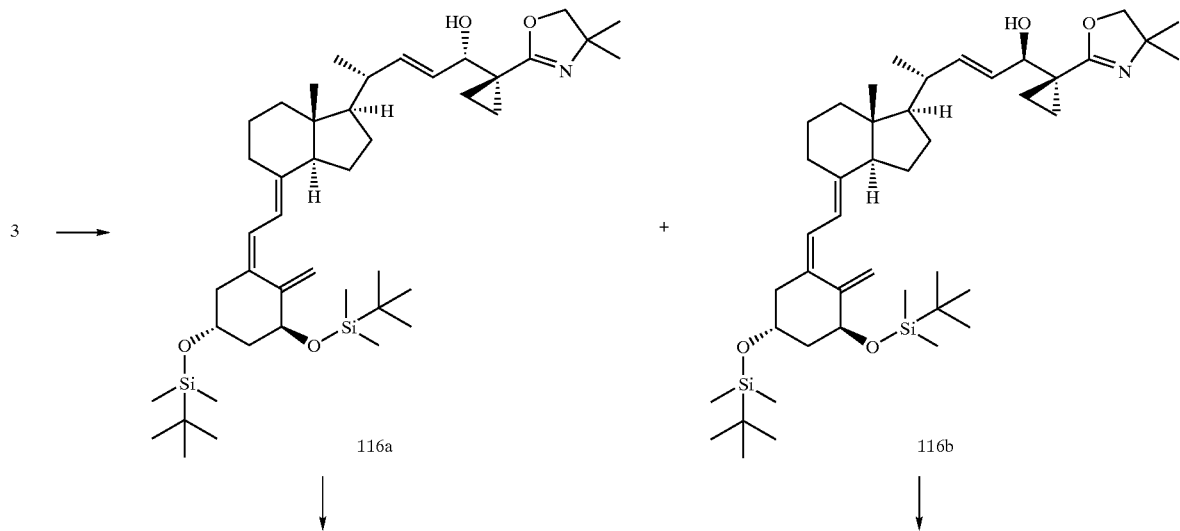
3 → 116a    +    116b
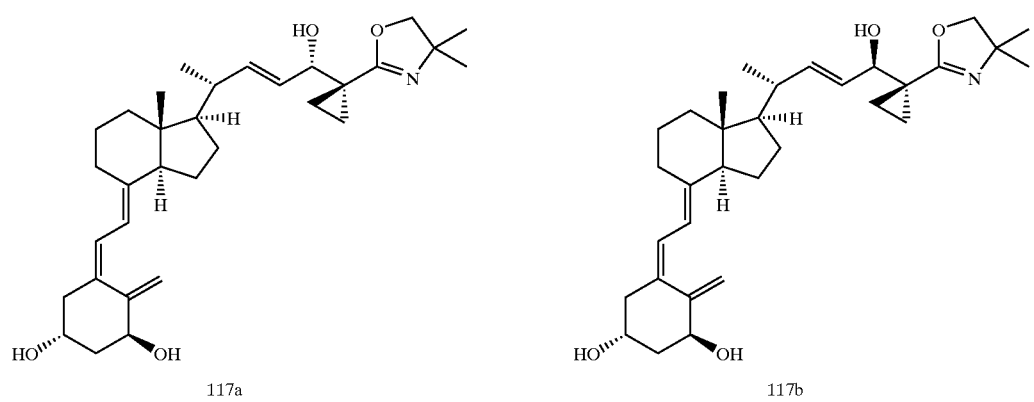
117a    117b
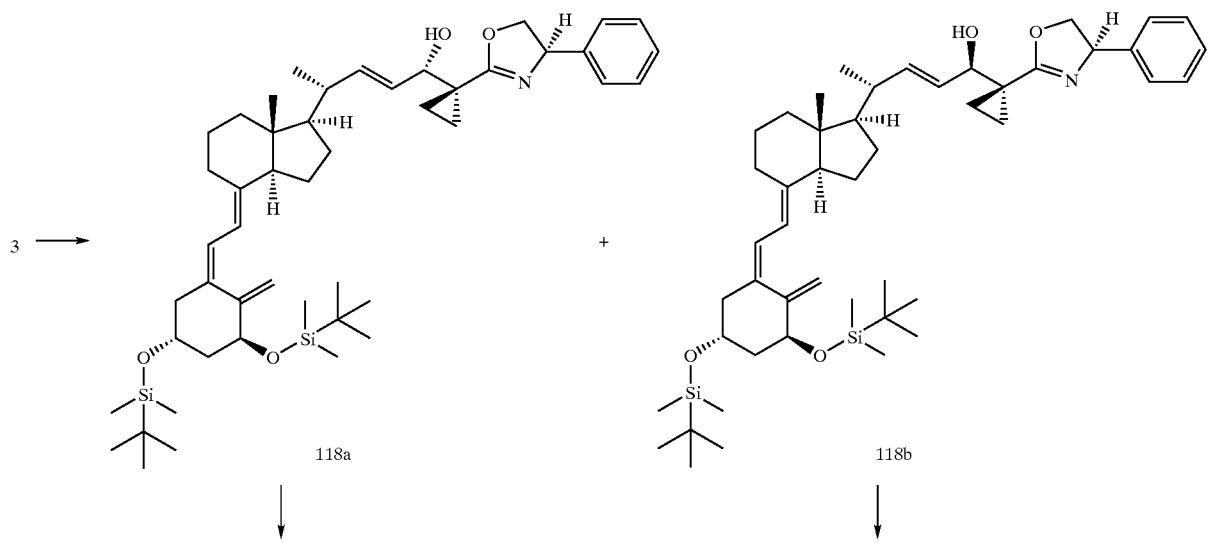
3 →    118a    +    118b

91
92
-continued
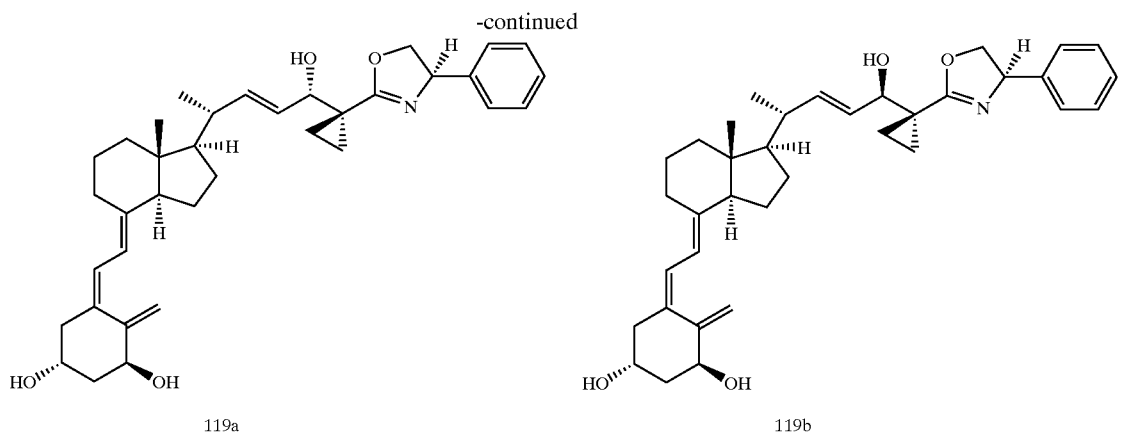
119a
119b
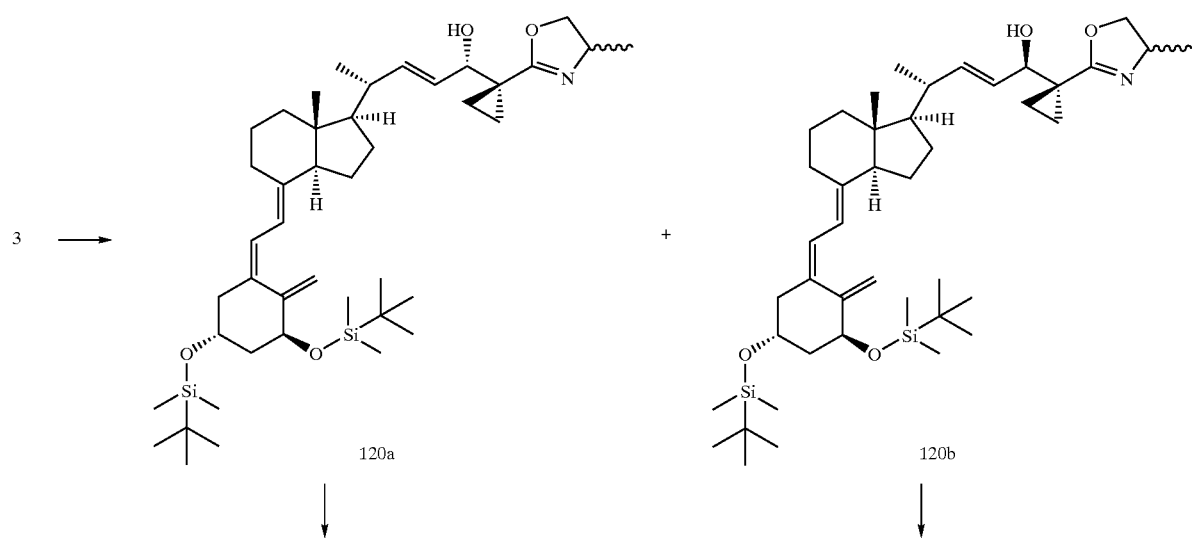
120a
120b
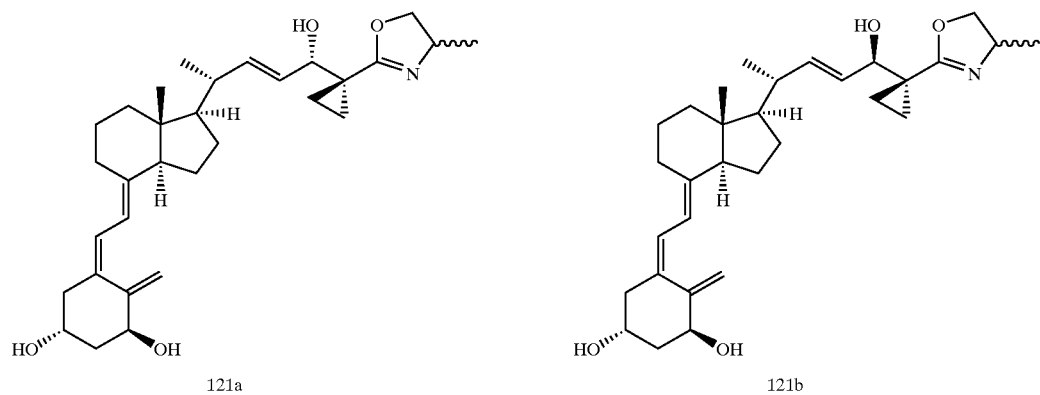
121a
121b

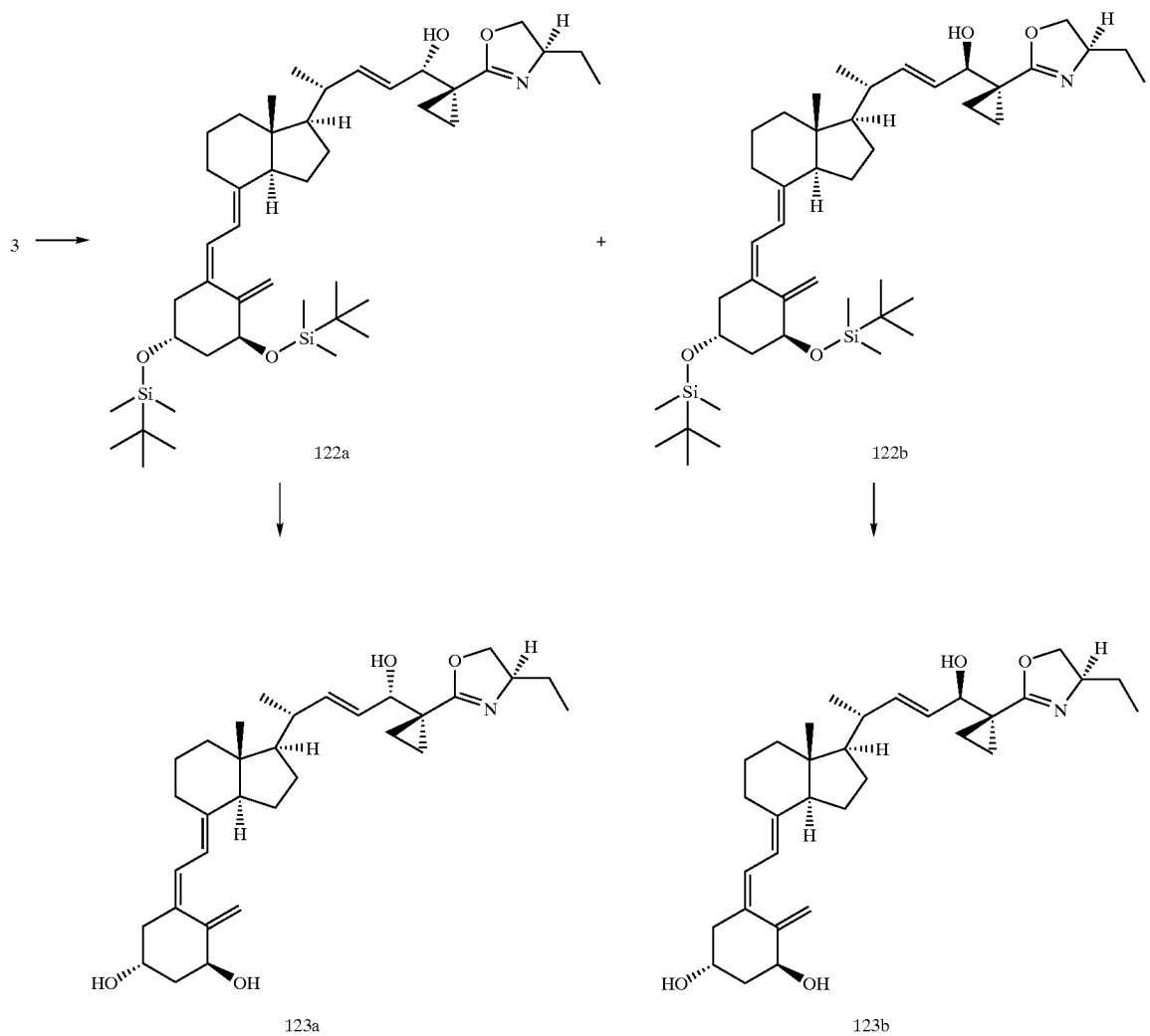
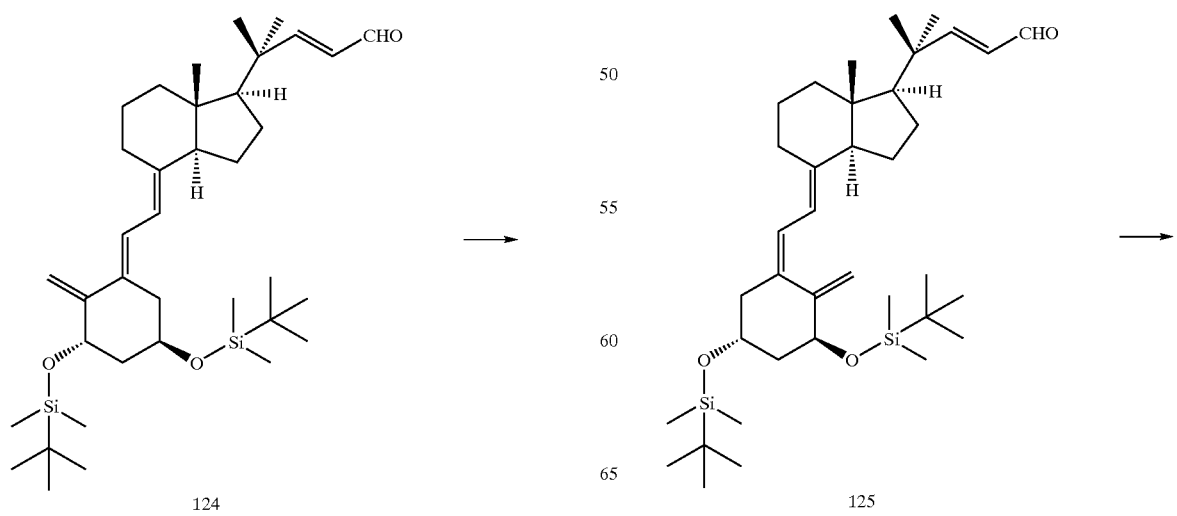
20-Methyl Series

95
-continued
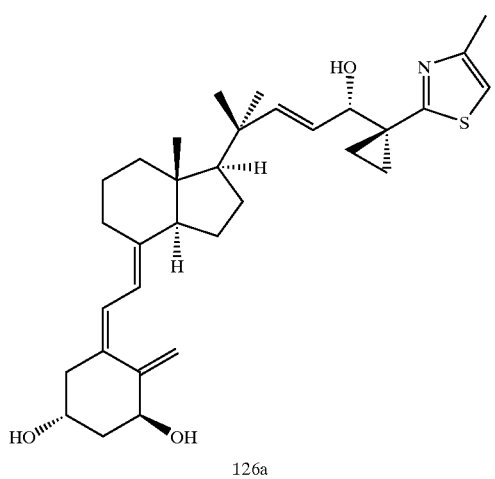
126a
+
96
-continued
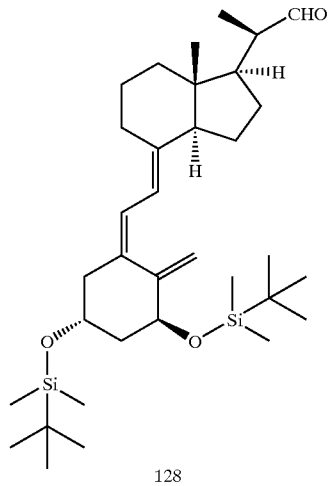 
128
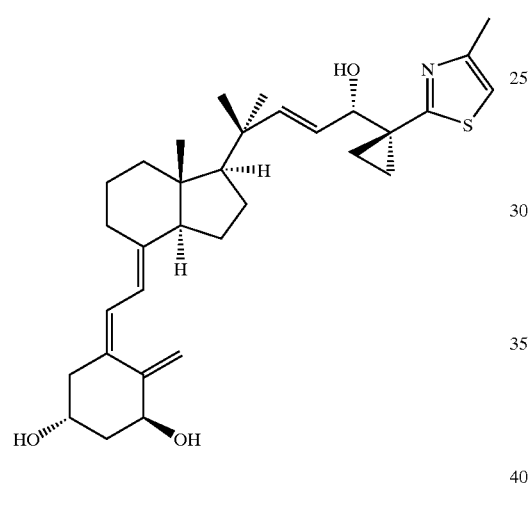
126b
20-Epi Series
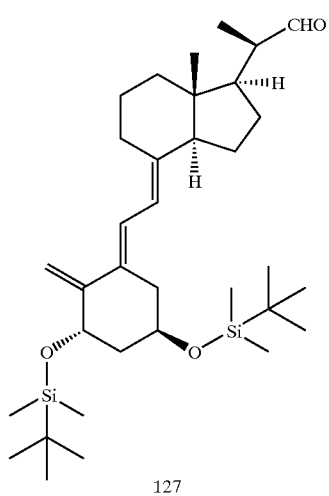
127
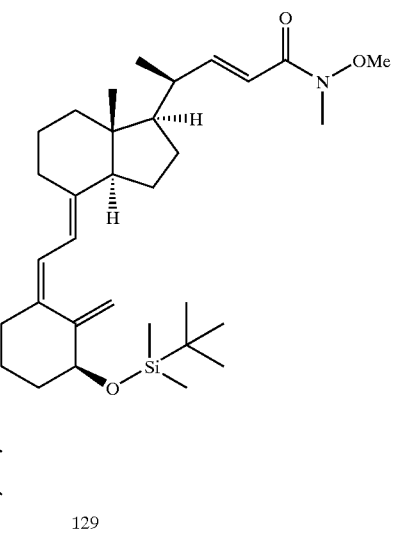 
129
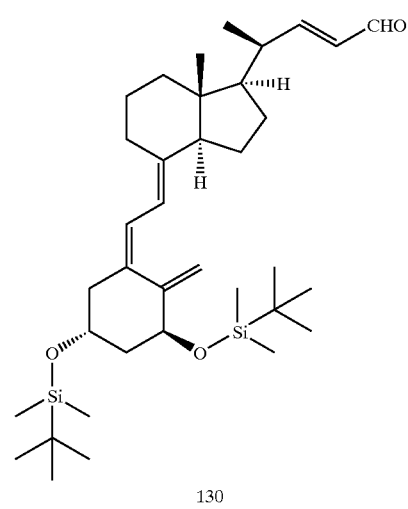 
130

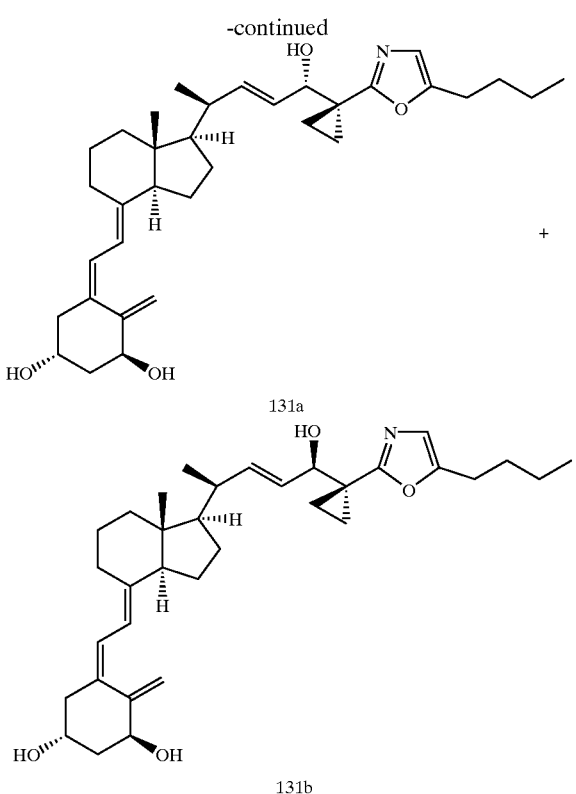

131a

131b

What is claimed is:

1. A compound of general formula I

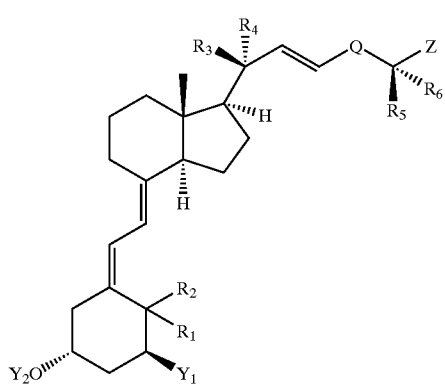

(I)

wherein

Y$_1$ means a hydrogen atom, a hydroxyl group, an alkanoyloxy group with 1 to 12 C atoms or an aroyloxy group, Y$_2$ means a hydrogen atom or an alkanoyl group with 1 to 12 C atoms or an aroyl group, R$_1$ and R$_2$ each mean a hydrogen atom or together an exocyclic methylene group, R$_3$ and R$_4$, independently of one another, mean a hydrogen atom, a chlorine or fluorine atom, an alkyl group with 1 to 4 carbon atoms, or together form a methylene group, or together with quaternary carbon atom 20 form a 3- to 7-membered, saturated or unsaturated carbocyclic ring, Q means a straight-chain or branched carbon unit with up to 10 carbon atoms, which at any position can have hydroxyl groups, in α- or β-position, which in turn can be etherified or esterified, keto groups, amino groups or halogen atoms, R$_5$ and R$_6$ together with carbon atom 25 mean a 3- to 7-membered, saturated or unsaturated carbocyclic ring, Z means an oxazole ring which can be substituted by one or more alkyl chains, which can be straight-chain or branched, saturated or unsaturated, and optionally interrupted by oxa, thia, aza, sulfoxide or sulfo groups or substituted by hydroxy groups or halogen atoms.

2. A compound according to claim 1, wherein Q has the meaning of a hydroxymethyl or carbonylmethyl group.

3. A process for the production of a compound of general formula I, according to claim 1, comprising:

providing a compound of general formula II

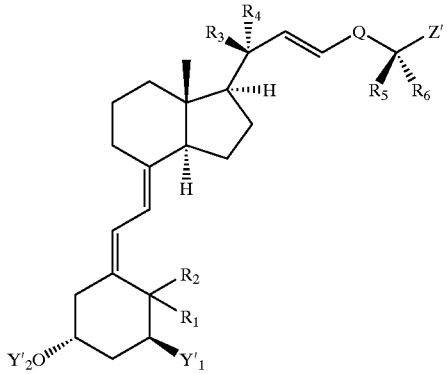

II wherein

Y'$_1$ means a hydrogen atom or a protected hydroxy group and

Y'$_2$ means a hydroxy protective group,

R$_1$ and R$_2$ each mean a hydrogen atom or together an exocyclic methylene group, R$_3$ and R$_4$, independently of one another, mean a hydrogen atom, a chlorine or fluorine atom, an alkyl group with 1 to 4 carbon atoms, or together form a methylene group, or together with quaternary carbon atom 20 form a 3- to 7-membered, saturated or unsaturated carbocyclic ring, Q means a straight-chain or branched carbon unit with up to 10 carbon atoms, which at any position can have hydroxyl groups, in α- or β-position, which in turn can be etherified or esterified, keto groups, amino groups or halogen atoms, R$_5$ and R$_6$ together with carbon atom 25 mean a 3- to 7-membered, saturated or unsaturated carbocyclic ring, Z' means an oxazole or isoxazole ring which can be substituted by one or more alkyl chains, which can be straight-chain or branched, saturated or unsaturated, and optionally interrupted by oxa, thia, aza, sulfoxide or sulfo groups or substituted by hydroxy groups or halogen atoms; and converting said compound of formula II into a compound of formula I by simultaneous or successive cleavage of the hydroxy protective groups and optionally by partial or complete esterification(s) or etherification(s) of free hydroxy groups.

4. A composition comprising at least one compound according to claim 1 and a pharmaceutically acceptable carrier.

5. A method of treating hyperproliferative diseases of the skin, tumor diseases and precancerous stages, auto-immune diseases, rejection reactions in the case of autologous, allogenic or xenogenic transplants, AIDS, atopic skin conditions, secondary hyperparathyroidism, renal osteodystrophia, senile and postmenopausal osteoporosis, diabetes mellitus type II, and degenerative diseases of the peripheral and central nervous system comprising administering a composition according to claim 4.

6. A method of treating hypercalcemias, granulomatous diseases, paraneoplastic hypercalcemias, hypercalcemias in hyperparathyroidism, hirsutism, ateriosclerosis, and inflammatory diseases comprising administering a composition according to claim 4, wherein the compound antagonizes the action of calcitriol in HL 60 cells.

7. A compound, wherein the compound is selected from the group consisting of:

(5Z,7E,22E)-(1S,3R,24S)-25-(5-propyloxazol-2-yl)-26,27-cyclo-9,10-secocholesta-5,7,10(19),22-tetraene-1,3,24-triol (5Z,7E,22E)-(1S,3R,24R)-25-(5-methyloxazol-2-yl)-26,27-cyclo-9,10-secocholesta-5,7,10(19),22-tetraene-1,3,24-triol (5Z,7E,22E)-(1S,3R,24S)-25-(5-methyloxazol-2-yl)-26,27-cyclo-9,10-secocholesta-5,7,10(19),22-tetraene-1,3,24-triol (5Z,7E,22E)-(1S,3R,24R)-25-(5-ethyloxazol-2-yl)-26,27-cyclo-9,10-secocholesta-5,7,10(19),22-tetraene-1,3,24-triol (5Z,7E,22E)-(1S,3R,24S)-25-(5-ethyloxazol-2-yl)-26,27-cyclo-9,10-secocholesta-5,7,10(19),22-tetraene-1,3,24-triol (5Z,7E,22E)-(1S,3R,24R)-25-(5-butyloxazol-2-yl)-26,27-cyclo-9,10-secocholesta-5,7,10(19),22-tetraene-1,3,24-triol (5Z,7E,22E)-(1S,3R,24S)-25-(5-butyloxazol-2-yl)-26,27-cyclo-9,10-secocholesta-5,7,10(19),22-tetraene-1,3,24-triol (5Z,7E,22E)-(1S,3R,24R)-25-(5-pentyloxazol-2-yl)-26,27-cyclo-9,10-secocholesta-5,7,10(19),22-tetraene-1,3,24-triol (5Z,7E,22E)-(1S,3R,24R)-25-(4-propyloxazol-2-yl)-26,27-cyclo-9,10-secocholesta-5,7,10(19),22-tetraene-1,3,24-triol (5Z,7E,22E)-(1S,3R,24S)-25-(4-propyloxazol-2-yl)-26,27-cyclo-9,10-secocholesta-5,7,10(19),22-tetraene-1,3,24-triol (5Z,7E,22E)-(1S,3R,24R)-25-(4-methyloxazol-2-yl)-26,27-cyclo-9,10-secocholesta-5,7,10(19),22-tetraene-1,3,24-triol (5Z,7E,22E)-(1S,3R,24S)-25-(4-methyloxazol-2-yl)-26,27-cyclo-9,10-secocholesta-5,7,10(19),22-tetraene-1,3,24-triol (5Z,7E,22E)-(1S,3R,24R)-25-(4-ethyloxazol-2-yl)-26,27-cyclo-9,10-secocholesta-5,7,10(19),22-tetraene-1,3,24-triol (5Z,7E,22E)-(1S,3R,24S)-25-(4-ethyloxazol-2-yl)-26,27-cyclo-9,10-secocholesta-5,7,10(19),22-tetraene-1,3,24-triol (5Z,7E,22E)-(1S,3R,24R)-25-(4-butyloxazol-2-yl)-26,27-cyclo-9,10-secocholesta-5,7,10(19),22-tetraene-1,3,24-triol (5Z,7E,22E)-(1S,3R,24S)-25-(4-butyloxazol-2-yl)-26,27-cyclo-9,10-secocholesta-5,7,10(19),22-tetraene-1,3,24-triol (5Z,7E,22E)-(1S,3R,24R)-25-(4-pentyloxazol-2-yl)-26,27-cyclo-9,10-secocholesta-5,7,10(19),22-tetraene-1,3,24-triol (5Z,7E,22E)-(1S,3R,24S)-25-(4-pentyloxazol-2-yl)-26,27-cyclo-9,10-secocholesta-5,7,10(19),22-tetraene-1,3,24-triol (5Z,7E,22E)-(1S,3R,20S,24R)-25-(5-propyloxazol-2-yl)-26,27-cyclo-9,10-secocholesta-5,7,10(19),22-tetraene-1,3,24-triol (5Z,7E,22E)-(1S,3R,20S,24S)-25-(5-propyloxazol-2-yl)-26,27-cyclo-9,10-secocholesta-5,7,10(19),22-tetraene-1,3,24-triol (5Z,7E,22E)-(1S,3R,20S,24R)-25-(5-methyloxazol-2-yl)-26,27-cyclo-9,10-secocholesta-5,7,10(19),22-tetraene-1,3,24-triol (5Z,7E,22E)-(1S,3R,20S,24S)-25-(5-methyloxazol-2-yl)-26,27-cyclo-9,10-secocholesta-5,7,10(19),22-tetraene-1,3,24-triol (5Z,7E,22E)-(1S,3R,20S,24R)-25-(5-ethyloxazol-2-yl)-26,27-cyclo-9,10-secocholesta-5,7,10(19),22-tetraene-1,3,24-triol (5Z,7E,22E)-(1S,3R,20S,24S)-25-(5-ethyloxazol-2-yl)-26,27-cyclo-9,10-secocholesta-5,7,10(19),22-tetraene-1,3,24-triol (5Z,7E,22E)-(1S,3R,20S,24R)-25-(5-butyloxazol-2-yl)-26,27-cyclo-9,10-secocholesta-5,7,10(19),22-tetraene-1,3,24-triol (5Z,7E,22E)-(1S,3R,20S,24S)-25-(5-butyloxazol-2-yl)-26,27-cyclo-9,10-secocholesta-5,7,10(19),22-tetraene-1,3,24-triol (5Z,7E,22E)-(1S,3R,20S,24R)-25-(5-pentyloxazol-2-yl)-26,27-cyclo-9,10-secocholesta-5,7,10(19),22-tetraene-1,3,24-triol (5Z,7E,22E)-(1S,3R,20S,24S)-25-(5-pentyloxazol-2-yl)-26,27-cyclo-9,10-secocholesta-5,7,10(19),22-tetraene-1,3,24-triol (5Z,7E,22E)-(1S,3R,20S,24R)-25-(4-propyloxazol-2-yl)-26,27-cyclo-9,10-secocholesta-5,7,10(19),22-tetraene-1,3,24-triol (5Z,7E,22E)-(1S,3R,20S,24S)-25-(4-propyloxazol-2-yl)-26,27-cyclo-9,10-secocholesta-5,7,10(19),22-tetraene-1,3,24-triol (5Z,7E,22E)-(1S,3R,20S,24R)-25-(4-methyloxazol-2-yl)-26,27-cyclo-9,10-secocholesta-5,7,10(19),22-tetraene-1,3,24-triol (5Z,7E,22E)-(1S,3R,20S,24S)-25-(4-methyloxazol-2-yl)-26,27-cyclo-9,10-secocholesta-5,7,10(19),22-tetraene-1,3,24-triol (5Z,7E,22E)-(1S,3R,20S,24R)-25-(4-ethyloxazol-2-yl)-26,27-cyclo-9,10-secocholesta-5,7,10(19),22-tetraene-1,3,24-triol (5Z,7E,22E)-(1S,3R,20S,24S)-25-(4-ethyloxazol-2-yl)-26,27-cyclo-9,10-secocholesta-5,7,10(19),22-tetraene-1,3,24-triol (5Z,7E,22E)-(1S,3R,20S,24R)-25-(4-butyloxazol-2-yl)-26,27-cyclo-9,10-secocholesta-5,7,10(19),22-tetraene-1,3,24-triol (5Z,7E,22E)-(1S,3R,20S,24S)-25-(4-butyloxazol-2-yl)-26,27-cyclo-9,10-secocholesta-5,7,10(19),22-tetraene-1,3,24-triol (5Z,7E,22E)-(1S,3R,20S,24R)-25-(4-pentyloxazol-2-yl)-26,27-cyclo-9,10-secocholesta-5,7,10(19),22-tetraene-1,3,24-triol (5Z,7E,22E)-(1S,3R,20S,24S)-25-(4-pentyloxazol-2-yl)-26,27-cyclo-9,10-secocholesta-5,7,10(19),22-tetraene-1,3,24-triol (5Z,7E,22E)-(1S,3R,24R)-20-methyl-25-(5-propyloxazol-2-yl)-26,27-cyclo-9,10-secocholesta-5,7,10(19),22-tetraene-1,3,24-triol (5Z,7E,22E)-(1S,3R,24S)-20-methyl-25-(5-propyloxazol-2-yl)-26,27-cyclo-9,10-secocholesta-5,7,10(19),22-tetraene-1,3,24-triol (5Z,7E,22E)-(1S,3R,24R)-20-methyl-25-(5-methyloxazol-2-yl)-26,27-cyclo-9,10-secocholesta-5,7,10(19),22-tetraene-1,3,24-triol (5Z,7E,22E)-(1S,3R,24S)-20-methyl-25-(5-methyloxazol-2-yl)-26,27-cyclo-9,10-secocholesta-5,7,10(19),22-tetraene-1,3,24-triol (5Z,7E,22E)-(1S,3R,24R)-25-(5-ethyloxazol-2-yl)-20-methyl-26,27-cyclo-9,10-secocholesta-5,7,10(19),22-tetraene-1,3,24-triol (5Z,7E,22E)-(1S,3R,24S)-25-(5-ethyloxazol-2-yl)-20-methyl-26,27-cyclo-9,10-secocholesta-5,7,10(19),22-tetraene-1,3,24-triol (5Z,7E,22E)-(1S,3R,24R)-25-(5-butyloxazol-2-yl)-20-methyl-6,27-cyclo-9,10-secocholesta-5,7,10(19),22-tetraene-1,3,24-triol (5Z,7E,22E)-(1S,3R,24S)-25-(5-butyloxazol-2-yl)-20-methyl-26,27-cyclo-9,10-secocholesta-5,7,10(19),22-tetraene-1,3,24-triol (5Z,7E,22E)-(1S,3R,24R)-20-methyl-25-(5-pentyloxazol-2-yl)-26,27-cyclo-9,10-secocholesta-5,7,10(19),22-tetraene-1,3,24-triol (5Z,7E,22E)-(1S,3R,24S)-20-methyl-25-(5-pentyloxazol-2-yl)-26,27-cyclo-9,10-secocholesta-5,7,10(19),22-tetraene-1,3,24-triol (5Z,7E,22E)-(1S,3R,24R)-20-methyl-25-(4-propyloxazol-2-yl)-26,27-cyclo-9,10-secocholesta-5,7,10(19),22-tetraene-1,3,24-triol (5Z,7E,22E)-(1S,3R,24S)-20-methyl-25-(4-propyloxazol-2-yl)-26,27-cyclo-9,10-secocholesta-5,7,10(19),22-tetraene-1,3,24-triol (5Z,7E,22E)-(1S,3R,24R)-20-methyl-25-(4-methyloxazol-2-yl)-26,27-cyclo-9,10-secocholesta-5,7,10(19),22-tetraene-1,3,24-triol (5Z,7E,22E)-(1S,3R,24S)-20-methyl-25-(4-methyloxazol-2-yl)-26,27-cyclo-9,10-secocholesta-5,7,10(19),22-tetraene-1,3,24-triol (5Z,7E,22E)-(1S,3R,24R)-25-(4-ethyloxazol-2-yl)-20-methyl-26,27-cyclo-9,10-secocholesta-5,7,10(19),22-tetraene-1,3,24-triol (5Z,7E,22E)-(1S,3R,24S)-25-(4-ethyloxazol-2-yl)-20-methyl-26,27-cyclo-9,10-secocholesta-5,7,10(19),22-tetraene-1,3,24-triol (5Z,7E,22E)-(1S,3R,24R)-25-(4-butyloxazol-2-yl)-20-methyl-26,27-cyclo-9,10-secocholesta-5,7,10(19),22-tetraene-1,3,24-triol (5Z,7E,22E)-(1S,3R,24S)-25-(4-butyloxazol-2-yl)-20-methyl-26,27-cyclo-9,10-secocholesta-5,7,10(19),22-tetraene-1,3,24-triol (5Z,7E,22E)-(1S,3R,24R)-20-methyl-25-(4-pentyloxazol-2-yl)-26,27-cyclo-9,10-secocholesta-5,7,10(19),22-tetraene-1,3,24-triol (5Z,7E,22E)-(1S,3R,24S)-20-methyl-25-(4-pentyloxazol-2-yl)-26,27-cyclo-9,10-secocholesta-5,7,10(19),22-tetraene-1,3,24-triol.

8. A compound according to claim 1, wherein $Y_1$ is acetyloxy, propionyloxy, butyryloxy or benzoyloxy.

9. A compound according to claim 1, wherein $Y_2$ is acetyl, propionyl, butyryl or benzoyl.

10. A compound according to claim 1, wherein $R_3$ is H and $R_4$ is methyl.

11. A compound according to claim 1, wherein $R_3$ is methyl and $R_4$ is H.

12. A compound according to claim 1, wherein $R_3$ is F and $R_4$ is methyl.

13. A compound according to claim 1, wherein $R_3$ is methyl and $R_4$ is F.

14. A compound according to claim 1, wherein $R_3$ is and $R_4$ together form a methylene group or together with tertiary carbon atom 20 form a cyclopropyl group.

15. A compound according to claim 1, wherein Q is an unsubstituted, unbranched alkylene having 1–3 carbon atoms.

16. A compound according to claim 1, wherein Q is hydroxymethylene in which the hydroxy group is in the α or β position.

17. A compound according to claim 1, wherein Q is —CH(OH)—CH2— or —CH(OH)—CH2—CH2— in which, in each case, the hydroxy group is in the α or β position.

18. A compound according to claim 1, wherein $R_5$ and $R_6$ together with carbon atom C-25 form a cyclopropyl, cyclobutyl, cyclopentyl, or cyclohexyl group.

19. A compound according to claim 1, wherein $R_5$ and $R_6$ together with carbon atom C-25 form a cyclopropyl group.

20. A compound according to claim 1, wherein Z is oxazole.

21. A compound according to claim 1, wherein Z is isoxazole.

22. A method of treating hyperprolifierative diseases of the skin and deficient cell differentiation diseases comprising administering to a patient an effective amount of a composition according to claim 4.

23. A method according to claim 23, wherein said patient is suffering from psoriasis, pityriasis subia pilasis, acne, itchyosis, or combinations thereof.

24. A method according to claim 23, wherein said patient is suffering from tumors of the intestines, carcinomas of the breast, lung tumors, prostrate carcinomas, leukemias, T-cell lymphomas, melanomas, Batazell Larzin, squamos carcinomas, acetinic keratoses, cervix dysplasias, or combinations thereof.

25. A compound of formula I (I)

wherein $Y_1$ means a hydrogen atom, a hydroxyl group, an alkanoyloxy group with 1 to 12 C atoms or an aroyloxy group, $Y_2$ means a hydrogen atom or an alkanoyl group with 1 to 12 C atoms or an aroyl group, $R_1$ and $R_2$ each mean a hydrogen atom or together an exocyclic methylene group, $R_3$ and $R_4$, independently of one another, mean a hydrogen atom, a chlorine or fluorine atom, an alkyl group with 1 to 4 carbon atoms, or together form a methylene group, or together with quaternary carbon atom 20 form a 3- to 7-membered, saturated or unsaturated carbocyclic ring, Q means a straight-chain or branched carbon unit with up to 10 carbon atoms, which at any position can have hydroxyl groups, in α- or β-position, which in turn can be etherified or esterified, keto groups, amino groups or halogen atoms, R₅ and R₆ at the same time each mean a hydrogen atom, a chlorine or fluorine atom, a trifluoromethyl group, a straight-chain or branched-chain, saturated or unsaturated, hydrocarbon radical with up to 4 carbon atoms, or R₅ and R₆ together with carbon atom 25 mean a 3- to 7-membered, saturated or unsaturated, carbocyclic ring, Z means an oxazole or isoxazole ring which can be substituted by one or more alkyl chains, which can be straight-chain or branched, saturated or unsaturated, and optionally interrupted by oxa, thia, aza, sulfoxide or sulfo groups or substituted by hydroxy groups, or halogen atoms.

26. A compound according to claim 25, wherein R₅ and R₆ are each methyl or ethyl.

27. A compound according to claim 25, wherein R₅ and R₆ are each methyl or R₅ and R₆ together with carbon atom C-25 form a cyclopropyl group.

28. A process for the production of compound, according to claim 1, comprising:

providing a compound of formula II

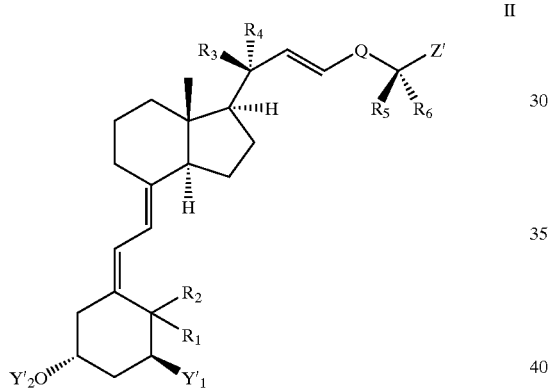

II wherein

Y'₁ means a hydrogen atom or a protected hydroxy group,

Y'₂ means a hydroxy protective group,

R₁ and R₂ each mean a hydrogen atom or together form an exocyclic methylene group, R₃ and R₄, independently of one another, mean a hydrogen atom, a chlorine or fluorine atom, an alkyl group with 1 to 4 carbon atoms, or together form a methylene group, or together with quaternary carbon atom 20 form a 3- to 7-membered, saturated or unsaturated, carbocyclic ring, Q means a straight-chain or branched carbon unit with up to 10 carbon atoms, which at any position can have hydroxyl groups, in α- or β-position, which in turn can be etherified or esterified, keto groups, amino groups or halogen atoms, R₅ and R₆ at the same time each mean a hydrogen atom, a chlorine or fluorine atom, a trifluoromethyl group, a straight-chain or branched-chain, saturated or unsaturated, hydrocarbon radical with up to 4 carbon atoms, or R₅ and R₆ together with carbon atom 25 mean a 3- to 7-membered, saturated or unsaturated, carbocyclic ring, Z' means an oxazole or isoxazole ring which can be substituted by one or more alkyl chains, which can be straight-chain or branched, saturated or unsaturated, and optionally interrupted by oxa, thia, aza, sulfoxide or sulfo groups or substituted by hydroxy groups or halogen atoms; and converting said compound of formula II into a compound of formula I by simultaneous or successive cleavage of the hydroxy protective groups and optionally by partial or complete esterification(s) or etherification(s) of free hydroxy groups.

* * * * *

UNITED STATES PATENT AND TRADEMARK OFFICE
CERTIFICATE OF CORRECTION

PATENT NO. : 6,642,218 B2
DATED : November 4, 2003
INVENTOR(S) : Andreas Steinmeyer et al.

It is certified that error appears in the above-identified patent and that said Letters Patent is hereby corrected as shown below:

Column 102,
Lines 24 and 27, reads "claim 23" should read -- claim 22 --

Signed and Sealed this

Twenty-first Day of September, 2004

JON W. DUDAS
*Director of the United States Patent and Trademark Office*